United States Patent
Miyagi et al.

(10) Patent No.: US 6,689,049 B1
(45) Date of Patent: *Feb. 10, 2004

(54) ENDOSCOPE

(75) Inventors: Takayasu Miyagi, Hachioji (JP); Michio Satou, Hachioji (JP); Hideo Ito, Akishima (JP); Akira Suzuki, Kitatsuru-gun (JP); Atsushi Watanabe, Hino (JP); Kan Naito, Hachioji (JP); Ryuichi Toyama, Hachioji (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 111 days.

(21) Appl. No.: 09/588,083

(22) Filed: Jun. 6, 2000

(30) Foreign Application Priority Data

Jun. 7, 1999 (JP) .......................................... 11-159428
Jun. 14, 1999 (JP) .......................................... 11-167173
Jun. 21, 1999 (JP) .......................................... 11-174090

(51) Int. Cl.$^7$ ................................................. A61B 1/00
(52) U.S. Cl. ........................ 600/117; 600/129; 600/130; 600/424
(58) Field of Search ................................. 600/104, 114, 600/117, 118, 129, 130, 139–142, 424

(56) References Cited

U.S. PATENT DOCUMENTS 5,454,366 A * 10/1995 Ito et al. ..................... 600/109
5,840,024 A 11/1998 Taniguchi et al.

FOREIGN PATENT DOCUMENTS

| JP | 7-39510 | * 2/1995 | ............ A61B/1/00 |
|---|---|---|---|
| JP | 7-111968 | 5/1995 | |
| JP | 7-111969 | 5/1995 | |
| JP | 8-542 | 1/1996 | |
| JP | 08-107875 | 4/1996 | |
| JP | 09-28662 | 2/1997 | |
| JP | 09-84745 | 3/1997 | |
| JP | 10-75929 | 3/1998 | |
| JP | 10-338031 | 11/1998 | |
| JP | 10-343159 | 12/1998 | |
| JP | 10-348890 | 12/1998 | |
| JP | 10-359670 | 12/1998 | |
| JP | 10-374010 | 12/1998 | |
| JP | 2000-81301 | 3/2000 | |
| JP | 2000-81302 | 3/2000 | |
| JP | 2000-93386 | 4/2000 | |
| JP | 2000-93387 | 4/2000 | |

* cited by examiner

*Primary Examiner*—John Mulcahy
(74) *Attorney, Agent, or Firm*—Frishauf, Holtz, Goodman & Chick, P.C.

(57) ABSTRACT

Three magnetic field generating coils on the distal end side of the shape detection probe are provided in the curvable portion, and the first coil at the leading end position is placed at the position corresponding to the leading end curvable piece, whereas the third coil at the position corresponding to the trailing end curvable piece. Further, the second coil is placed at a middle position between the leading end curvable piece and the trailing end curvable piece in the curvable portion. With this structure, the accuracy of detecting the shape of the curvable portion can be improved, and the production cost of the system as a whole can be lowered.

19 Claims, 23 Drawing Sheets

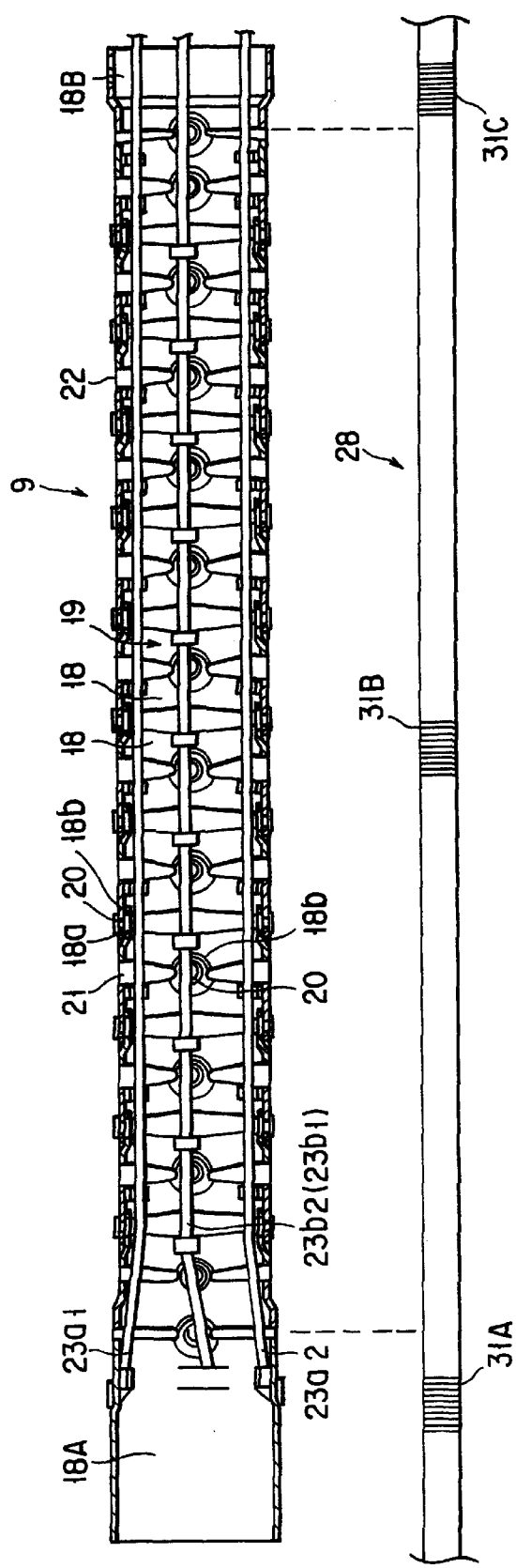
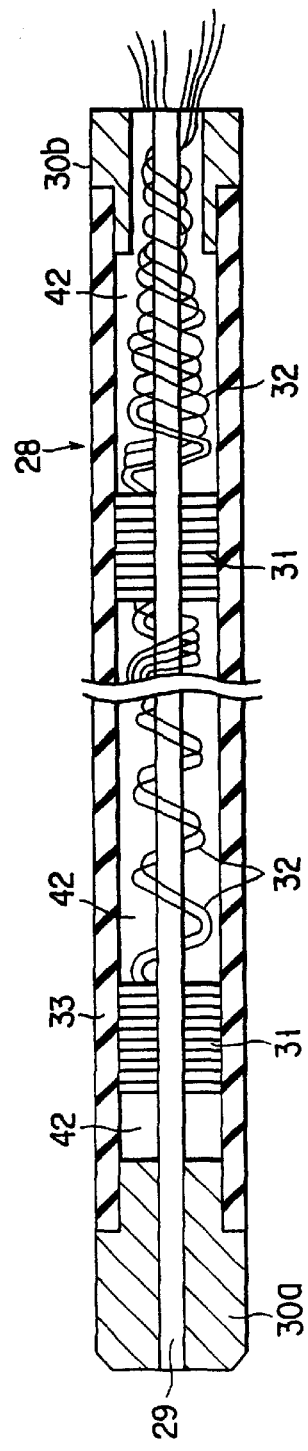
FIG. 2A
FIG. 2B

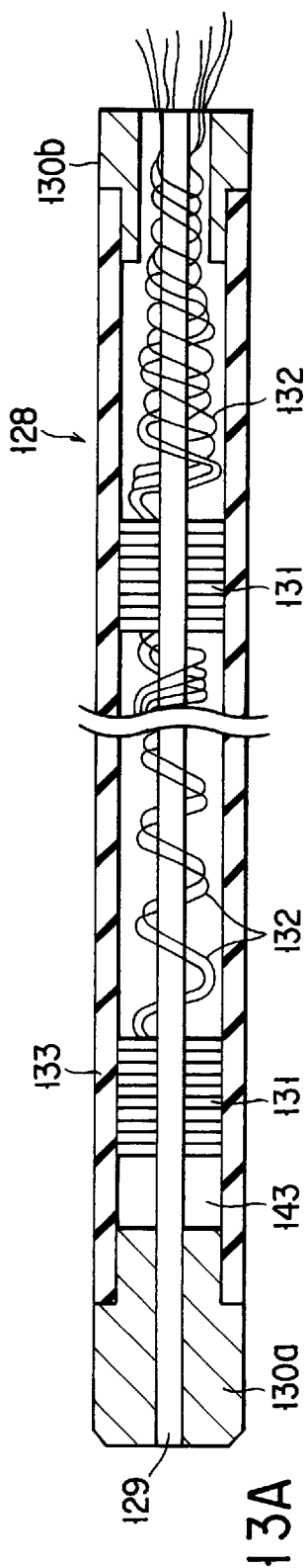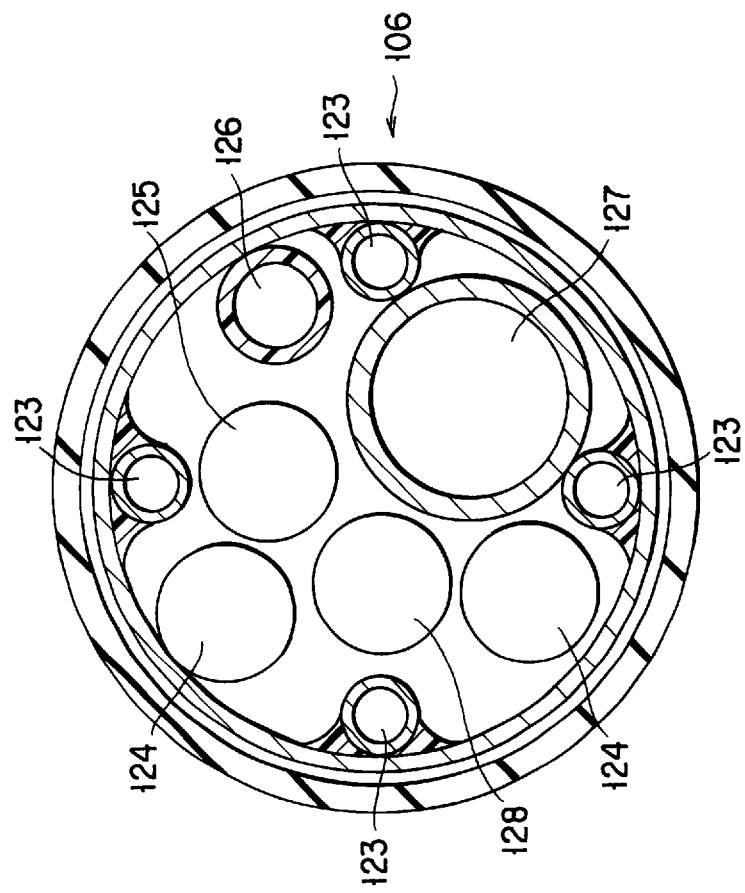
FIG. 13A
FIG. 13B

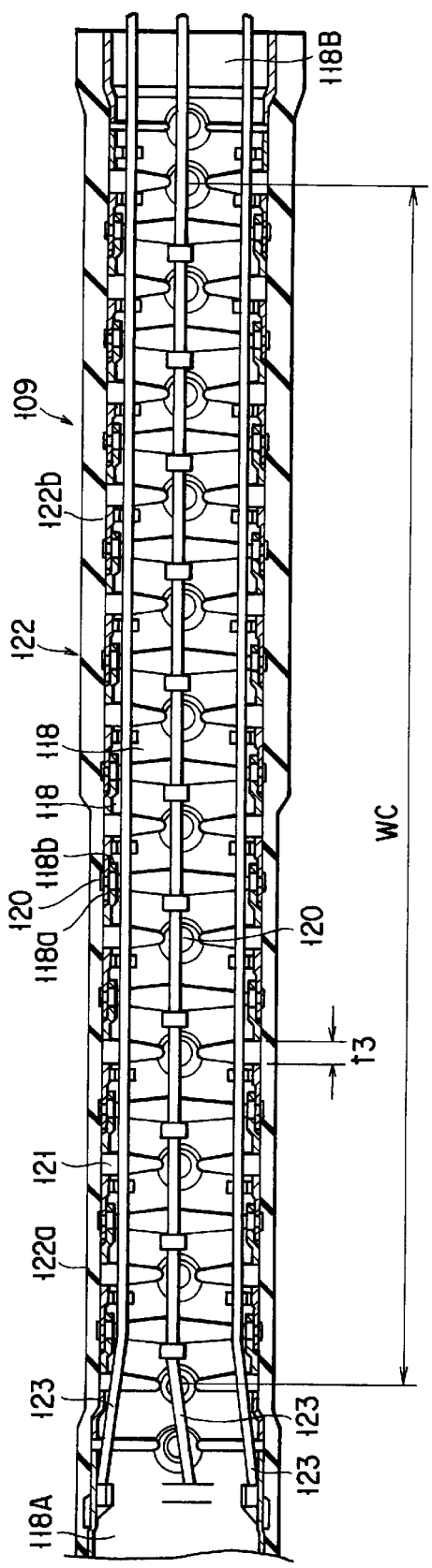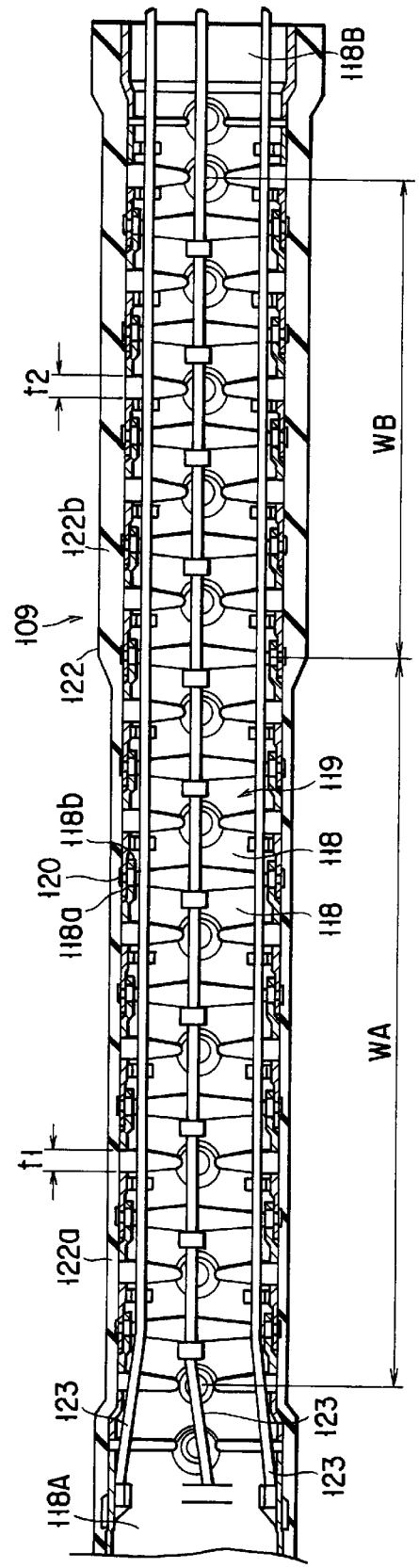
FIG. 17A
FIG. 17B

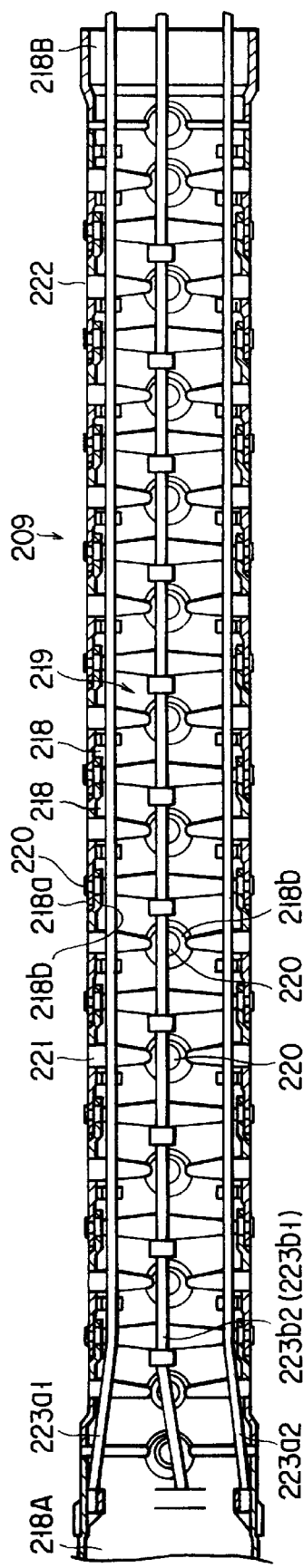
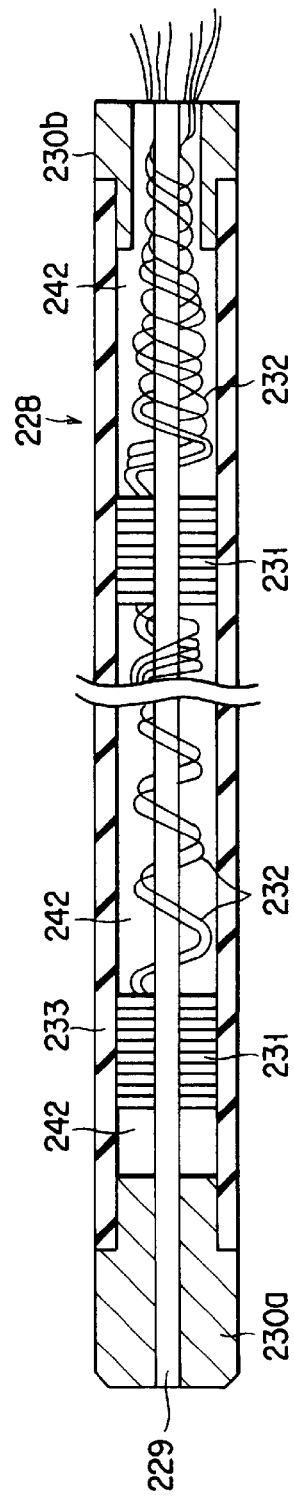
FIG. 24A
FIG. 24B

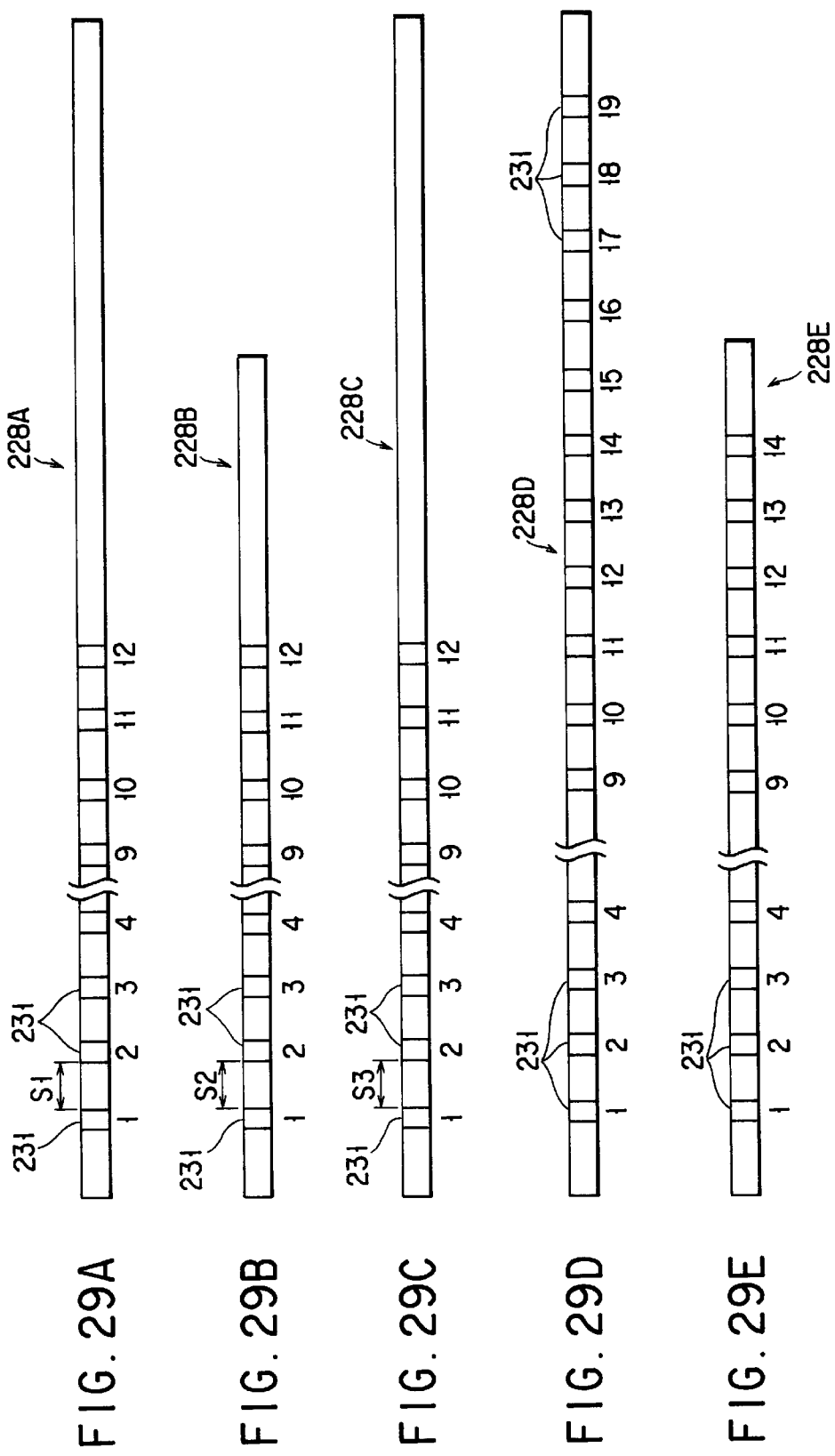

ENDOSCOPE

CROSS-REFERENCE TO RELATED APPLICATIONS

This application is based upon and claims the benefit of priority from the prior Japanese Patent Applications No. 11-159428, filed Jun. 7, 1999; No. 11-167173, filed Jun. 14, 1999, and No. 11-174090, filed Jun. 21, 1999, the entire contents of which are incorporated herein by reference.

BACKGROUND OF THE INVENTION

The present invention relates to an endoscope having means for detecting a shape of an insertion portion when the insertion portion of the endoscope is inserted to a cavity for a pipe path used for an industrial purpose, or such as a cavity of a body canal.

Generally, in an endoscope, a hand-side operation portion is provided at a proximal portion of a slender insertion portion to be inserted into a cavity of a body canal. Further, a curvable portion which is made curvedly deformable is provided at a distal end of the insertion portion. Further, a curving operation portion such as a curvature knob, for operating the curvable portion to curve accordingly, is provided in the operation portion.

In the insertion portion of the endoscope, a distal end structure portion is provided at the distal end of a soft and slender flexible tube portion via the curvable portion. An illumination optical system, an observation optical system and the like are built in the distal end structure portion. In the case where the insertion portion of the endoscope is inserted into the cavity of a body canal, the insertion portion is gradually pushed into the cavity of the body canal by operating the curvable portion to curve to follow the shape of the cavity of the canal. Thus, the insertion portion of the endoscope can be inserted to a deep section of the body canal while deforming the flexible tube section of the endoscope to follow the shape of the body canal. Here, the cavity of a body canal in which the insertion portion of the endoscope is to be inserted, such as that of a large intestine or small intestine, is complicatedly curved around inside. Thus, the shape of the insertion portion of the endoscope inserted in the cavity of the body canal is changed in accordance with the shape of the body canal in which the portion is inserted, and therefore it is not easy for the operator to know the shape of the insertion portion of the endoscope inserted in the deep section of the body canal.

Under these circumstances, for example, Jap. Pat. Appln. KOKAI Publication No. 7-111969 proposes an endoscope which contains an insertion portion shape detection probe for detecting the shape of the insertion portion of the endoscope inserted in the cavity of a body canal. In this document, a core wire is provided in the insertion portion shape detection probe at its axial center portion. Around the core wire, a plurality of coils each for generating a magnetic field are arranged side by side within the insertion portion of the endoscope along its axial direction. These coils are fixed at preset intervals with an adhesive or the like.

To each coil, a signal line is connected. Further, an armor tube is provided around an outer circumference of the shape detection probe so as to protect these coils and signal lines. The endoscope has such a structure that a magnetic field generated from each magnetic field generating coil is detected so as to detect the shape of the insertion portion, and the detected shape of the insertion portion is displayed on a monitor exclusively provided for the purpose.

In the above-described device of the conventional structure, a plurality of coils of the shape detection probe are arranged dispersedly at appropriate locations in the curvable portion of the insertion portion of the endoscope, and in the flexible tube portion. Here, in the case where there are a great number of coils of the shape detection probe, provided in the insertion portion of the endoscope, the accuracy of the detection of the shape of the insertion portion of the endoscope is improved; however, the cost for such a shape detection probe becomes expensive, thus raising the production cost of the entire system of the endoscope device as a problem.

On the contrary, in the case where there are a few number of coils of the shape detection probe, arranged in the insertion portion of the endoscope, the accuracy of the detection of the shape of the insertion portion of the endoscope is deteriorated. Consequently, the shape of the insertion portion of the endoscope cannot be accurately displayed on the monitor. Thus, if the positions of the coils are not proper, the shape of the curvable portion, which changes its shape in a relatively complicated manner, cannot be displayed accurately.

BRIEF SUMMARY OF THE INVENTION

The present invention has been proposed in consideration of the above-described circumferences, and an object thereof is to provide an endoscope device with an improved accuracy of the detection of the shape of the curvable portion, which is capable of reducing the production cost of the entire system.

In order to achieve the above-described object, there is provided according to the present invention, an endoscope device including: an endoscope having a curvable portion capable of changing its shape in a curvable manner, in an insertion potion to be inserted to a cavity of a canal; and an insertion portion shape detection device for detecting a shape of the insertion portion;

the insertion portion containing an insertion portion shape detection probe in which a plurality of magnetic field generating coils each generating a magnetic field are arranged within the insertion portion along its axial direction, the insertion portion shape detection device including a detection portion for detecting a shape of the insertion portion by detecting the magnetic field generated from each magnetic field generating coil, wherein the shape detection probe includes:

a first coil, provided at neighborhood of a distal end position of the curvable portion, for detecting the distal end position, a second coil, provided at neighborhood of a rear end position of the curvable portion, for detecting the rear end position of the curvable portion, and a third coil at an intermediate position situated between the first coil and the second coil.

In the present invention, while operating the curvable portion to curve, neighborhood of the end positions of both the front and rear portions of the curvable portion are detected with use of the first coil for detecting the distal end position, and the second coil for detecting the rear end position of the curvable portion, and the mid position between both the front and rear end portions of the curvable portion is detected by the third coil situated at the mid position between both the front and rear end portions. As these detected points are connected with a smooth line, the shape of the curvable portion can be detected almost precisely.

Therefore, according to the present invention, all of the coils of the shape detection probe provided in the curvable portion are arranged at neighborhood of the front and end portions of the curvable portion as well as between both the front and rear end portions. With this structure, the accuracy of the detection of the shape of the curvable portion can be improved, and the production cost of the entire system can be reduced.

Further, another object of the present invention is to provide an endoscope device capable of reducing the possibility that the connection portion between the coil end in the shape detection probe and a signal line, or around the end edge of the coil of the armor tube is broken while operating the curvable portion to curve, so as to improve the durability of the shape detection probe.

In order to achieve the above-described object, there is provided according to the present invention, an endoscope device including: an endoscope having a curvable portion capable of changing its shape in a curvable manner, in an insertion potion to be inserted to a cavity of a canal; and an insertion portion shape detection device for detecting a shape of the insertion portion;

the insertion portion containing an insertion portion shape detection probe in which a plurality of magnetic field generating coils each generating a magnetic field are arranged within the insertion portion along its axial direction, the insertion portion shape detection device including a detection portion for detecting a shape of the insertion portion by detecting the magnetic field generated from each magnetic field generating coil, the curvable portion having a plurality of curvable regions having different radiuses of curvature from each other, and the shape detection probe having such an arrangement that the coils are provided in a region of the curvable portion, where the radius of curvature is large.

In the present invention, the curvable portion is operated to curve by bending a plurality of curvable regions of the curvable portion at different radiuses of curvature respectively. Here, with such an arrangement that all of the coils of the shape detection probe provided in the curvable portion are provided in a region where the radius of curvature is large, the tensile force and bending force acting on a connection portion between a coil end of the shape detection probe and a signal line, around an end edge of the coil of the armor tube and the like while operating the curvable portion to curve, are made small.

As described above, according to the present invention, a plurality of curvable regions of different radiuses of curvature from each other, are provided in the curvable portion, and all of the coils of the shape detection probe provided in the curvable portion are provided in a region of the curvable portion, where the radius of curvature is large. Therefore, the breakage of the probe, that is, the connection portion between a coil end of the shape detection probe and a signal line, an end edge of the armor tube and the like, being broken, can be prevented from easily occurring, and therefore the durability of the shape detection probe can be improved.

Furthermore, another object of the present invention is to provide an endoscope device in which the durability of the shape detection probe built in the endoscope can be improved by reducing the possibility of the connection portion between a coil end of the shape detection probe and a signal line, around an end edge of the coil of the armor tube and the like, being broken.

In order to achieve the above-described object, there is provided according to the present invention, an endoscope device including: an endoscope having a curvable portion capable of changing its shape in a curvable manner, in an insertion potion to be inserted to a cavity of a canal; and an insertion portion shape detection device for detecting a shape of the insertion portion;

the insertion portion containing an insertion portion shape detection probe in which a plurality of magnetic field generating coils each generating a magnetic field are arranged within the insertion portion along its axial direction, the insertion portion shape detection device including a detection portion for detecting a shape of the insertion portion by detecting the magnetic field generated from each magnetic field generating coil, and the insertion portion shape detection probe situated at such a position that a moving amount of the insertion portion shape detection probe in an axial direction of the insertion portion becomes minimum.

In the present invention, the moving amount in the axial direction with respect to the curving operation may be small. Therefore, the compression and tension applied on the insertion portion shape detection probe while operating the curvable portion, are reduced. Thus, the durability of the insertion portion shape detection probe is improved, and the durability of the endoscope in which the insertion portion shape detection probe is built, is improved.

Thus, according to the present invention, the insertion portion shape detection probe is arranged at such a position that the moving amount of the insertion portion shape detection probe in the axial direction of the insertion portion becomes minimum, while bending the curvable portion. With this structure, the breakage of the probe, that is, the connection portion between a coil end of the shape detection probe and a signal line, an end edge of the armor tube and the like, being broken, can be prevented from easily occurring, and therefore the durability of the shape detection probe can be improved.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2A is a diagram showing the relationship between the position of a curvable portion and the arrangement of coils of the shape detection probe built in the curvable portion, in the endoscope of the first embodiment;

FIG. 2B is a lateral view showing a shape detection probe disposed in an insertion portion of the endoscope according to the first embodiment;

FIG. 13A is a longitudinal sectional view showing the shape detection probe built in the endoscope according to the seventh embodiment;

FIG. 13B is a cross sectional view of an insertion portion in the endoscope according to the seventh embodiment;

FIG. 17A is a longitudinal sectional view showing an internal structure of a curvable portion in the endoscope according to the eighth embodiment;

FIG. 17B is a longitudinal sectional view showing an internal structure of a curvable portion in the endoscope according to the ninth embodiment;

FIG. 24A is a longitudinal sectional view showing an internal structure of a curvable portion in the endoscope according to the fourteenth embodiment;

FIG. 24B is a longitudinal sectional view showing an internal structure of a shape detection probe provided in an insertion portion of the endoscope according to the fourteenth embodiment;

FIG. 29A is a longitudinal sectional view designed to illustrate an arrangement state of coils of a shape detection probe built in the endoscope having a long-scale insertion portion, in the seventeenth embodiment;

FIG. 29B is a longitudinal sectional view designed to illustrate an arrangement state of coils of a shape detection probe built in the endoscope having a short-scale insertion portion, in the seventeenth embodiment;

FIG. 29C is a longitudinal sectional view designed to illustrate an arrangement state of coils of a shape detection probe inserted in a treatment tool through channel of the endoscope according to the seventeenth embodiment;

FIG. 29D is a longitudinal sectional view designed to illustrate an arrangement state of coils of a shape detection probe built in an endoscope having a long-scale insertion portion, according to a prior art technique;

FIG. 29E is a longitudinal sectional view designed to illustrate an arrangement state of coils of a shape detection probe built in an endoscope having a short-scale insertion portion, according to a prior art technique;

DETAILED DESCRIPTION OF THE INVENTION

Figure 1:
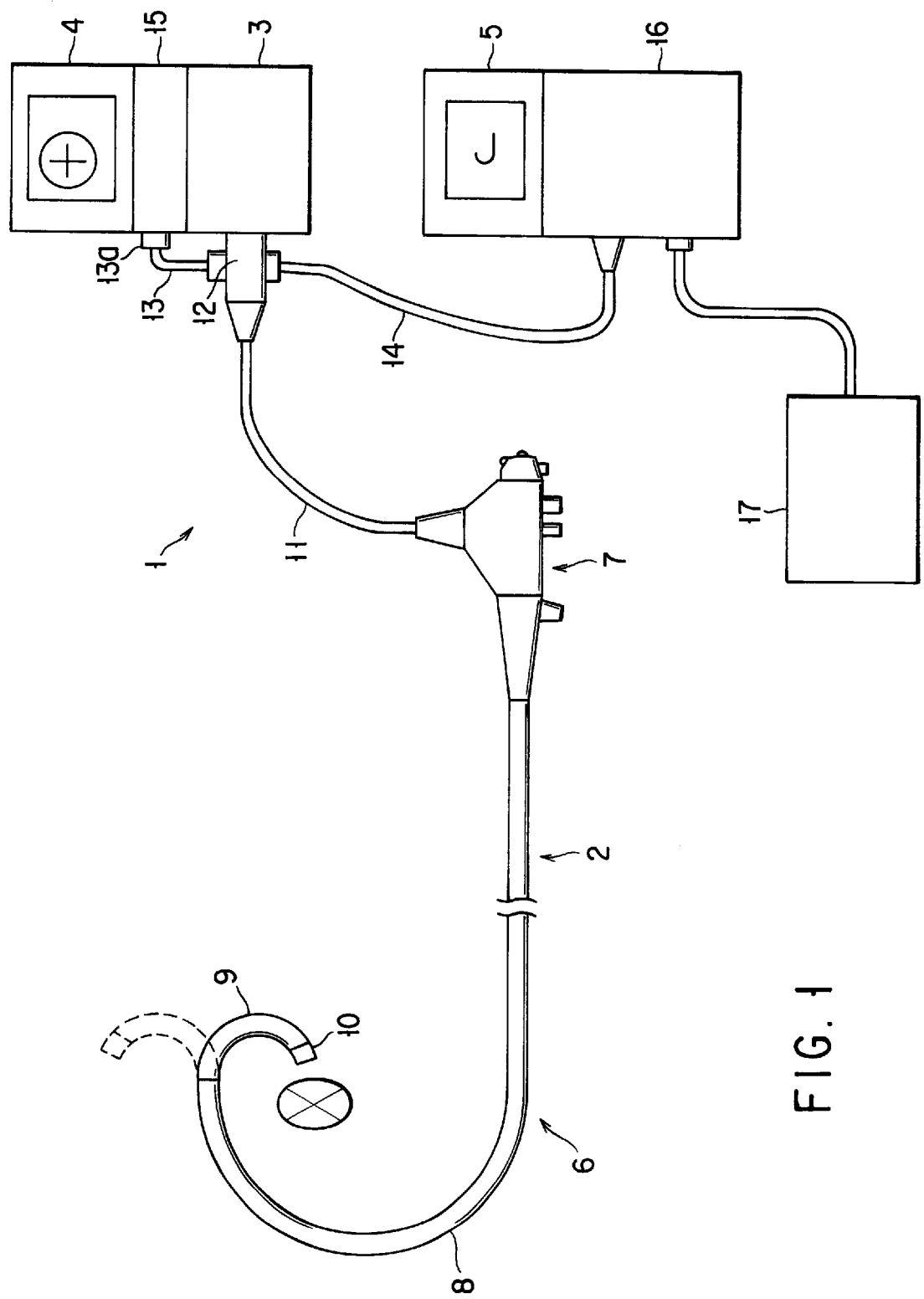
FIG. 1 is a schematic structural diagram showing an entire endoscope device according to the first embodiment of the present invention.

The first embodiment of the present invention will now be described with reference to FIGS. 1 to 4. FIG. 1 shows a schematic structure of an entire system of an endoscope device 1 according to this embodiment. In the endoscope device 1 of this embodiment, an endoscope 2, a light source unit 3, a first monitor 4 for displaying an endoscopic image and a second monitor 5 for displaying a shape of the endoscope 2 are provided.

In the endoscope 2 of this embodiment, a hand-side operating portion 7 is provided in a proximal end portion of a slender insertion portion 6 to be inserted into a cavity of a body canal. Here, in the insertion portion 6, a curvable portion 9 which can change its shape in a curved state is provided in a distal end portion of a slender flexible tube portion 8. Further, a hard distal end structural portion 10 is connected to a distal end portion of the curvable portion 9. In the distal end structural portion 10, not only a light guide fiber 24 (see FIG. 4), which serves as an illumination optical system, an objective lens 38 of an observation optical system 37 (see FIG. 3), and imaging means such as a CCD 39, but also air-supply and water-supply nozzles and a treatment tool through channel 27 (see FIG. 4) are built.

At the operation portion 7 on the hand side of the endoscope 2, a curving operation portion such as a curving knob for operating the curvable portion 9 to curve, is provided, and one end portion of a universal code 11 is connected to the operation portion 7. A connector 12 is mounted to another end portion of the universal code 11. Further, the connector 12 is detachably connected to the light source device 3.

Further, one end portion of each of two connection cables 13 and 14 is connected to the connector 12. Here, one connection cable 13 is connected to the control device 15 such as a camera control unit (CCU). To the control device 15, the first monitor 4 is connected.

The other connection cable 14 is connected to a shape detection control device 16 designed for detecting the shape of the insertion portion 6 of the endoscope 2. To the shape detection control device 16, an antenna 17 and a second monitor 5 are connected.

FIG. 2A shows an internal structure of the curvable portion 9 of the endoscope 2. In the curvable portion 9 of this embodiment, a curvable piece group 19 in which a plurality of ring-like curvable pieces 18 are arranged side by side in the axial direction of the insertion portion 6 is provided. Here, two front-end side projecting portions 18a are set in a front-end portion of each curvable piece 18 to project forwards. The two front-end side projecting portions 18a are arranged at positions which are 180 degrees away from each other in the circumferential direction of the ring of each curvable piece 18.

Further, two rear-end side projecting portions 18b are set in a rear end portion of each curvable piece 18 to project backwards. The two rear end side projecting portions 18b are arranged at positions which are 180 degrees away from each other in the circumferential direction of the ring of each curvable piece 18. With the above-described arrangement, the two front end side projecting portions 18a and the two rear end side projecting portions 18b of each curvable piece 18 are arranged at positions 90 degrees away from each other.

When there are two curvable pieces, one in front and the other in rear, to be adjacent to each other, there is created an overlap section where the two rear end side projecting portions 18b of a front-side curvable piece 18, and the two front end side projecting portions 18a of a rear-side curvable piece 18 overlap, and a pivotal pin 20 is connected to be pivotable to the overlap section.

Further, as can be seen in FIG. 2A, in the curvable portion 9 of the embodiment, gap portions 21 of substantially a V-letter shape are made on both sides of a pivot joint portion made of the pivotal pin 20 located between end edge portions of front-to-rear adjacent two curvable pieces 18.

In the leading end curvable piece 18A located at the first leading position of the curvable piece group 19, two front end side projecting portions 18a are not provided. The leading end curvable piece 18A is fixed to the rear end portion of the distal end structural portion 10 with fixation means such as adhesion, spiral piece, soldering, welding or press fitting. Further, in a trailing end curvable piece 18B located at the last trailing position of the curvable piece group 19, two rear end side projecting portions 18b are not provided. The trailing end curvable piece 18B is fixed to the distal end portion of the flexible tube portion 8 with fixation means such as adhesion, spiral piece, soldering, welding or press fitting.

A flexible soft tube member 22 is provided on an outer circumferential surface of the curvable portion 9. An outer side of the curvable piece group 19 of the curvable portion 9 is covered by the tube member 22.

Figure 4:
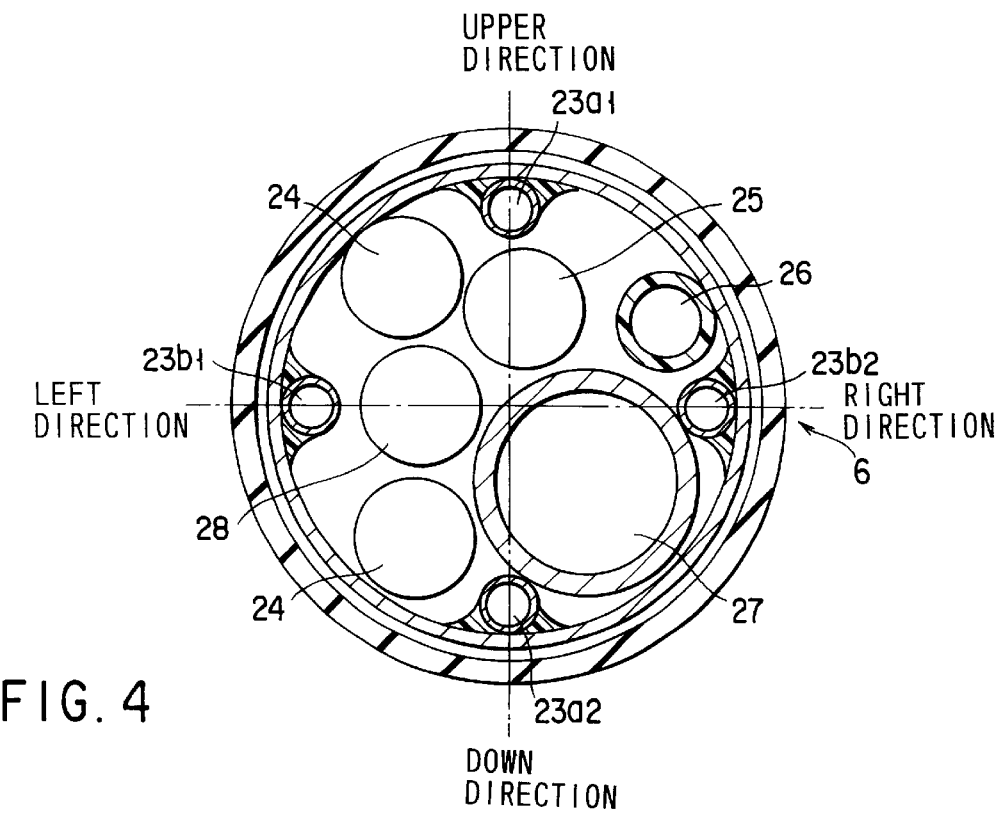
FIG. 4 is a cross sectional view taken along the line IV—IV in FIG. 3.

Further, as shown in FIG. 4, a plurality of, in this embodiment, four angle wires 23 (that is, two angle wires 23a1 and 23a2 for an up-and-down direction curving operation, and two angle wires 23b1 and 23b2 for a right-to-left direction curving operation) are fixed by their distal end portions to the leading end curvable piece 18A of the curvable portion 9. The proximal end portions of these angle wires 23 are extended out to the hand-side operating portion 7. The operating portion 7 is provided with a curving operation mechanism, though it is not shown in the figure, for pulling each of the angle wires 23 as the operation knob is operated.

In order to curve the curvable portion 9 of the endoscope 2, any one or two of the angle wires 23 are pulled via the curving operation mechanism by operating the operation knob. Here, the curvable portion 9 of the endoscope 2 is operated with the curving operation portion such as the curving knob of the operation portion 7, and thus it is curved from a standard shape drawn in substantially a linear state as shown in FIG. 2A, to a curved shape which is curved in substantially an arc state in an up-and-down or right-to-left direction as shown in FIG. 1.

Further, while the curvable portion 9 of the endoscope is not being curved, that is, the entire curvable portion 9 is maintained in a standard shape which is drawn in substantially a linear state, gap portions 21 having a V-letter shape between the end edge portions of adjacent pair of curvable pieces 18 are held at the same intervals in all directions, that is, up, down, right and left directions, of each angle wire 23. With this structure, in order to curve the curvable portion 9, as the leading end curvable piece 18A is pulled to the hand side by means of the angle wires 23 which is pulled, each curvable piece 18 is pivoted around the pivotal pin 20 so as to narrow the V-shaped gap portions 21 between the end edge portions of the curvable pieces 18 on a side of the direction in which the angle wires 23 are pulled, whereas to widen the gap portions 21 on the opposite side. Thus, the entire curvable portion 9 is curved in substantially an arc shape. Further, by the curving operation of the curvable portion 9, it can be curved to form an arbitrarily curved shape between the standard shape which is drawn in substantially a linear state and a maximum curved shape which is curved in an arc state. It should be noted here that when the curvable portion 9 is curved at maximum, the V-shaped gap portions 21 between the end edge portions of adjacent pairs of the curvable pieces 18 are narrowed such that the end edge portions of each adjacent pair of front one and next curvable pieces abut against each other.

As shown in FIG. 4, in the insertion portion 6 of the endoscope 2, the shape detection probe 28 for detecting the shape of the insertion portion 6 is built together with the contents such as four angle wires 23a1, 23a2, 23b1 and 23b2 arranged in all of up, down, right and left directions, two light guide fibers 24, an image signal transmission cable 25 for the imaging means such as the CCD 39, a gas/water supply channel 26 and a treatment tool through channel 27. Here, tip end portions of the two light guide fibers 24 are arranged to oppose to each other in inner surface sides of two illumination window portions provided in the distal end structure portion 10, and their proximal end portions are extended through the operation portion 7 and the universal cord 11, into the connector 12. Further, illumination light from the light source device 3 is allowed to enter the light guide fibers 24 via the connector 12. Further, the illumination light transmitted from the light guide fibers 24 are emitted to the outside in an expanding fashion by the illumination window portion.

Figure 3:
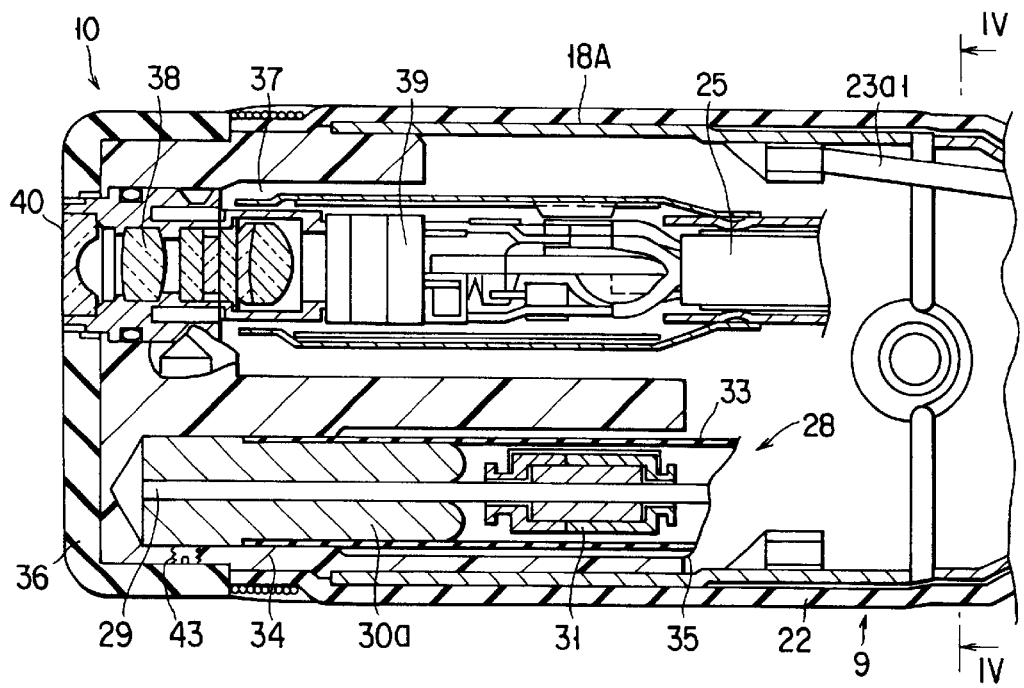
FIG. 3 is a longitudinal sectional view showing a fixation state of a distal end of the shape detection probe in the endoscope according to the first embodiment.

The proximal end portion side of the image signal transfer cable 25 extends from the inside of the operation portion 7, and it is connected to the control device 15 via the inside of the universal cord 11, the inside of the connector 12 and the connection cable 13. In an observation with the endoscope, an observed image within a view range is transmitted as shown in FIG. 3 from an observation window 40 to an objective lens 38, and with the objective lens 38, the observed image is formed in the imaging means such as the CCD 39. Further, the observed image is converted into an electrical signal by the imaging means such as the CCD 39, and then transmitted to the control device 15 by the image signal transmission cable 25 via a CCD connector 13a of the connection cable 13.

In the meantime, a distal end portion of the gas/water supply channel 26 is connected to a gas/water supply nozzle, though it is not shown in the figure, provided in the distal end structure portion 10, whereas a proximal end portion thereof extends through the insides of the operation portion 7 and the universal cord 11, into the connector 12. Further, the distal end portion of the treatment tool through channel 27 is attached to the distal end opening section (not shown) of the treatment tool through channel 27 provided in the distal end structure portion 10, whereas a proximal end portion thereof is attached to a treatment tool insertion portion provided in the operation portion 7.

The shape detection probe 28 of this embodiment is provided within the insertion portion 6 of the endoscope 2 substantially over its entire length. FIG. 2B shows the internal structure of the shape detection probe 28 in this embodiment. As can be seen in FIG. 2B, a core wire 29 is provided in the shape detection probe 28 at a position of its axial center. A tip end member 30a is fixed to a tip end portion of the core wire 29, and a rear end member 30b is fixed to a rear end portion thereof.

Further, a plurality of magnetic field generating coils 31 each generating a magnetic field are fixed onto the surrounding of the core wire 29 at predetermined intervals with an adhesive or the like. It should be noted here that a plurality of coils 31 of the shape detection probe 28 are arranged at substantially equal intervals over the substantially entire length of the insertion portion 6 of the endoscope 2.

Two signal wires 32 are connected to each coil 31. An armor tube 33 for the protection of each coil 31 and the signal wires 32 is mounted on an outer circumference of the shape detection probe 28. The armor tube 33 is an elastic tube made of, for example, silicon rubber. A filler 42 prepared by mixing silicon and a solvent is packed into the armor tube 33 to fill the gaps between the contents therein, such as the core wire 29, the coils 31 and signal wires 32.

Further, the distal end portion of the shape detection probe 28 is fixed to a main body 34 of the distal end structure portion 10 as shown in FIG. 3. Here, the main body 34 of the distal end structure portion is made of a non-metal material which does not weaken the intensity of the magnetic field from the coil 31 of the shape detection probe 28, for example, a non-magnetic material such as plastic.

In a rear end surface of the distal end structure portion main body 34, a shape detection probe mount hole 35 having substantially a circular shape, is made. While being inserted in the shape detection probe mount hole 35 of the distal end structure portion main body 34, the tip end member 30a of the shape detection probe 28 is fixed therein by means of a fixation screw 43. It should be noted that a distal end cover 36 for covering the entire outer surface of the distal end structure portion main body 34 is provided on the distal end structure portion 10.

Further, in this embodiment, as shown in FIG. 2A, three magnetic field generating coils 31A, 31B and 31C on the distal end side of the shape detection probe 28 are provided in the curvable portion 9. Here, the first coil 31A at the leading end position is disposed at a position corresponding to the leading end curvable piece 18A located at the leading end position of the curvable portion 9, whereas the third coil 31C is disposed at a position corresponding to the trailing end curvable piece 18B located at the trailing end position of the curvable portion 9. Further, the second coil 31B is disposed at an intermediate position (approximately at center) between the leading end curvable piece 18A and the trailing end curvable piece 18C.

In the endoscope 2 of this embodiment, the magnetic field generated from each magnetic field generating coil 31 of the shape detection probe 28 is detected by the antenna 17. An output signal from the antenna 17 is input to the shape detecting control device 16, so as to detect the shape of the insertion portion 6, and the detected shape of the insertion portion 6 is displayed on a second monitor 5 provided exclusively for that purpose. On the screen of the second monitor 5, the positions where the coils 31 are detected on the basis of the magnetic fields generated from those magnetic field generating coils 31 of the shape detection probe 28 are displayed in the form of dot. Then, as the dots of the detection positions of the coils 31 are connected, the shape of the insertion portion 6 can be displayed on the screen of the second monitor 5 in the form of pseudo-image.

Next, the operation of the above-described structure will now be described. When the endoscope 2 of this embodiment is used, the insertion portion 6 of the endoscope 2 is inserted to a pipe path used for an industrial purpose, or to a tube canal to be examined by the endoscope, such as a cavity of a body canal. In order to insert the insertion portion 6 of the endoscope 2 into a cavity, the operation knob of the operation portion 7 is operated to follow the shape of the cavity in which the portion 6 is inserted. Here, as the knob of the operation portion 7 is operated, any one or two angle wires 23 are pulled, and with these angle wires 23 operated, the curvable portion 9 is curved.

In the case where the distal end structure portion 10 of the endoscope 2 is inserted to, for example, a deep part of the large intestine through curved sections of the body cavity, or it is inserted to a deep portion of a pipe path for an industrial use, the insertion portion 6 is further inserted while the curvable portion 9 is curved to follow the shape of the cavity in which the portion is inserted. As the insertion portion 6 is inserted, the flexible tube portion 8 is deformed in accordance with the shape of the insertion tube path.

Further, in the embodiment, during the insertion operation of the insertion portion 6 of the endoscope 2, the magnetic fields generated from the coils 31 of the shape detection probe 28 are detected by the antenna 17. The output signal from the antenna 17 is input to the shape detection control device 16, so as to detect the shape of the insertion portion 6, and the detected shape of the insertion portion 6 is displayed on the second monitor 5 for the exclusive purpose. Here, on the screen of the second monitor 5, the positions where the coils 31 are detected on the basis of the magnetic fields generated from those magnetic field generating coils 31 of the shape detection probe 28 are displayed in the form of dot. Then, as the dots of the detection positions of the coils 31 are connected, the entire shape of the insertion portion 6 can be displayed on the screen of the second monitor 5 in the form of pseudo-image.

In the embodiment, a curved shape of the curvable portion 9 of the endoscope 2, can be detected with the antenna 17 by monitoring the magnetic fields generated from three coils 31A, 31B and 31C on the distal end side of the shape detection probe 28. Here, on the screen of the second monitor 5, the positions where the three coils 31A, 31B and 31C are detected, are displayed in the form of dot. Then, as the dots of the detection positions of the three coils 31A, 31B and 31C are connected together, the shape of the curvable portion 9 can be displayed on the screen of the second monitor 5 in the form of pseudo-image.

With the above-described structure, the following effect can be obtained. That is, in the embodiment, the three magnetic field generating coils 31A, 31B and 31C on the distal end side of the shape detection probe 28 are arranged in the curvable portion 9 of the endoscope 2. Here, the first coil 31A at the leading end position is disposed at a position corresponding to the leading end curvable piece 18A of the curvable portion 9, and the third coil 31C is disposed at a position corresponding to the trailing end curvable piece 18B of the curvable portion 9. Further, the second coil 31B is disposed at an intermediate position (approximately at center) between the leading end curvable piece 18A and the trailing end curvable piece 18C. In the curving operation of the curvable portion 9, the position of the leading end curvable piece 18A of the curvable portion 9 is detected with the first coil 31A of the shape detection probe 28, and the position of the trailing end curvable piece 18B of the curvable portion 9 is detected with the third coil 31C of the shape detection probe 28. Further, the intermediate position between both the leading and trailing ends of the curvable portion 9 is detected with the second coil 31B. With this structure, as these three detected points are connected smoothly, the curvature shape of the curved portion 9 is detected substantially accurately. Therefore, the shape detection accuracy for the curvable portion 9 can be effectively improved without providing a particularly great number of coils 31 of the shape detection probe 28.

Further, in this embodiment, it is not necessary to prepare a particularly great number of coils 31 of the shape detection probe 28 provided in the curvable portion 9, and therefore an increase in the cost of the shape detection probe 28 can be prevented. Therefore, the production cost of the entire system of the endoscope device 1 can be decreased.

Apart from the above, in this embodiment, the main body 34 of the distal end structure portion of the endoscope 2 is made of a non-metal material which does not weaken the intensity of the magnetic filed output from a coil 31 of the shape detection probe 28, that is, for example, a plastic material. With this structure, the distal end structure portion 10 of the endoscope 2 to which the shape detection probe 28 is fixed, does not become to have a ground potential. Therefore, the tip end of the probe 28 is not shielded with the ground potential, or an electromagnetic wave output from the first coil 31A of the shape detection probe 28 is not weakened; therefore the electromagnetic wave output performance of the tip end of the shape detection probe 28 can be improved, thereby achieving a high-performance shape detection probe 28.

Figure 5:
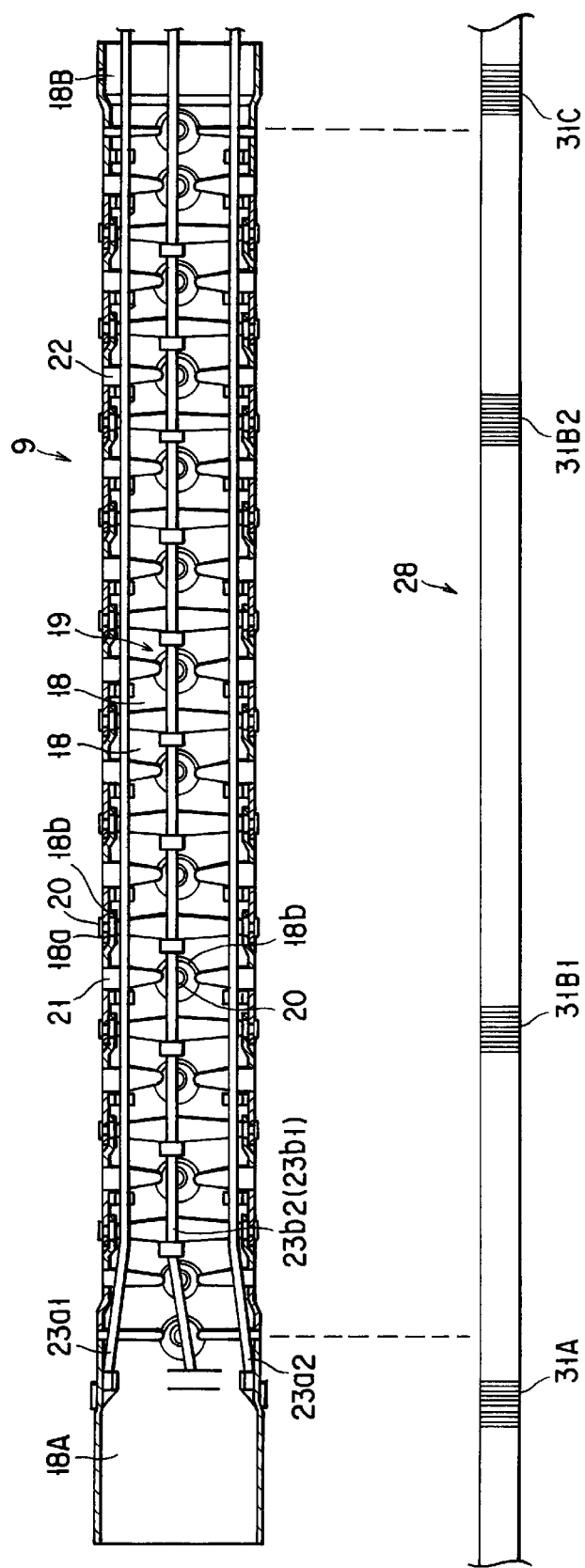
FIG. 5 is a diagram showing the relationship between the position of a curvable portion and the arrangement of coils of the shape detection probe built in the curvable portion, in the endoscope of the second embodiment.

FIG. 5 shows the second embodiment of the present invention. In this embodiment, the structure of the shape detection probe 28 provided in the curvable portion 9 of the first embodiment (see FIGS. 1 to 4) is remodeled as will now be described. It should be noted that the sections other than the above-mentioned structure are the same as those of the first embodiment. Here, the same structural elements as those of the first embodiment will be designated by the same reference numerals, and the explanations therefor will not be repeated.

More specifically, the first embodiment has a structure in which three magnetic field generating coils 31A, 31B and 31C are provided in the curvable portion 9, whereas in this embodiment, there are four magnetic field generating coils provided in the curvable portion 9. Here, a first coil 31A at the leading end position is disposed at a position corresponding to a leading end curvable piece 18A located at the leading end position of the curvable portion 9, whereas a fourth coil 31C is disposed at a position corresponding to a trailing end curvable piece 18B located at the trailing end position of the curvable portion 9. Further, the rest of two coils 31B1 and 31B2 are disposed at intermediate positions appropriately dispersedly between the leading end curvable piece 18A and the trailing end curvable piece 18B.

As described above, in this embodiment, two coils 31B1 and 31B2 are provided in a section of the curvable portion 9, where the deformation amount of the curvature is large, such as an intermediate portion between the leading end curvable piece 18A and the trailing end curvable piece 18B of the curvable portion 9. With this structure, if one of the two coils 31B1 and 31B2, that is, the coil 31B1 (or 31B2) becomes out of order, the detected points of the other coil 31B2 (or 31B1) and the leading and trailing end coils 31A and 31C, are connected. In this manner, the shape of the curvable portion 9 can be displayed on the screen of the second monitor 5 in the form of pseudo-image, and therefore the durability of the shape detection probe 28 can be improved.

Figure 6:
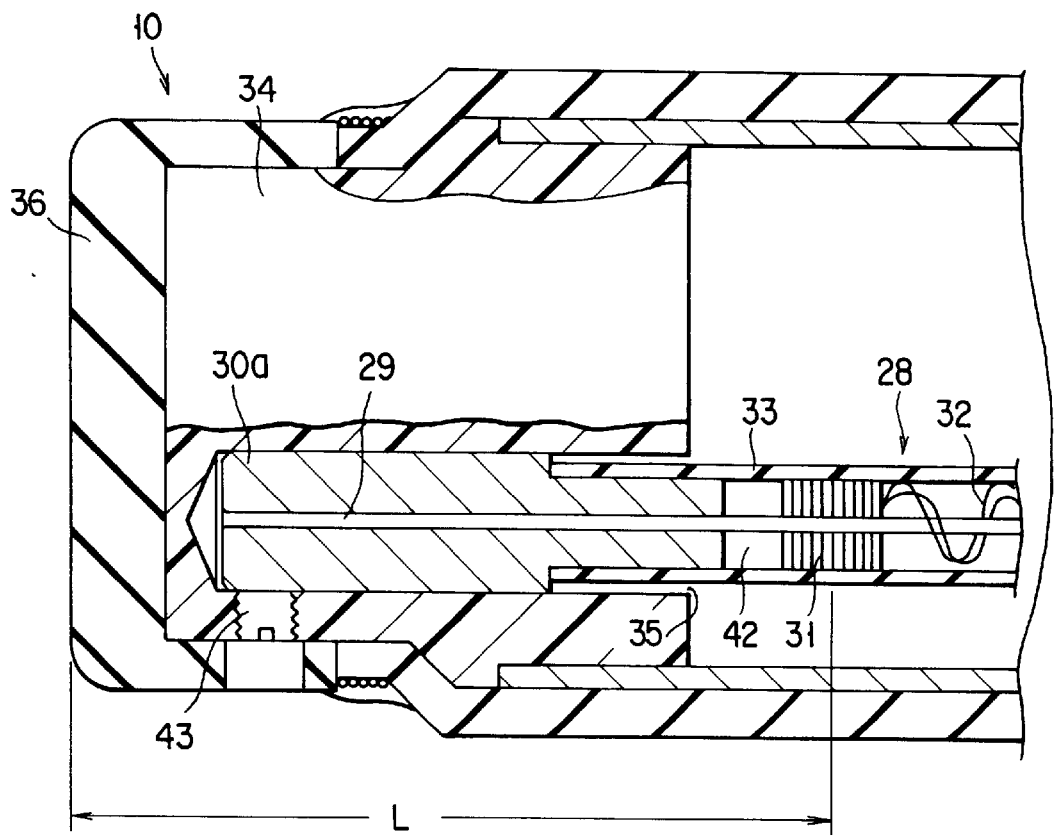
FIG. 6 is a longitudinal sectional view showing a fixation state of a distal end of the shape detection probe in the endoscope according to the third embodiment.
Figure 7:
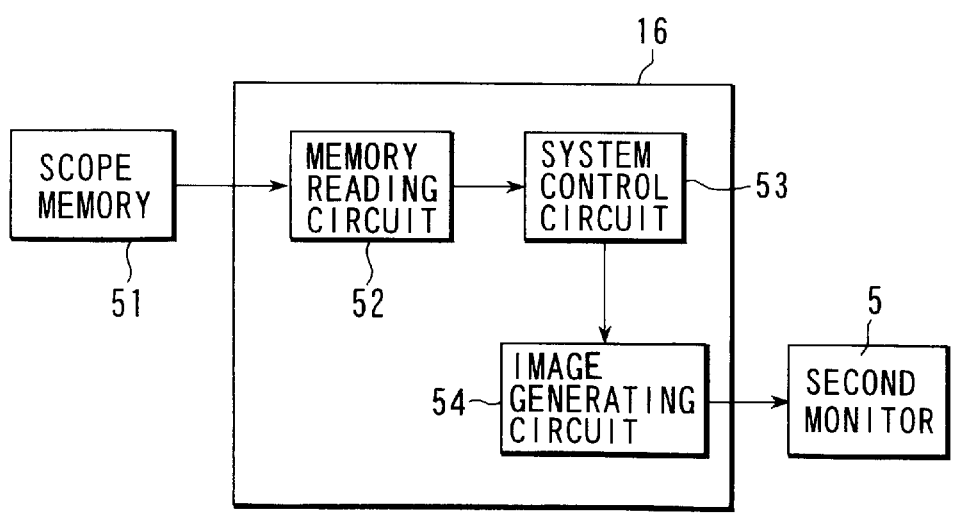
FIG. 7 is a schematic structural diagram showing distal end shape correction means of the shape detection probe in the endoscope according to the third embodiment.

FIGS. 6 and 7 shows the third embodiment of the present invention. In this embodiment, a scope memory 51 such as shown in FIG. 7 is built in a part of the endoscope 2 of the first embodiment (see FIGS. 1 to 4), for example, the connector 12. The memory 51 stores correction data for the shape of a distal end of the insertion portion shape detection probe 28 built in the endoscope 2, obtained by converting a distance L between the magnetic field generating coil 31 at the leading end position and the end surface of the distal end structure portion 10 in the insertion portion 6 of the endoscope 2, as shown in FIG. 6.

In the shape detection control device 16, a memory reading circuit 52, a system control circuit (distal end shape correction means) 53 and an image generating circuit 54 are provided. Here, the scope memory 51 of the endoscope 2 is connected to the memory reading circuit 52. Further, the second monitor 5 is connected to the image generating circuit 54.

Further, when the endoscope 2 is in use, an image signal which indicates the shape of the insertion portion 6 is formed in the shape detecting control device 16, on the basis of the detection data from the insertion portion shape detection probe 28. Here, the correction data for the distal end shape, obtained by converting the distance L between the magnetic field generating coil 31 at the leading end position in the insertion portion shape detection probe 28 and the end surface of the distal end structure portion 10 in the insertion portion 6 of the endoscope 2, is sent from the scope memory 51 of the endoscope 2 to the memory reading circuit 52 of the shape detecting control device 16. Further, the output signal from the memory reading circuit 52 is input to the system control circuit 53. A control signal obtained by adding the correction data of the distal end shape of the insertion portion 6 to the detection data from the insertion portion shape detection probe 28, is output from the system control circuit 53, to the image generation circuit 54. An image signal obtained by adding the correction data of the distal end shape of the insertion portion 6 to the detection data from the insertion portion shape detection probe 28 is output from the image generation circuit 54 to the second monitor 5. In this manner, an image of the shape of the insertion portion 6, obtained by adding the correction data of the distal end shape of the insertion portion 6 to the detection data from the insertion portion shape detection probe 28 (that is, the shape data of the insertion portion 6) is displayed on the second monitor 5.

With the above-described structure, the following advantage can be obtained. That is, in this embodiment, the scope memory 51 is built in the connector 12 of the endoscope 2, and the correction data for the distal end shape, obtained by converting the distance L between the magnetic field generating coil 31 at the leading end position in the insertion portion shape detection probe 28 built in the endoscope 2 and the end surface of the distal end structure portion 10 in the insertion portion 6 of the endoscope 2, is stored in the memory 51. Further, the memory reading circuit 52, the system control circuit 53 and the image generating circuit 54 are provided in the shape detecting control device 16, and thus the image of the shape of the insertion portion 6, obtained by adding the correction data of the distal end shape of the insertion portion 6 to the detection data from the insertion portion shape detection probe 28 (that is, the shape data of the insertion portion 6) is displayed on the second monitor 5. With this structure, even if the position of the magnetic field generating coil 31 located at the leading end position of the insertion portion shape detection probe 28 built in the endoscope 2 does not coincide the position of the end surface of the distal end structure portion 10 in the insertion portion 6 of the endoscope 2, the shape of the insertion portion 6 can be displayed on the second monitor 5 while the position of the magnetic field generating coil 31 at the leading end position in the insertion portion shape detection probe 28 and the position of the end surface of the distal end structure portion 10 in the insertion portion 6 of the endoscope 2, are made to coincide with each other. Consequently, the accuracy of the shape of the insertion portion 6 of the endoscope 2, displayed on the second monitor 5, can be enhanced, and therefore the insertion property of the endoscope 2 can be improved.

Further, the scope memory 51 is built in the connector 12 of the endoscope 2, and the correction data for the distal end shape, obtained by converting the distance L between the magnetic field generating coil 31 at the leading end position in the insertion portion shape detection probe 28 built in the endoscope 2 and the end surface of the distal end structure portion 10 in the insertion portion 6 of the endoscope 2, is stored in the memory 51. With this structure, for a variety of types of endoscopes 2, it is possible to store correction data of a distal end shape which is unique to a respective type (the data of the distance obtained by a converting operation corresponding to the type of the endoscope), in the corresponding memory 51. Consequently, even if the distance L between the magnetic field generating coil 31 at the leading end position in the insertion portion shape detection probe 28 built in the endoscope 2 and the end surface of the distal end structure portion 10 in the insertion portion 6 of the endoscope 2, differs from one type of an endoscope to another, the correction data of the distal end shape, which is unique to that particular type can be read out from the memory 51. With this structure, in the case where endoscopes 2 of different types are used, the position of the end surface of the distal end structure portion 10 in the insertion portion 6 of the endoscope can be accurately displayed on the second monitor 5. As a result, the accuracy of the shape of the insertion portion 6 of the endoscope 2 displayed on the second monitor 5 can be increased. As a result, it becomes possible to easily and accurately determine how the endoscope 2 is handled while conducting an examination, and thus the improvement of the insertion property in the operation can be achieved.

Figure 8A:
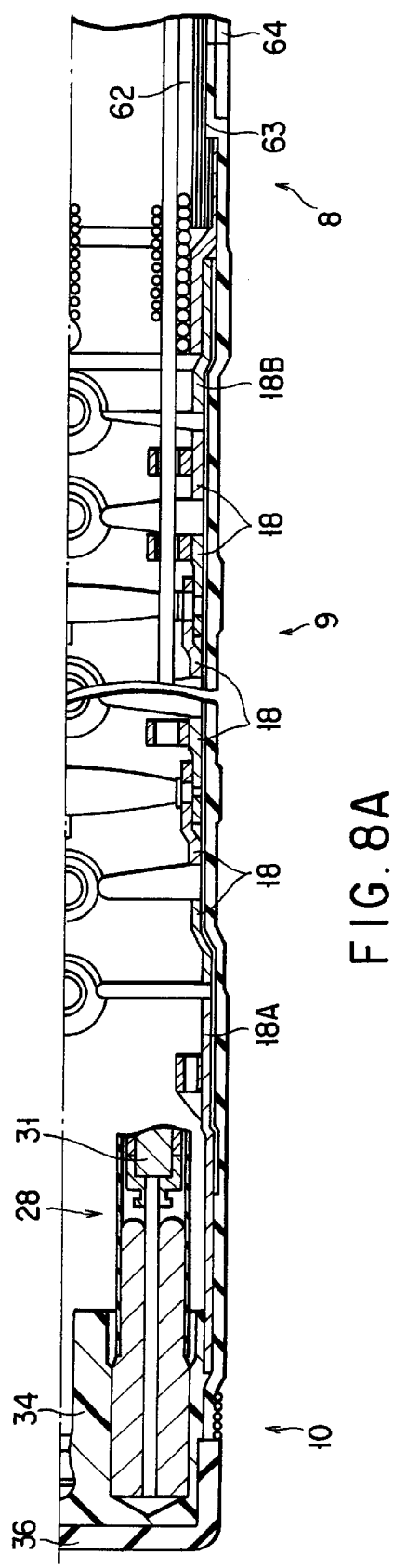
FIG. 8A is a longitudinal sectional view showing a schematic structure of the distal end portion of the insertion portion in the endoscope according to the fourth embodiment.
Figure 8C:
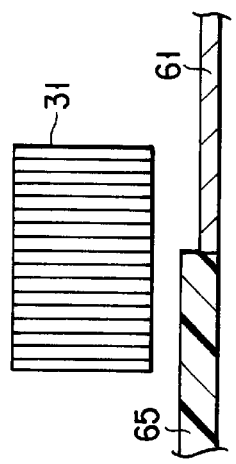
FIG. 8C is a longitudinal sectional view showing a main portion, designed to illustrate a state in which a plurality of structural members having different influences on magnetic fields are arranged to surround the coils of the shape detection probe.
Figure 8B:
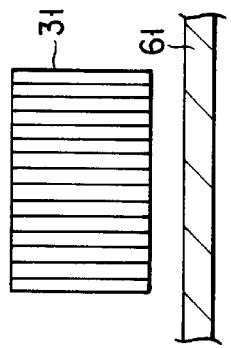
FIG. 8B is a longitudinal sectional view showing a main portion, designed to illustrate the coil arrangement state of the shape detection probe.

FIGS. 8A and 8B show the fourth embodiment of the present invention. In this embodiment, the circumference of each coil 31 in the insertion portion shape detection probe 28 is covered uniformly by a thin metal member 61 having substantially a cylinder shape. Here, in the surrounding of each coil 31 in the shape detection probe 28 disposed in the curvable portion 9, a curvable piece 18 is arranged. In this embodiment, the curvable piece 18 surrounding each coil 31 in the shape detection probe 28 disposed in the curvable portion 9 is uniformly formed of a thin metal member 61. Thus, as can be seen in FIG. 8B, each coil 31 is covered uniformly by a thin metal member 61 having substantially a cylindrical shape.

Further, a spiral tube (flex) 62 formed by winding a thin-plate metal band is provided at an innermost circumference side of the flexible tube portion 8, and a blade 63 of a net tube made of a metal or resin, is mounted on the outer circumference of the flex 62. Further, a resin tube 64 made of a plastic material having a flexibility is mounted on the outer circumference of the blade 63. Further, metal members such as the flex 62 and blade 63 are provided as a cover to surround each coil 31 in the shape detection probe 28 disposed in the flexible tube portion 8. In this embodiment, the metal members such as the flex 62 and blade 63 provided to surround each coil 31 in the shape detection probe 28 disposed in the flexible tube portion 8 are formed uniformly of a thin metal material. Thus, each coil 31 is surrounded uniformly by a thin metal member having substantially a cylindrical shape.

In the embodiment, not only that the curvable piece 18 which surrounds each coil 31 in the shape detection probe 28 disposed in the curvable portion 9 is uniformly formed of a thin metal member 61, but also that the metal members such as the flex 62 and blade 63, to surround each coil 31 in the shape detection probe 28 disposed in the flexible tube portion 8, are similarly formed uniformly of a thin metal member, and therefore the surrounding of each coil 31 can be covered uniformly by the thin metal member 61 having substantially a cylindrical shape, as can be seen in FIG. 8B. With this structure, it is possible to make the magnetic field generated from each coil 31 radiated uniformly from its entire body of each coil 31, as compared to such a case as shown in, for example, FIG. 8C, where the metal members 61 and plastic material parts 65 are mixedly arranged around each coil 31, with which the magnetic field generated from each coil 31 is radiated non-uniformly. As a result, in the present invention, the accuracy of the shape detected by the shape detection probe 28 is further improved, and therefore the insertion property in the operation of the endoscope 2 can be improved.

Figure 9:
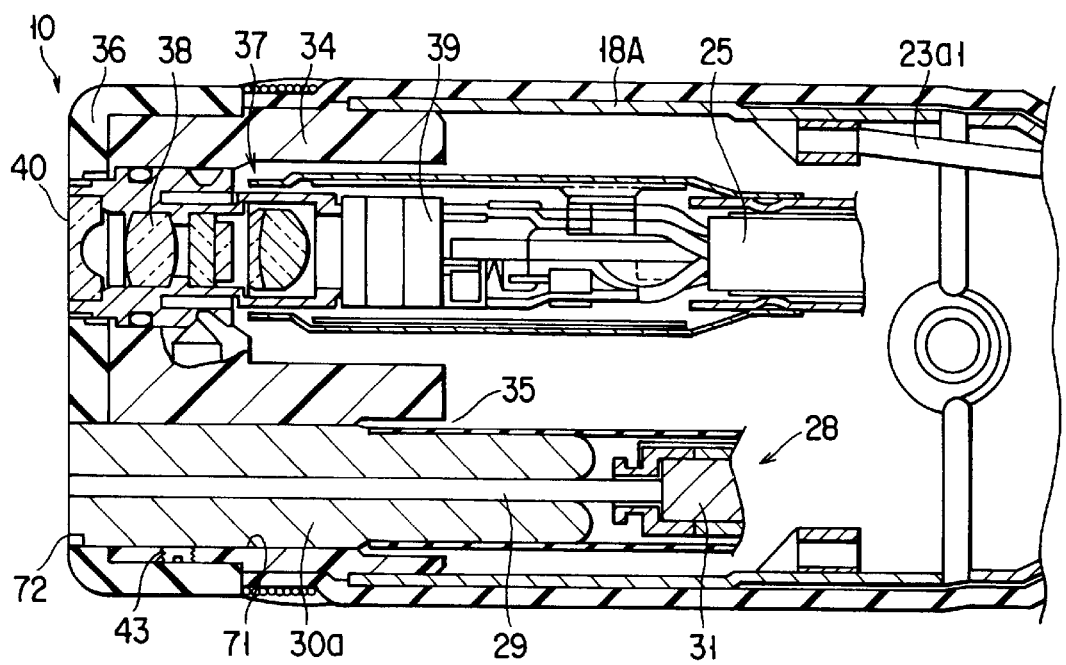
FIG. 9 is a longitudinal sectional view showing a fixation state of a distal end of the shape detection probe in the endoscope according to the fifth embodiment.

FIG. 9 shows the fifth embodiment of the present invention. This embodiment is a remodeled version of the first embodiment (see FIGS. 1 to 4), where the structure of the distal end structure portion 10 in the endoscope 2 is changed as will now be described.

That is, in this embodiment, a through hole 71 is made in the main portion 34 of the distal end structural portion 10, in the form of the end section of the shape detection probe mount hole 35, which is made through to the end surface of the main portion 34 of the distal end structural portion 10. Further, a communication hole 72 which communicates to the through hole 71 of the main body 34 of the distal end structural portion. The distal end of the insertion portion shape detection probe 28 is extended from the through hole 71 of the main body 34 of the distal end structural portion, to the communication hole 72 of the distal end cover 36. Thus, the distal end of the insertion portion shape detection probe 28 is located at the same position as the end surface of the distal end structure portion 10 of the endoscope 2.

In this embodiment, when the insertion portion shape detection probe 28 becomes out of order due to the disconnection of a wire or the like and it is to be replaced, the detection probe 28 is pushed back from the distal end side to the operation portion 7 side while the fixation screw 43 is loosened, and the detection probe 28 is extracted from the operation portion 7 side. Thus, the detection probe 28 can be removed from the endoscope 2.

Alternatively, in order to extract the insertion portion shape detection probe 28, it is possible to form a structure in which a guide member such as a wire is provided at the distal end portion of the detection probe 28. With such a structure, during the operation of extracting the detection probe 28 from the operation portion 7 side, the guide member such as a wire can be drawn into the insertion portion 6 of the endoscope 2. Then, while the distal end of an insertion portion shape detection probe 28 for the replacement is being mounted on the guide member, the guide member is pulled up to the distal end side, so as to draw the detection probe 28 for the replacement into the insertion portion 6 of the endoscope 2. Further, the distal end of the detection probe 28 is extended from the through hole 71 of the main body 34 of the distal end structure portion to the communication hole 72 of the distal end cover 36, and the fixation screw 43 is fastened while the distal end of the detection probe 28 is disposed at the same position as the end surface of the distal end structure portion 10 of the endoscope 2. Thus, the detection probe 28 for the replacement can be built in the insertion portion 6 of the endoscope 2, to restore the original structure.

With the above-described structure, the following effect can be obtained. That is, in the embodiment, the distal end of the insertion portion shape detection probe 28 is located at the same position as the end surface of the distal end structure portion 10 of the endoscope 2. With this structure, when the insertion portion shape detection probe 28 is to be replaced, the detection probe 28 is pushed back from the distal end side to the rear side while the fixation screw 43 is loosened. Thus, it is not necessary to carry out a laborious operation in order to replace the shape detection probe 28 with a new one, such as disassembling the entire insertion portion 6 of the endoscope 2 or extracting the shape detection probe 28 from the operation portion 7 side, unlike in the case of the first embodiment, where the distal end of the shape detection probe 28 is inserted to the shape detection probe mount hole 35 which is a dig-in hole made in the main body 34 of the distal end structure portion 10, and the distal end portion of the shape detection probe 28 is fixed in the probe mount hole 35 while it is dug therein. Thus, with this embodiment, the shape detection probe 28 can be replaced easily as compared to the first embodiment, and therefore the repairability of the endoscope 2 in which the shape detection probe 28 is built, can be improved.

Figure 10:
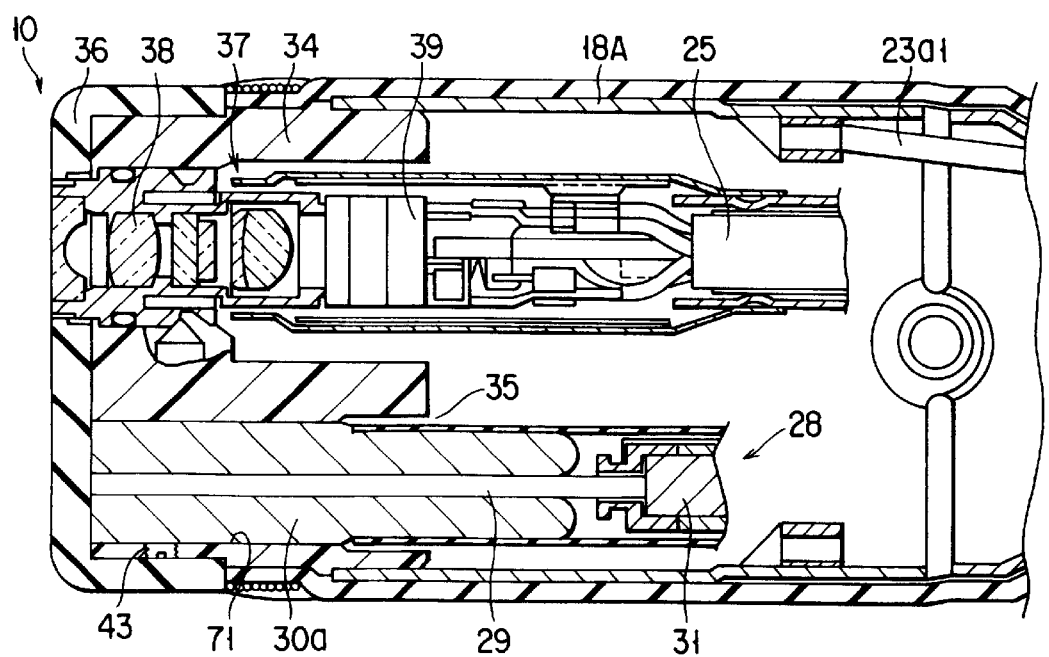
FIG. 10 is a longitudinal sectional view showing a fixation state of a distal end of the shape detection probe in the endoscope according to the sixth embodiment.

FIG. 10 shows the sixth embodiment of the present invention. This embodiment is a remodeled version of the fifth embodiment (see FIG. 9), where the structure of the distal end structure portion 10 in the endoscope 2 is changed as will now be described.

That is, in this embodiment, a through hole 71 is made in the main portion 34 of the distal end structural portion 10, in the form of the end section of the shape detection probe mount hole 35, which is made through to the end surface of the main portion 34 of the distal end structural portion 10. Further, a communication hole 72 of the distal end cover 36 is omitted. The distal end of the insertion portion shape detection probe 28 is extended to the through hole 71 of the main body 34 of the distal end structural portion 10, pressed the distal end cover 36. Thus, the distal end of the insertion portion shape detection probe 28 is located at the same position as the end surface of the main portion 34 of the distal end structure portion 10 of the endoscope 2.

In this embodiment, when the insertion portion shape detection probe 28 becomes out of order due to the disconnection of a wire or the like and it is to be replaced, the distal end cover 36 is removed to expose the distal end of the shape detection probe 28. In this state, the fixation screw 43 is loosened, and the shape detection probe 28 is pushed back from the distal end side to the operation portion 7 side, thus extracting the detection probe 28 from the operation portion 7 side. In this manner, the detection probe 28 can be removed from the endoscope 2.

Alternatively, in order to extract the insertion portion shape detection probe 28, it is possible to form a structure in which a guide member such as a wire is provided at the distal end portion of the detection probe 28. With such a structure, during the operation of extracting the detection probe 28 from the operation portion 7 side, the guide member such as a wire can be drawn into the insertion portion 6 of the endoscope 2. Then, while the distal end of an insertion portion shape detection probe 28 for the replacement is being mounted on the guide member, the guide member is pulled up to the distal end side, so as to draw the detection probe 28 for the replacement into the insertion portion 6 of the endoscope 2. Further, the distal end of the detection probe 28 is extended to the through hole 71 of the main body 34 of the distal end structure portion 10, pressed the distal end cover 36, and the fixation screw 43 is fastened while the distal end of the detection probe 28 is disposed at the same position as the end surface of the main portion 34 of the distal end structure portion 10 of the endoscope 2. Then, in this state, as the distal end cover 36 is mounted on the main body 34 of the distal end structure portion 10, the detection probe 28 for the replacement can be built in the insertion portion 6 of the endoscope 2, to restore the original structure.

With the above-described structure, the following effect can be obtained. That is, in the embodiment, the distal end of the insertion portion shape detection probe 28 is extended to the position of the ending section of the through hole 71 of the main body 34 of the distal end structure portion, and the distal end of the probe is fixed while it is pressed the distal end cover 36. With this structure, when the insertion portion shape detection probe 28 is to be replaced, the distal end cover 36 is removed, and the fixation screw 43 is loosened while the distal end portion of the shape detection probe 28 is exposed. Then, the detection probe 28 is pushed back from the distal end side to the rear side. Thus, it is not necessary to carry out a laborious operation in order to replace the shape detection probe 28 with a new one, such as disassembling the entire insertion portion 6 of the endoscope 2 or extracting the shape detection probe 28 from the operation portion 7 side, unlike in the case of the first embodiment, where the distal end of the shape detection probe 28 is inserted to the shape detection probe mount hole 35 which is a dig-in hole made in the main body 34 of the distal end structure portion 10, and the distal end portion of the shape detection probe 28 is fixed in the probe mount hole 35 while it is dug therein. Thus, with this embodiment, the shape detection probe 28 can be replaced easily as compared to the first embodiment, and therefore the repairability of the endoscope 2 in which the shape detection probe 28 is built, can be improved.

Figure 11:
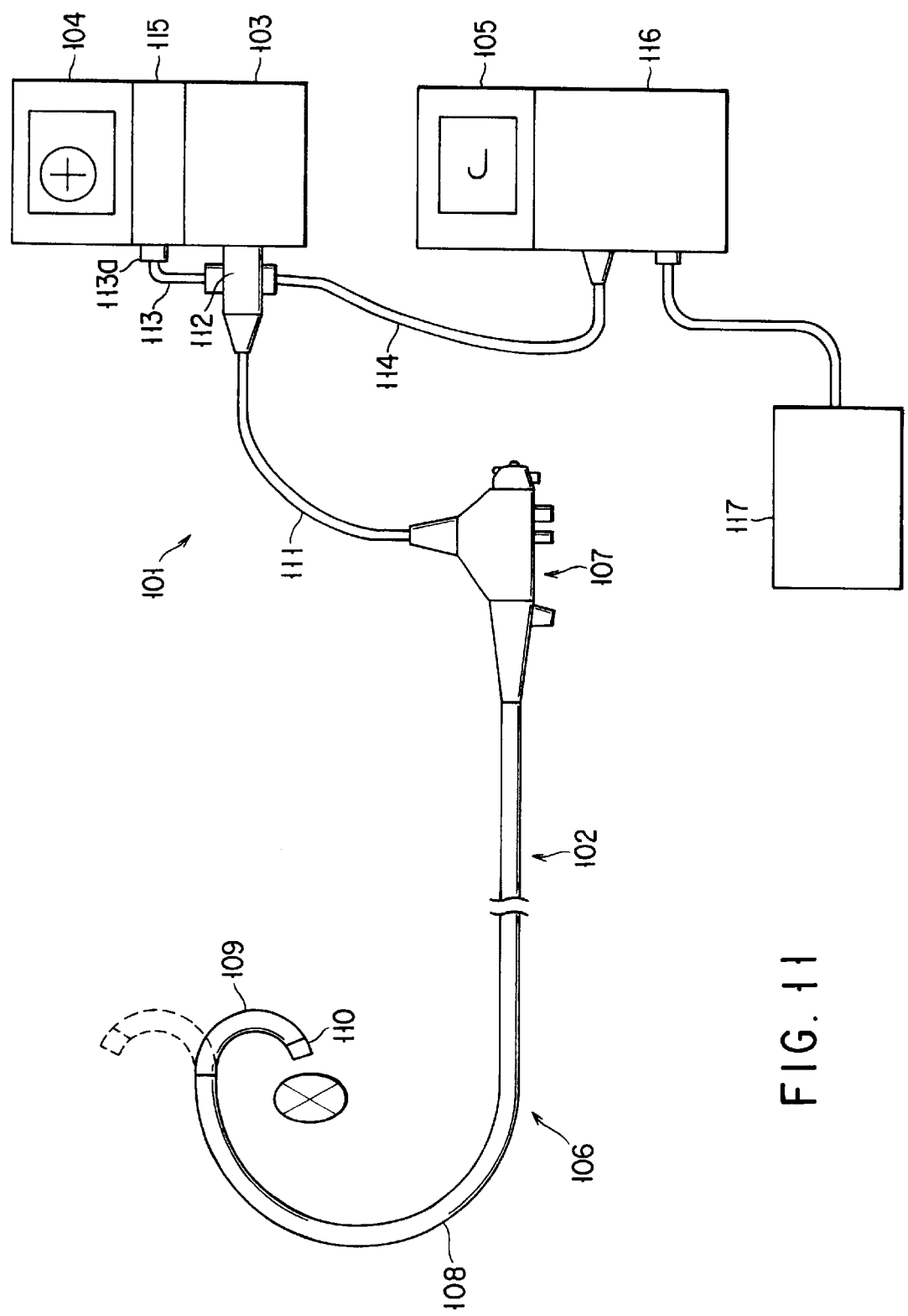
FIG. 11 is a schematic structural diagram showing an entire endoscope device according to the seventh embodiment of the present invention.

FIGS. 11 to 16 show the seventh embodiment of the present invention. FIG. 11 illustrates a brief structure of the entire structure of an endoscope device 101 of this embodiment. The endoscope device 101 of this embodiment includes an endoscope 102, a light source device 103, a first monitor 104 for displaying an image of the endoscope, and a second monitor 105 for displaying a shape of the endoscope 102.

In the endoscope 102 of this embodiment, a hand-side operation portion 107 is provided in a proximal portion of a slender insertion portion 106 to be inserted into a cavity of a canal. Here, in the insertion portion 106, a deformable curvable portion 109 is provided in a distal end portion of a slender flexible portion 108 thereof. Further, a hard distal end structure portion 110 is jointed to the distal end portion of the curvable portion 109. In the distal end structure portion 110, not only a light guide fiber 124 serving as a illumination optical system, an objective lens serving as an observation optical system, and imaging means such as a CCD, but also an air/water supply nozzle, a treatment tool through channel 127 and the like are built.

Further, a curving operating portion such as a curving knob, for operating the curvable portion 109 to curve, is provided in the operation portion 107 on the hand side of the endoscope 102, and one end of the universal cord 111 is connected to the operation portion 107. A connector 112 is mounted to another end of the universal cord 111. The connector 112 is detachably connected to the light source device 103.

Further, one end of each of two connection cables 113 and 114 is coupled to the connector 112. Here, one connection cable 113 is connected to the control device 115 such as a camera control unit (CCU). The first monitor 104 is connected to the control device 115.

The other connection cable 114 is connected to a shape detecting control device (insertion portion shape detecting means) 116 serving to detect the shape of the insertion portion 106 of the endoscope 102. To the shape detecting control device 116, an antenna 117 and a second monitor 105 are connected.

Figure 12A:
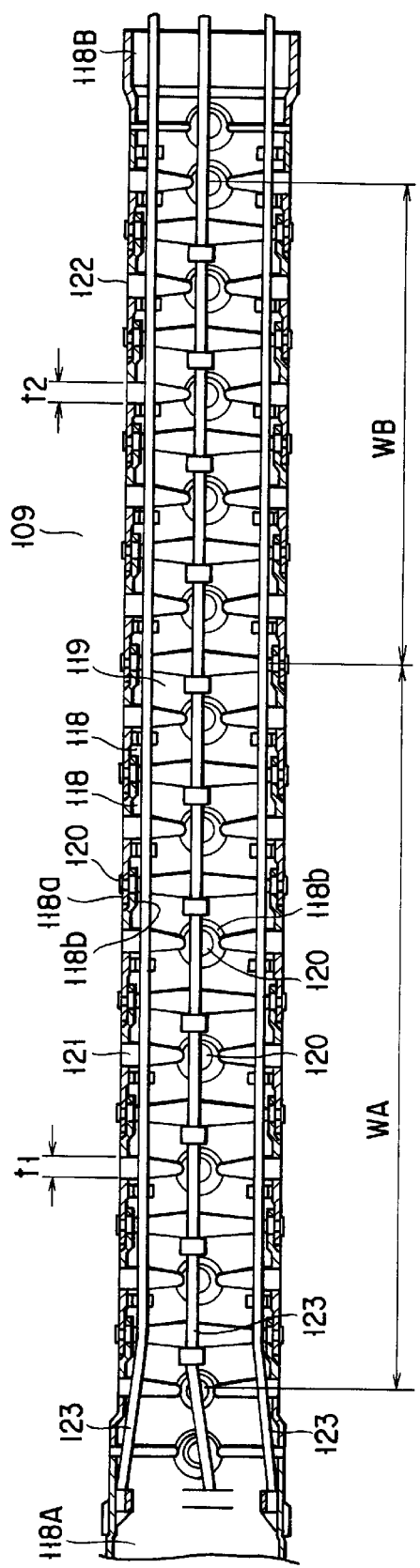
FIG. 12A is a longitudinal sectional view showing an internal structure of a curvable portion in the endoscope according to the seventh embodiment.

FIG. 12A illustrates an internal structure of the curvable portion 109 of the endoscope 102. In the curvable portion 109 of this embodiment, a curvable piece group 119 in which a plurality of ring-like curvable pieces 118 are arranged side by side in the axial direction of the insertion portion 106 is provided. Here, two front end side projecting portions 118a are set in a front end portion of each curvable piece 118 to project forwards. The two front end side projecting portions 118a are arranged at positions which are 180 degrees away from each other in the circumferential direction of the ring of each curvable piece 118.

Further, two rear end side projecting portions 118b are set in a rear end portion of each curvable piece 118 to project backwards. The two rear end side projecting portions 118b are arranged at positions which are 180 degrees away from each other in the circumferential direction of the ring of each curvable piece 118. With the above-described arrangement, the two front end side projecting portions 118a and the two rear end side projecting portions 118b of each curvable piece 118 are arranged at positions 90 degrees away from each other.

When there are two curvable pieces, one in front and the other in rear, to be adjacent to each other, there is created an overlap section where the two rear end side projecting portions 118b of a front-side curvable piece 118, and the two front end side projecting portions 118a of a rear-side curvable piece 118 overlap, and a pivotal pin 120 is connected to be pivotable to the overlap section.

Further, as can be seen in FIG. 12A, in the curvable portion 109 of the embodiment, gap portions 121 of substantially a V-letter shape are made on both sides of a pivot joint portion made of the pivotal pin 120 located end portions of front-to-rear adjacent two curvable pieces 118.

In the leading end curvable piece 118A located at the first leading position of the curvable piece group 119, two front end side projecting portions 118a are not provided. The leading end curvable piece 118A is fixed to the rear end portion of the distal end structural portion 110 with fixation means such as adhesion, spiral piece, soldering, welding or press fitting. Further, in a trailing end curvable piece 118b located at the last trailing position of the curvable piece group 119, two rear end side projecting portions 118b are not provided. The trailing end curvable piece 118B is fixed to the distal end portion of the flexible tube portion 108 with fixation means such as adhesion, spiral piece, soldering, welding or press fitting.

A flexible soft tube member 122 is provided on an outer circumferential surface of the curvable portion 109. An outer side of the curvable piece group 119 of the curvable portion 109 is covered by the tube member 122.

Further, a plurality of, in this embodiment, four angle wires 123 (that is, two angle wires 123 for an up-and-down direction curving operation, and two angle wires 123 for a right-to-left direction curving operation) are fixed by their distal end portions to the leading end curvable piece 118A of the curvable portion 109. The proximal end portions of these angle wires 123 are extended out to the hand-side operating portion 107. The operating portion 107 is provided with a curving operation mechanism, though it is not shown in the figure, for pulling each of the angle wires 123 as the operation knob is operated.

In order to curve the curvable portion 109 of the endoscope 102, any one or two of the angle wires 123 are pulled via the curving operation mechanism by operating the operation knob. Here, the curvable portion 109 of the endoscope 102 is operated with the curving operation portion such as the curving knob of the operation portion 107, and thus it is curved from a standard shape drawn in substantially a linear state as shown in FIG. 12A, to a curved shape which is curved in substantially an arc state in an up-and-down or right-to-left direction as shown in FIG. 11.

Further, while the curvable portion 109 of the endoscope 102 is not being curved, that is, the entire curvable portion 109 is maintained in a standard shape which is drawn in substantially a linear state, gap portions 121 having a V-letter shape between the end edge portions of adjacent pair of curvable pieces 118 are held at the same intervals in all directions, that is, four directions, up, down, right and left, of each angle wire 123. With this structure, in order to curve the curvable portion 109, as the leading end curvable piece 118A is pulled to the hand side by means of the angle wires 123 which is pulled, each curvable piece 118 is pivoted around the pivotal pin 120 so as to narrow the V-shaped gap portions 121 between the end edge portions of the curvable pieces 118 on a side of the direction in which the angle wires 123 are pulled, whereas to widen the gap portions 121 on the opposite side. Thus, the entire curvable portion 109 is curved in substantially an arc shape. Further, by the curving operation of the curvable portion 109, it can be curved to form an arbitrarily curved shape between the standard shape which is drawn in substantially a linear state and a maximum curved shape which is curved in an arc state. It should be noted here that when the curvable portion 109 is curved at maximum, the V-shaped gap portions 121 between the end edge portions of adjacent pairs of the curvable pieces 118 are narrowed such that the end edge portions of each adjacent pair of front one and next curvable pieces abut against each other.

Further, in the curvable portion 109 of this embodiment, there are a plurality of curvable regions having different radiuses of curvature, that is, a first curvable region WA having a small radius of curvature and a second curvable region WB having a larger radius of curvature that that of the first curvable region WA. Here, the first curvable region WA is provided at the distal end side of the curvable portion 109, and the second curvable region WB is provided on a rear side to the first curvable region WA.

Further, in this embodiment, the curvable pieces 118 provided in the first curvable region WA are set such that the maximum gap measurement of the substantially V-shaped gap portions 121 between the end edge portions of front-to-next two adjacent curvable pieces 118, that is, a so-called shoulder opening measurement, becomes t1, in a standard shape where the curvable portion 109 are drawn in substantially a linear state as shown in FIG. 12A. At this point, the curvable pieces 118 provided in the second curvable region WB will have a shoulder opening measurement of t2, and a relationship of t1>t2 is set. Therefore, when the curvable portion 109 is curved in a maximum curvature state, it is maintained in such a state that the radius of curvature is small in the first curvable region WA at the distal end side of the curvable portion 109, where the radius of curvature is large in the second curvable region WB located in the rear of the first curvable region WA.

As shown in FIG. 13B, in the insertion portion 106 of the endoscope 102, the shape detection probe 128 for detecting the shape of the insertion portion 106 is built together with the four angle wires 123 arranged in all of up, down, right and left directions, two light guide fibers 124, an image signal transmission cable 125 for the imaging means such as the CCD, a gas/water supply channel 126 and a treatment tool through channel 127. Here, tip end portions of the two light guide fibers 124 are arranged to oppose to each other in inner surface sides of two illumination window portions provided in the distal end structure portion 110, and their proximal end portions are extended through the operation portion 107 and the universal cord 111, into the connector 112. Further, illumination light from the light source device 103 is allowed to enter the light guide fibers 124 via the connector 112. Further, the illumination light transmitted from the light guide fibers 124 are emitted to the outside in an expanding fashion by the illumination window portion.

The proximal end portion side of the image signal transfer cable 125 extends from the inside of the operation portion 107, and it is connected to the control device 115 via the inside of the universal cord 111, the inside of the connector 112 and the connection cable 113. In an observation with the endoscope, an observed image within a view range is transmitted from an observation window to an objective lens, and with the objective lens, the observed image is formed in the imaging means such as the CCD. Further, the observed image is converted into an electrical signal by the imaging means such as the CCD, and then transmitted to the control device 115 by the image signal transmission cable 125 via a CCD connector 113a of the connection cable 113.

In the meantime, a distal end portion of the gas/water supply channel 126 is connected to a gas/water supply nozzle provided in the distal end structure portion 110, whereas a proximal end portion thereof extends through the insides of the operation portion 107 and the universal cord 111, into the connector 112. Further, the distal end portion of the treatment tool through channel 127 is attached to the distal end opening section of the treatment tool through channel 127 provided in the distal end structure portion 110, whereas a proximal end portion thereof is attached to a treatment tool insertion portion provided in the operation portion 107.

The shape detection probe 128 of this embodiment is provided within the insertion portion 106 of the endoscope 102 substantially over its entire length. FIG. 13A shows the internal structure of the shape detection probe 128 in this embodiment. As can be seen in FIG. 13A, a core wire 129 is provided in the shape detection probe 128 at a position of its axial center. A tip end member 130a is fixed to a tip end portion of the core wire 129, and a rear end member 130b is fixed to a rear end portion thereof.

Further, a plurality of magnetic field generating coils 131 each generating a magnetic field are fixed onto the surrounding of the core wire 129 at predetermined intervals with an adhesive or the like. It should be noted here that a plurality of coils 131 of the shape detection probe 128 are arranged at substantially equal intervals over the substantially entire length of the insertion portion 106 of the endoscope 102. Further, the interval between front-to-rear adjacent coils 131 may be varied appropriately depending on the location of the insertion portion 106 of the endoscope 102.

Two signal wires 132 are connected to each coil 131. An armor tube 133 for the protection of each coil 131 and the signal wires 132 is mounted on an outer circumference of the shape detection probe 128. The armor tube 133 is an elastic tube made of, for example, silicon rubber.

Figure 14:
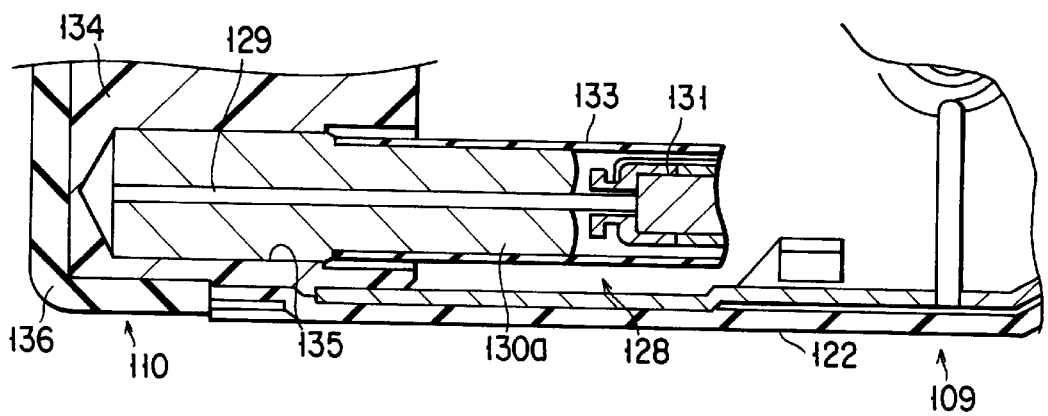
FIG. 14 is a longitudinal sectional view showing a fixation state of a distal end of the shape detection probe in the endoscope according to the seventh embodiment.

Further, the distal end portion of the shape detection probe 128 is fixed to the distal end structure portion 110 as shown in FIG. 14. Here, a shape detection probe mount hole 135 is made in a rear end surface of a main body 134 of the distal end structure portion 110. A distal end member 130a is fixed in the probe mount hole 135 of the main body 134 of the distal end structure portion, as the member is inserted into the hole 135. It should be noted that a distal end cover 136 for covering the entire outer surface of the main body 134 is mounted on the distal end structure portion 110.

Figure 12B:
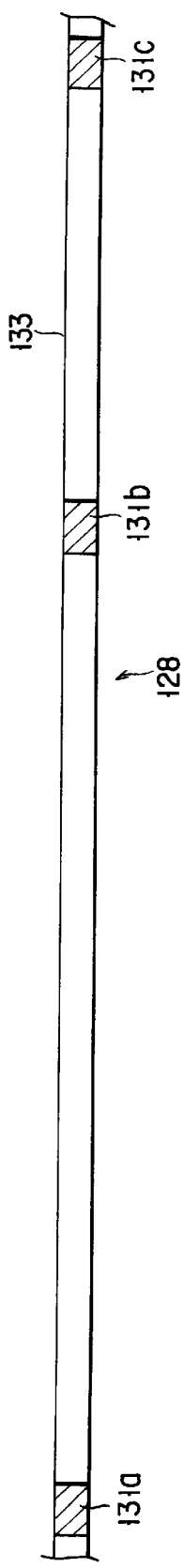
FIG. 12B is a lateral view showing a shape detection probe disposed in a curvable portion in the endoscope according to the seventh embodiment.

Further, in this embodiment, as shown in FIG. 12B, three magnetic field generating coils 131a, 131b and 131c on the distal end side of the shape detection probe 128 are provided in the curvable portion 109. Here, the first coil 131a at the leading end position is disposed at a position corresponding to the leading end curvable piece 118A located at the leading end position of the curvable portion 109, whereas the third coil 131c is disposed at a position corresponding to the trailing end curvable piece 118B located at the trailing end position of the curvable portion 109. Further, the coil 131b is disposed at an intermediate position between the coil 131a at the leading end position and the coil 131c at the trailing end position is arranged in the second curvable region WB of the curvable portion 109, where the radius of curvature is large.

In the endoscope 102 of this embodiment, the magnetic field generated from each magnetic field generating coil 131 of the shape detection probe 128 is detected by the antenna 117. An output signal from the antenna 117 is input to the shape detecting control device 116, so as to detect the shape of the insertion portion 106, and the detected shape of the insertion portion 106 is displayed on a second monitor 105 provided exclusively for that purpose. On the screen of the second monitor 5, the positions where the coils 131 are detected on the basis of the magnetic fields generated from those magnetic field generating coils 131 of the shape detection probe 128 are displayed in the form of dot. Then, as the dots of the detection positions of the coils 131 are connected, the shape of the insertion portion 106 can be displayed on the screen of the second monitor 105 in the form of pseudo-image.

Figure 15:
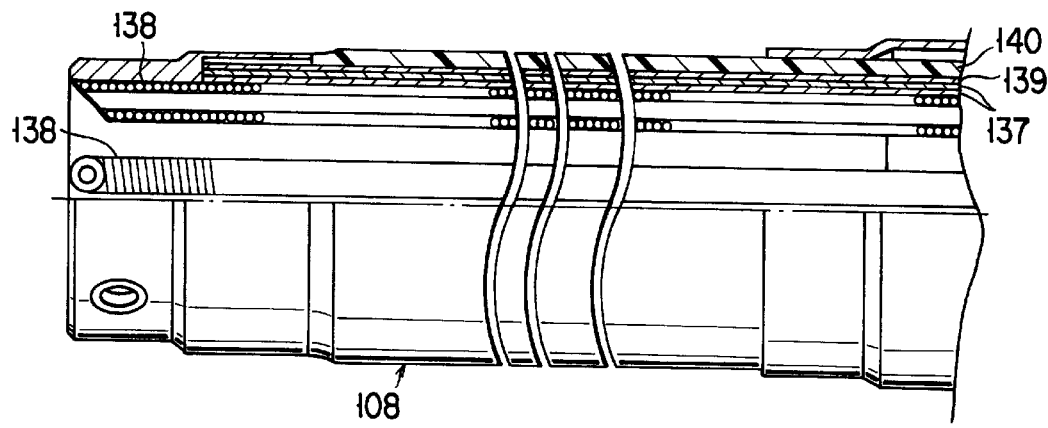
FIG. 15 is a longitudinal sectional view showing a main portion, designed to illustrate an internal structure of a flexible tube portion in the endoscope according to the seventh embodiment.

FIG. 15 shows the internal structure of the flexible tube portion 108 of the endoscope 102 of this embodiment. In the flexible tube portion 108, a flex mount portion 137 formed by winding two spiral tubes (flex) made of thin-plate metal bands helically wound, in double in a state where the winding direction is reversed, is provided at the innermost circumferential surface side. In the inner circumferential surfaces of the flex mount portion 137, four wire guides 138 to which angle wires 124 set in four, that is, up, down, right and left directions, are respectively inserted, are arranged.

Further, a blade 139 of a net tube made of a metal or resin, is mounted on the outer circumference of the flex mount portion 137. Further, a resin tube 140 made of a plastic material having a flexibility is mounted on the outer circumference of the blade 139.

Figure 16:
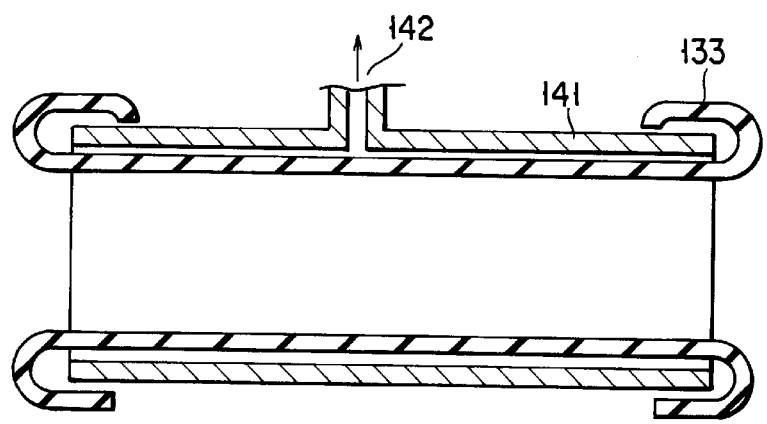
FIG. 16 is a longitudinal sectional view showing a main portion, designed to illustrate the attachment operation for the armor tube of the shape detection tube in the endoscope according to the seventh embodiment.

FIG. 16 shows a tube-like jig 141 for a tube assembly operation, used in an operation of mounting an armor tube 133 on a shape detection probe 128 in the endoscope 102 of this embodiment. For the tube-like jig 141, a tube member having substantially the same length as that of the shape detection probe 128 is used. The size of the inner diameter of the tube-like jig 141 is set to be larger than the size of the outer diameter of the armor tube 133 of the shape detection probe 128.

Further, a suction hole 142 is made in the outer circumferential surface of the tube-like jig 141 at substantially the central position along the length direction of the tube-like jig 141. To the suction hole 142, suction means such as a vacuum pump is connected although it is not shown in the figure.

During the assembling operation of the shape detection probe 128, an intermediate assembly body 143 in which the structural members other than the armor tube 133, that is, the core wire 129, the distal end member 130a, a plurality of magnetic field generating coils 131 and the trailing end member 130b are integrated in one unit, is assembled. After the assembling of the intermediate assemble member 143, the tube mounting operation for mounting the armor tube 133 to the intermediate assembly body 143 is carried out with use of the tube-like jig 141.

When the tube-like jig 141 is used. The armor tube 133 is inserted in advance to the inside of the tube-like jig 141. Then, after both end sides of the armor tube 133 are extended to outsides of the tube-like jig 141, these extending end portions are engaged with the tube-like jig 141 while they are folded back on the outer circumferential surface sides. In this state, the inside of the tube-like jig 141 is suctioned from the suction hole 142 of the jig 141 to create a negative pressure, by the suction means such as the vacuum pump which is not shown, and thus the armor tube 133 is tightly attached to the inner circumferential surface of the tube-like jig 141. Thus, the tube diameter of the armor tube 133 can be expanded to a tube diameter equal to the inner diameter side of the tube-like jig 141. Then, while maintaining the state, the intermediate assembly body 143 is inserted in the armor tube 143 whose tube diameter has been expanded. Thus, the intermediate assembly body 143 can be easily inserted into the armor tube 133.

Further, while the intermediate assembly body 143 is being inserted in the armor tube 133, the suction of the tube-like jig 141 is released, and the folded-back sections at both ends of the armor tube 133 are removed from the both ends of the armor tube 133. Thus, the tube mounting operation for mounting the armor tube 133 to the intermediate assembly body 143 is finished.

Next, the operation of the above-described structure will now be described. When the endoscope 102 of this embodiment is used, the insertion portion 106 of the endoscope 102 is inserted to a pipe path used for an industrial purpose, or to a tube canal to be examined by the endoscope, such as a cavity of a body canal. In order to insert the insertion portion 106 of the endoscope 102 into a cavity, the operation knob of the operation portion 107 is operated to follow the shape of the cavity in which the portion 106 is inserted. Here, as the knob of the operation portion 107 is operated, any one or two angle wires 123 are pulled, and with these angle wires 123 operated, the curvable portion 109 is curved via these angle wires 123.

In the case where the distal end structure portion 110 of the endoscope 102 is inserted to, for example, a deep part of the large intestine through curved sections of the body cavity, or it is inserted to a deep portion of a pipe path for an industrial use, the insertion portion 106 is further inserted while the curvable portion 109 is curved to follow the shape of the cavity in which the portion is inserted. As the insertion portion 106 is inserted, the flexible tube portion 108 is deformed in accordance with the shape of the insertion tube path.

In this embodiment, during the insertion operation of the insertion portion 106 of the endoscope 102, the magnetic field generated from each magnetic field generating coil 131 of the shape detection probe 128 is detected by the antenna 117. An output signal from the antenna 117 is input to the shape detecting control device 116, so as to detect the shape of the insertion portion 106, and the detected shape of the insertion portion 106 is displayed on a second monitor 105 provided exclusively for that purpose. On the screen of the second monitor 105, the positions where the coils 131 are detected on the basis of the magnetic fields generated from those magnetic field generating coils 131 of the shape detection probe 128 are displayed in the form of dot. Then, as the dots of the detection positions of the coils 131 are connected, the shape of the insertion portion 106 can be displayed on the screen of the second monitor 105 in the form of pseudo-image.

Further, while the curvable portion 109 of the endoscope 102 is not being curved, it is maintained in a standard shape which is drawn in substantially a linear state. Here, the gap portions 121 having a V-letter shape between the end edge portions of adjacent pair of curvable pieces 118 are held at the same intervals in all directions, that is, up, down, right and left directions, of each angle wire 123.

With this structure, in order to curve the curvable portion 109, as the leading end curvable piece 118A is pulled to the hand side by means of the angle wires 123 which is pulled, each curvable piece 118 is pivoted around the pivotal pin 120 so as to narrow the V-shaped gap portions 121 between the end edge portions of the curvable pieces 118 on a side of the direction in which the angle wires 123 are pulled, whereas to widen the gap portions 121 on the opposite side. Thus, the entire curvable portion 109 is curved in substantially an arc shape.

Further, by the curving operation of the curvable portion 109, it can be curved to form an arbitrarily curved shape between the standard shape which is drawn in substantially a linear state and a maximum curved shape which is curved in an arc state. It should be noted here that when the curvable portion 109 is curved at maximum, the V-shaped gap portions 121 between the end edge portions of adjacent pairs of the curvable pieces 118 are narrowed such that the end edge portions of each adjacent pair of front one and next curvable pieces abut against each other.

Further, when the curvable portion 109 is curved at the maximum curved state, such a state is maintained that the radius of curvature becomes small in the first curvable region WA on the distal end side of the curvable portion 109, where as it becomes large in the second curvable region WB which is on the rear side of the first curvable region WA.

With the above-described structure, the following effect can be obtained. That is, in this embodiment, the maximum gap measurement of the substantially V-shaped gap portions 121 between the end edge portions of front-to-next two adjacent curvable pieces 118 located in the first curvable region WA, that is, a so-called shoulder opening measurement t1, and that of the curvable pieces 118 located in the second curvable region WB, that is, t2, are set to have a relationship of t1>t2. In this manner, when the curvable portion 109 is curved at the maximum curved state, such a state is maintained that the radius of curvature becomes small in the first curvable region WA on the distal end side of the curvable portion 109, where as it becomes large in the second curvable region WB which is on the rear side of the first curvable region WA. Further, of three magnetic field generating coils 131a, 131b and 131c of the shape detection probe 128 provided in the curvable portion 109, the coil 131b disposed at an intermediate position between the coil 131a at the leading end position and the coil 131c at the trailing end position is located in the second curvable region WB of the curvable portion 109, where the radius of curvature is large. With this structure, while curving the curvable portion 109, a tensile force and bending force acting on, for example, the connection portion between the end of the coil 131b and the signal line 132 and around the end edge portion of the coil 131b of the armor tube 133 can be made small. Therefore, the breakage of the connection portion between a coil end of the shape detection probe 128 and a signal line 132, around the end edge of the coil 131b of the armor tube 133 and the like, can be prevented, thus making it possible to improve the durability of the shape detection probe.

Furthermore, in the shape detection probe 128 of this embodiment, the coil 131a at the leading end position and the coil 131c at the trailing end position are disposed at positions corresponding respectively to hard sections such as the leading end curvable piece 118A and the trailing end curvable piece 118B. With this arrangement, while curving the curvable portion 109, the coil 131a at the leading end position and the coil 131c at the trailing end position are not influenced by the curvature of the curvable portion 109.

FIG. 17A shows the eighth embodiment of the present invention. In this embodiment, the structure of each of the first curvable region WA, where the radius of curvature is small, and the second curvable region WB, where the radius of curvature is large, in the curvable portion 9 of the seventh embodiment (see FIGS. 11 to 16) is remodeled as will now be described. It should be noted that the sections other than the above-mentioned structure are the same as those of the seventh embodiment. Here, the same structural elements as those of the seventh embodiment will be designated by the same reference numerals, and the explanations therefor will not be repeated.

That is, in the seventh embodiment, the maximum gap measurement of the substantially V-shaped gap portions 121 between the end edge portions of front-to-next two adjacent curvable pieces 118 located in the first curvable region WA, that is, a so-called shoulder opening measurement t1, and that of the curvable pieces 118 located in the second curvable region WB, that is, t2, are set to have a relationship of t1>t2. In this manner, when the curvable portion 109 is curved at the maximum curved state, such a state is maintained that the radius of curvature becomes small in the first curvable region WA on the distal end side of the curvable portion 109, where as it becomes large in the second curvable region WB which is on the rear side of the first curvable region WA. By contrast, in this embodiment, the maximum gap measurement of the substantially V-shaped gap portions 121 between the end edge portions of any adjacent pairs of all of the curvable pieces 118, that is, a so-called shoulder opening measurement, is maintained at a constant measurement t3, and at the same time, a thin portion 122a having a thickness of ta, which is obtained by thinning the tube member 122 having a thickness of t, for covering the outer circumferential surface of the curvable portion 109, is provided on the distal end side of the curvable portion 109, whereas a thick portion 122b having a thickness of tb, obtained by thickening the tube member 122 having a thickness t, is provided for the rear end side of the curvable portion 109. Here, the thickness ta of the thin portion 122a, and the thickness tb of the thick portion 122b are set to have a relationship of ta<tb. Further, the thin portion 122a of the tube member 122 is set to have approximately a half of the entire length of the tube member 122, and a thick portion 122b is formed on the other section than the thin portion 122a.

In this embodiment, the thin portion 122a of the tube member 122 is disposed on the distal end side of the curvable portion 109, whereas the thick portion 122b of the tube member 122 is disposed on the rear end side of the curvable portion 109. With this structure, while curving the curvable portion 109, the thin portion 122a of the tube member 122 on the distal end side of the curvable portion 109 becomes easily curvable, whereas the thick portion 122b of the tube member 122 on the rear end side of the curvable portion 109 becomes hard to curve. Therefore, in this embodiment, when the curvable portion 109 is curved in a maximum curvature state, the first curvable region WA can be created in the distal end side of the curvable portion 109, where the radius of curvature is small, and the second curvable region WB can be created in the rear of the first curvable region WA, where the radius of curvature is large, as in the seventh embodiment. Consequently, the effect similar to the seventh embodiment can be obtained in this embodiment.

FIG. 17B shows the ninth embodiment of the present invention. In this embodiment, a tube member 122 of the curvable portion 109 of the eighth embodiment (see FIG. 17A), that is, a tube member 122 having a structure in which a thin portion 122a of the tube member 122 is provided on a distal end side of the curvable portion 109, and a thick portion 122b of the tube member 122 is provided on a rear end side of the curvable portion 109, is disposed on the outer circumferential surface of a curvable piece group 119 having the identical structure to the curvable piece group 119 of the curvable portion 109 of the seventh embodiment (see FIGS. 11 to 16).

Therefore, in this embodiment, when the curvable portion 109 is curved in a maximum curvature state, the first curvable region WA can be created in the distal end side of the curvable portion 109, where the radius of curvature is small, and the second curvable region WB can be created in the rear of the first curvable region WA, where the radius of curvature is large, as in the seventh embodiment. Consequently, the effect similar to the seventh embodiment can be obtained in this embodiment.

Figure 18:
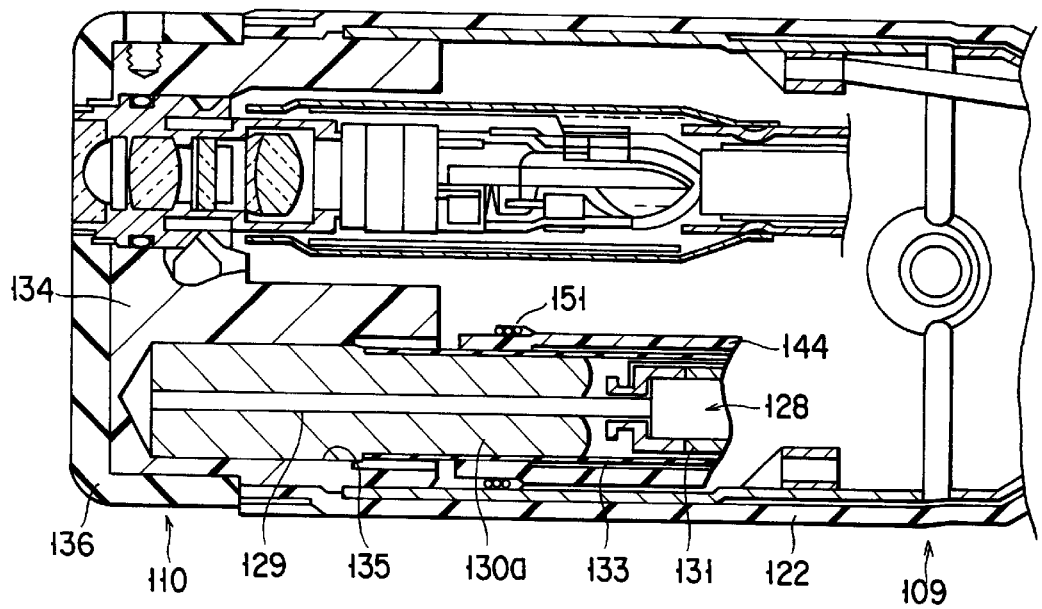
FIG. 18 is a longitudinal sectional view showing an internal structure of a distal end of an insertion portion in the endoscope according to the tenth embodiment.

FIG. 18 shows the tenth embodiment of the present invention. In this embodiment, the internal structure of the endoscope 102 of the seventh embodiment (see FIGS. 11 to 16) is remodeled as will now be described. It should be noted that the sections other than the above-mentioned structure are the same as those of the seventh embodiment. Here, the same structural elements as those of the seventh embodiment will be designated by the same reference numerals, and the explanations therefor will not be repeated.

More specifically, in this embodiment, a protection tube 144 is provided on an outer side of the shape detection probe 128 of the seventh embodiment, which is inserted therein, in the inside of the insertion portion 106. The protection tube 144 is made of a smooth synthesis resin material, for example, a urethane tube, a Teflon-based material-made tube, a silicon tube or the like. A distal end portion of the protection tube 144 is reeled around the outer circumferential surface of the rear end portion of the distal end member 130a, and fixed thereon with adhesive. Thus, a reel fixation portion 151 of the protection tube 144 is formed on the outer circumferential surface of the rear end portion of the distal end member 130a. Further, an antifriction material is inserted in the gap between the protection tube 144 and the shape detection probe 128. With this structure, if a friction is generated between the protection tube 144 and the shape detection probe 128 as the endoscope 102 moves, the detection probe 128 will not be damaged.

With the above-described structure, the following effect can be obtained. That is, in this embodiment, the protection tube 144 for the shape detection probe 128 is provided within the insertion portion 106 over substantially its entire length. Therefore, if the shape of the insertion portion 106 is changed, the contents such as the light guide fiber 124, image signal transmission cable 125, water/air supply channel 126 and treatment tool through channel 127, provided in the insertion portion 106, will not be brought into direct contact with the shape detection probe 128. Thus, a damage on the shape detection probe 128, which is caused as the other contents provided in the insertion portion 106 are brought into direct contact with the shape detection probe 128, can be prevented. Consequently, the durability of the shape detection probe 128 and the durability of the endoscope 102 can be easily improved.

It should be noted that the protection tube 144 of this embodiment may be made of a plastic net-like tube or a plastic spiral tube (flex) or tightly wound coil.

Figure 19:
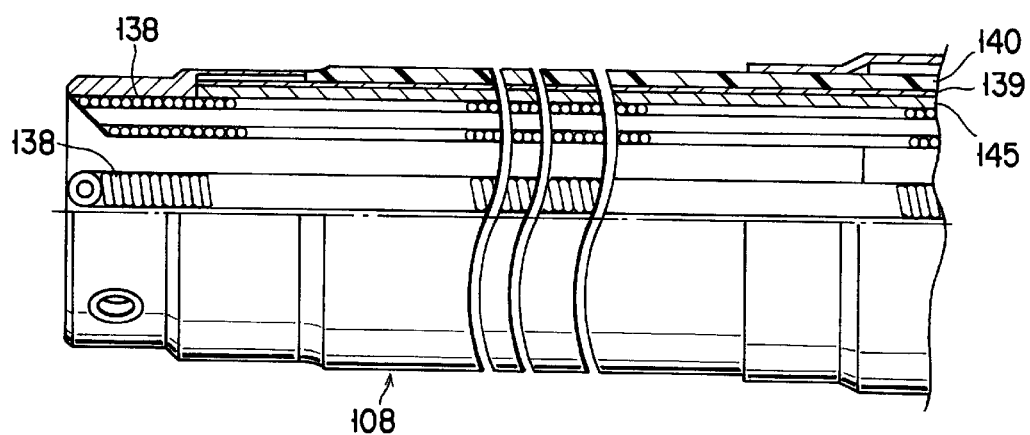
FIG. 19 is a longitudinal sectional view showing an internal structure of a flexible tube portion of an insertion portion in the endoscope according to the eleventh embodiment.

FIG. 19 shows the eleventh embodiment of the present invention. This embodiment is a remodeled version of the seventh embodiment (see FIGS. 11 to 16), where the internal structure of the flexible tube portion 108 of the endoscope 102 is changed as will be described.

More specifically, in this embodiment, a single-structure spiral tube 145 is mounted in place of the flex mount portion 137 formed by winding two spiral tubes (flex) in double in a state where the winding direction is reversed, used in the flexible tube portion 108 in the seventh embodiment.

The embodiment having the above-described structure exhibits the following effect. That is, in this embodiment, the spiral tube 145 having a single structure is provided in the flexible tube portion 108, and therefore the metal part within the flexible tube portion 108 can be reduced. Accordingly, the amount of attenuation of the magnetic field generated from each coil 131 of the shape detection probe 128 within the flexible tube portion 108 can be reduced, and therefore the accuracy of the detection of the shape of the insertion portion 106 by the shape detection probe 128 can be improved.

Figure 20:
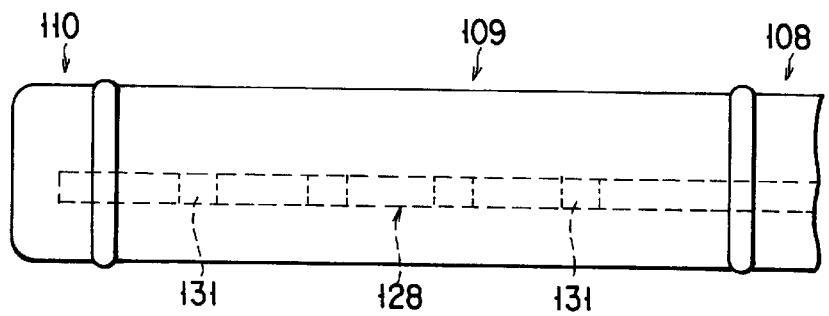
FIG. 20 is a lateral view showing a main portion of the twelfth embodiment of the present invention.
Figure 21:
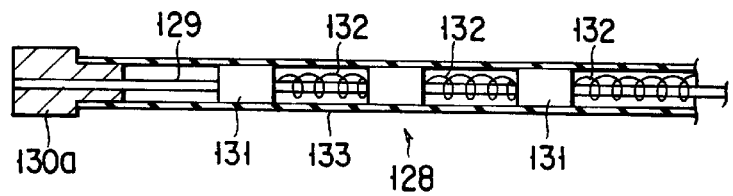
FIG. 21 is a longitudinal sectional view of a shape detection probe of the twelfth embodiment.

FIGS. 20 and 21 show the twelfth embodiment of the present invention. This embodiment is a remodeled version of the seventh embodiment (see FIGS. 11 to 16), where the structure of the shape detection probe 128 is changed as will be described.

That is, the seventh embodiment discusses a structure in which there are three coils 131a, 131b and 131c of the shape detection probe 128, provided in the curvable portion 109 as can be seen in FIG. 12B, whereas in this embodiment, there are four or more magnetic field generating coils 131 provided in the shape detection probe 128 of the curvable portion 109.

Further, in the shape detecting control device 116, there are provided a disconnection detection means for detecting a disconnection of a wire in a coil 131 in the shape detection probe 128, and an image processing means for displaying the shape of the insertion portion 106 on a screen of the second monitor 105 in the form of pseudo-image only from the data of the magnetic field generated from those of magnetic field generating coils, which are not disconnected on the basis of the detection signal from the disconnection detection means.

Here, in this embodiment, there are four or more magnetic field generating coils 131 provided in the shape detection probe 128 of the curvable portion 109. With this structure, even if one of four magnetic field generating coils 131 provided in the curvable portion 109 is damaged to be defective, the shape of the curvable portion 109 can be accurately recognized with the rest of the three coils. Thus, as compared to the case where there are only three coils 131 provided in the curvable portion 109, there will not be a problem of becoming impossible to accurately recognize the shape of the curvable portion 109 even if one of the three coils becomes out of order. Therefore, the durability of the shape detection probe 128 can be improved, and accordingly the life time of the detection probe 128 can be prolonged.

Figure 22:
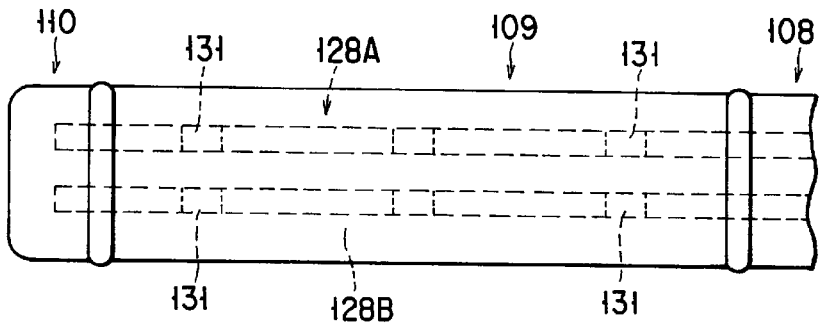
FIG. 22 is a lateral view showing a main portion of the thirteenth embodiment of the present invention.

FIG. 22 shows the thirteenth embodiment of the present invention. This embodiment is a remodeled version of the seventh embodiment (see FIGS. 11 to 16), where the structure of the shape detection probe 128 is changed as will be described.

That is, the seventh embodiment discusses a structure in which one shape detection probe 128 is provided within the insertion portion 106 of the endoscope 102 over substantially its entire length, whereas in this embodiment, a plurality of, for example, two shape detection probes 128 are provided within the insertion portion 106 to be substantially in parallel to each other.

More specifically, in this embodiment, two magnetic field generating coils 131 are provided at the same position with respect to the axial direction of the insertion portion 106 of the endoscope 102. With this structure, even if one of the coils 131 becomes out of order, the data of such a defect can be compensated by the magnetic field generated from the coil 131 disposed at the location of the defect by means of the other coil 131. Thus, in this embodiment, if one of the two magnetic field generating coils 131 arranged at the same position with respect to the axial direction of the insertion portion 106 of the endoscope 102 becomes out of order, the data of such a defect can be compensated by the magnetic field generated from the other coil 131. In this manner, the shape of the insertion 106 can be accurately recognized.

Figure 23:
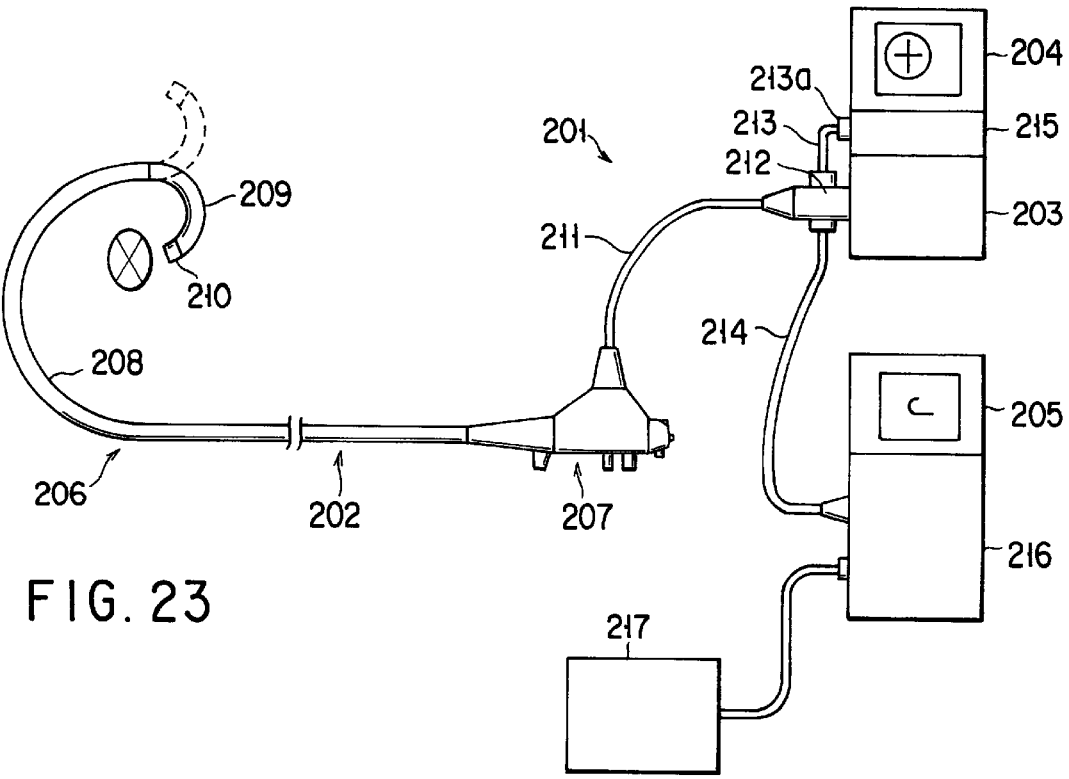
FIG. 23 is a schematic structural diagram showing an entire endoscope device according to the fourteenth embodiment of the present invention.

FIGS. 23 to 26 show the fourteenth embodiment of the present invention. FIG. 23 shows a schematic structure of an entire system of an endoscope device 201 according to this embodiment. In the endoscope device 201 of this embodiment, an endoscope 202, a light source unit 203, a first monitor 204 for displaying an endoscopic image and a second monitor 205 for displaying a shape of the endoscope 202 are provided.

In the endoscope 202 of this embodiment, a hand-side operating portion 207 is provided in a proximal end portion of a slender insertion portion 206 to be inserted into a cavity of a body canal. Here, in the insertion portion 206, a curvable portion 209 which can change its shape in a curved state is provided in a distal end portion of a slender flexible tube portion 208. Further, a hard distal end structural portion 210 is connected to a distal end portion of the curvable portion 209. In the distal end structural portion 210, not only a light guide fiber 224 (see FIG. 26), which serves as an illumination optical system, an objective lens 238 of an observation optical system 237 (see FIG. 25), and imaging means such as a CCD 239, but also air-supply and water-supply nozzles and a treatment tool through channel 227 (see FIG. 26) are built.

At the operation portion 207 on the hand side of the endoscope 202, a curving operation portion such as a curving knob for operating the curvable portion 209 to curve, is provided, and one end portion of a universal code 211 is connected to the operation portion 207. A connector 212 is mounted to another end portion of the universal code 211. Further, the connector 212 is detachably connected to the light source device 203.

Further, one end portion of each of two connection cables 213 and 214 is connected to the connector 212. Here, one connection cable 213 is connected to the control device 215 such as a camera control unit (CCU). To the control device 215, the first monitor 204 is connected.

The other connection cable 214 is connected to a shape detection control device (insertion portion shape detection means) 216 designed for detecting the shape of the insertion portion 206 of the endoscope 202. To the shape detection control device 216, an antenna 217 and a second monitor 205 are connected.

FIG. 24A shows an internal structure of the curvable portion 209 of the endoscope 202. In the curvable portion 209 of this embodiment, a curvable piece group 219 in which a plurality of ring-like curvable pieces 218 are arranged side by side in the axial direction of the insertion portion 206 is provided. Here, two front end side projecting portions 218a are set in a front end portion of each curvable piece 218 to project forwards. The two front end side projecting portions 218a are arranged at positions which are 180 degrees away from each other in the circumferential direction of the ring of each curvable piece 218.

Further, two rear end side projecting portions 218b are set in a rear end portion of each curvable piece 218 to project backwards. The two rear end side projecting portions 218b are arranged at positions which are 180 degrees away from each other in the circumferential direction of the ring of each curvable piece 218. With the above-described arrangement, the two front end side projecting portions 218a and the two rear end side projecting portions 218b of each curvable piece 18 are arranged at positions 90 degrees away from each other.

When there are two curvable pieces, one in front and the other in rear, to be adjacent to each other, there is created an overlap section where the two rear end side projecting portions 218b of a front-side curvable piece 218, and the two front end side projecting portions 218a of a rear-side curvable piece 218 overlap, and a pivotal pin 220 is connected to be pivotable to the overlap section.

Further, as can be seen in FIG. 24A, in the curvable portion 209 of the embodiment, gap portions 221 of substantially a V-letter shape are made on both sides of a pivot joint portion made of a pivotal pin 220 located between end edge portions of front-to-rear adjacent two curvable pieces 218.

In the leading end curvable piece 218A located at the first leading position of the curvable piece group 219, two front end side projecting portions 218a are not provided. The leading end curvable piece 218A is fixed to the rear end portion of the distal end structural portion 210 with fixation means such as adhesion, spiral piece, soldering, welding or press fitting. Further, in a trailing end curvable piece 218b located at the last trailing position of the curvable piece group 219, two rear end side projecting portions 218b are not provided. The trailing end curvable piece 218B is fixed to the distal end portion of the flexible tube portion 208 with fixation means such as adhesion, spiral piece, soldering, welding or press fitting.

A flexible soft tube member 222 is provided on an outer circumferential surface of the curvable portion 209. An outer side of the curvable piece group 219 of the curvable portion 219 is covered by the tube member 222.

Further, a plurality of, in this embodiment, four angle wires 223 (that is, two angle wires 223a1 and 223a2 for an up-and-down direction curving operation, and two angle wires 223b1 and 223b2 for a right-to-left direction curving operation) are fixed by their distal end portions to the leading end curvable piece 218A of the curvable portion 209. The proximal end portions of these angle wires 223 are extended out to the hand-side operating portion 207. The operating portion 207 is provided with a curving operation mechanism, though it is not shown in the figure, for pulling each of the angle wires 223 as the operation knob is operated.

In order to curve the curvable portion 209 of the endoscope 202, any one or two of the angle wires 223 are pulled via the curving operation mechanism by operating the operation knob. Here, the curvable portion 209 of the endoscope 202 is operated with the curving operation portion such as the curving knob of the operation portion 207, and thus it is curved from a standard shape drawn in substantially a linear state as shown in FIG. 24A, to a curved shape which is curved in substantially an arc state in an up-and-down or right-to-left direction as shown in FIG. 23.

Further, while the curvable portion 209 of the endoscope 202 is not being curved, that is, the entire curvable portion 209 is maintained in a standard shape which is drawn in substantially a linear state, gap portions 221 having a V-letter shape between the end edge portions of adjacent pair of curvable pieces 218 are held at the same intervals in all directions, that is, up, down, right and left directions, of each angle wire 223. With this structure, in order to curve the curvable portion 209, as the leading end curvable piece 218A is pulled to the hand side by means of the angle wires 223 which is pulled, each curvable piece 218 is pivoted around the pivotal pin 220 so as to narrow the V-shaped gap portions 221 between the end edge portions of the curvable pieces 218 on a side of the direction in which the angle wires 223 are pulled, whereas to widen the gap portions 221 on the opposite side. Thus, the entire curvable portion 209 is curved in substantially an arc shape. Further, by the curving operation of the curvable portion 209, it can be curved to form an arbitrarily curved shape between the standard shape which is drawn in substantially a linear state and a maximum curved shape which is curved in an arc state. It should be noted here that when the curvable portion 209 is curved at maximum, the V-shaped gap portions 221 between the end edge portions of adjacent pairs of the curvable pieces 218 are narrowed such that the end edge portions of each adjacent pair of front one and next curvable pieces 218 which interposes the gap portion 221 abut against each other.

Figure 26:
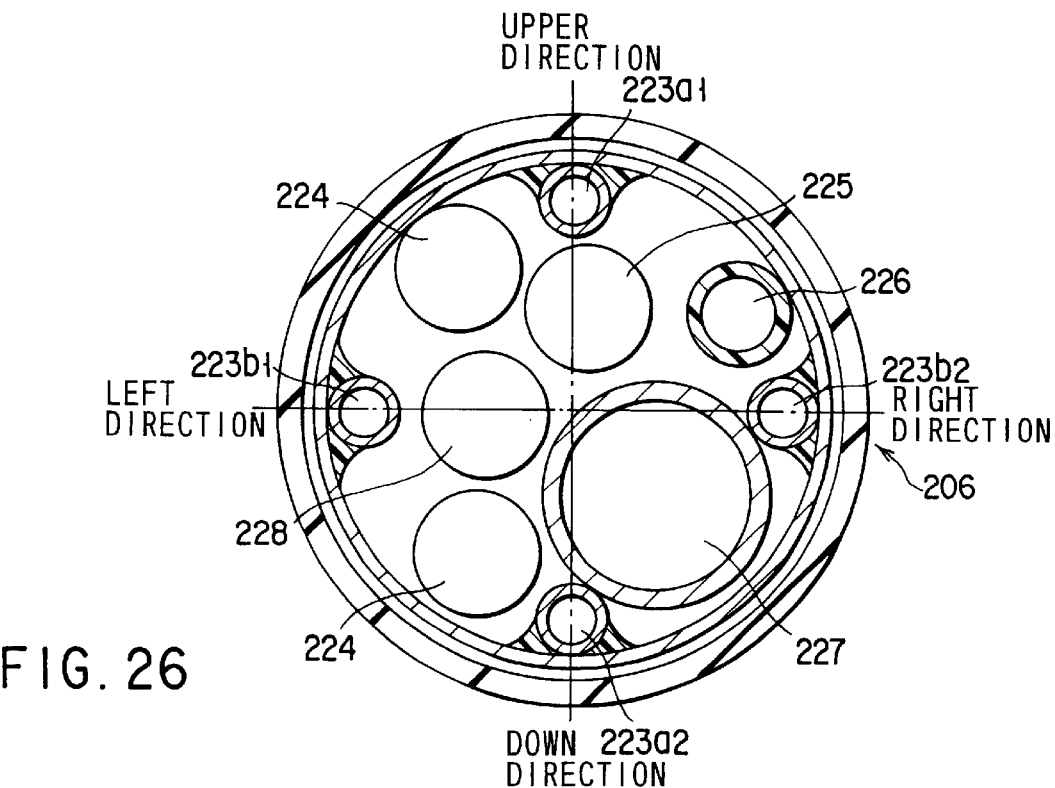
FIG. 26 is a cross sectional view taken along the line 26—26 in FIG. 25.

As shown in FIG. 26, in the insertion portion 206 of the endoscope 202, the shape detection probe 228 for detecting the shape of the insertion portion 206 is built together with the contents such as four angle wires 223a1, 223a2, 223b1 and 223b2 arranged in all of up, down, right and left directions, two light guide fibers 224, an image signal transmission cable 225 for the imaging means such as the CCD 238, a gas/water supply channel 226 and a treatment tool through channel 227. Here, tip end portions of the two light guide fibers 224 are arranged to oppose to each other in inner surface sides of two illumination window portions provided in the distal end structure portion 210, and their proximal end portions are extended through the operation portion 207 and the universal cord 211, into the connector 212. Further, illumination light from the light source device 203 is allowed to enter the light guide fibers 224 via the connector 212. Further, the illumination light transmitted from the light guide fibers 224 are emitted to the outside in an expanding fashion by the illumination window portion.

Figure 25:
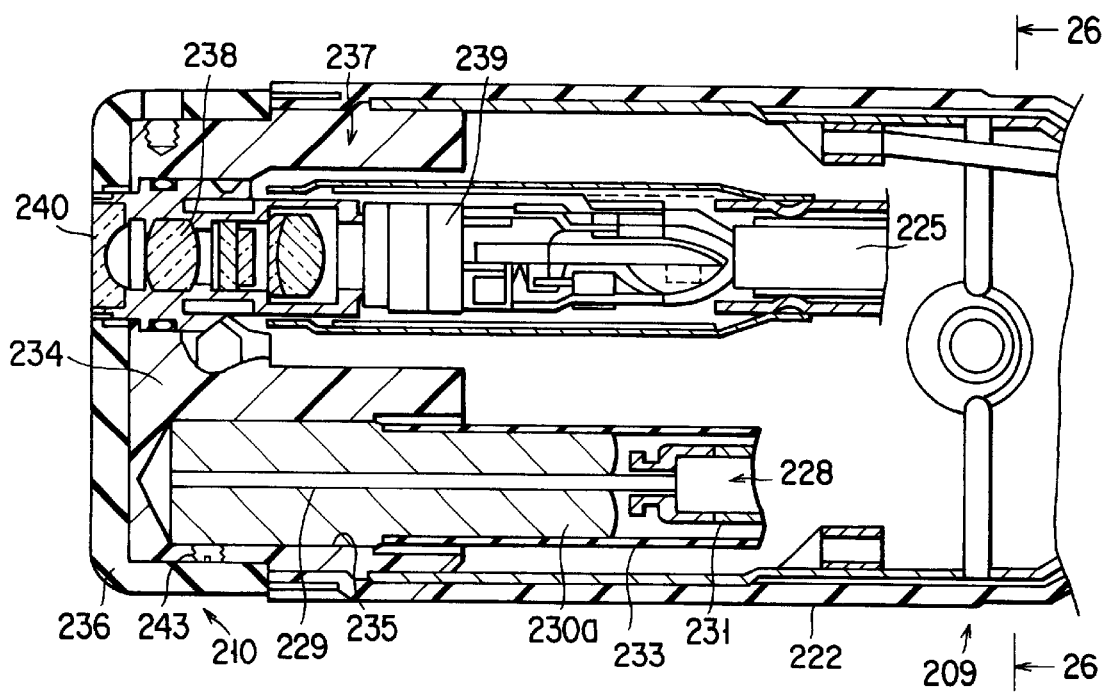
FIG. 25 is a longitudinal sectional view showing a fixation state of a distal end of the shape detection probe in the endoscope according to the fourteenth embodiment.

The proximal end portion side of the image signal transfer cable 225 extends from the inside of the operation portion 207, and it is connected to the control device 215 via the inside of the universal cord 211, the inside of the connector 212 and the connection cable 213. In an observation with the endoscope, an observed image within a view range is transmitted as shown in FIG. 25 from an observation window 240 to an objective lens 238, and with the objective lens 238, the observed image is formed in the imaging means such as the CCD 239. Further, the observed image is converted into an electrical signal by the imaging means such as the CCD 239, and then transmitted to the control device 215 by an image signal transmission cable 225 via a CCD connector 213a of the connection cable 213.

In the meantime, a distal end portion of the gas/water supply channel 226 is connected to a gas/water supply nozzle, though it is not shown in the figure, provided in the distal end structure portion 210, whereas a proximal end portion thereof extends through the insides of the operation portion 207 and the universal cord 211, into the connector 212. Further, the distal end portion of the treatment tool through channel 227 is attached to the distal end opening section (not shown) of the treatment tool through channel 227 provided in the distal end structure portion 210, whereas a proximal end portion thereof is attached to a treatment tool insertion portion provided in the operation portion 207.

The shape detection probe 228 of this embodiment is provided within the insertion portion 206 of the endoscope 202 substantially over its entire length. FIG. 24B shows the internal structure of the shape detection probe 228 in this embodiment. As can be seen in FIG. 24B, a core wire 229 is provided in the shape detection probe 228 at a position of its axial center. A tip end member 230a is fixed to a tip end portion of the core wire 229, and a rear end member 230b is fixed to a rear end portion thereof.

Further, a plurality of magnetic field generating coils 231 each generating a magnetic field are fixed onto the surrounding of the core wire 229 at predetermined intervals with an adhesive or the like. It should be noted here that a plurality of coils 231 of the shape detection probe 228 are arranged at substantially equal intervals over the substantially entire length of the insertion portion 206 of the endoscope 202. Further, FIG. 29D shows an arrangement state of the coil 231 of the shape detection probe 228D built in the endoscope 202 discussed so far, which has a long insertion portion 206, and FIG. 29E shows an arrangement state of the coil 231 of the shape detection probe 228E built in the endoscope 202 discussed so far, which has a short insertion portion 206.

Two signal wires 232 are connected to each coil 231. An armor tube 233 for the protection of each coil 231 and the signal wires 232 is mounted on an outer circumference of the shape detection probe 228. The armor tube 233 is an elastic tube made of, for example, silicon rubber. A filler 242 prepared by mixing silicon and a solvent is packed into the armor tube 233 to fill the gaps between the contents therein, such as the core wire 229, the coils 231 and signal wires 232.

Further, the distal end portion of the shape detection probe 228 is fixed to the distal end structure portion 210 as shown in FIG. 25. Here, in a rear end surface of a main body 234 of the distal end structure portion 210, a shape detection probe mount hole 235 having substantially a circular shape, is made. While being inserted in the shape detection probe mount hole 235 of the distal end structure portion main body 234, the tip end member 230a of the shape detection probe 28 is fixed therein by means of a fixation screw 243. It should be noted that a distal end cover 236 for covering the entire outer surface of the distal end structure portion main body 234 is provided on the distal end structure portion 210.

In the endoscope 202 of this embodiment, the magnetic field generated from each magnetic field generating coil 231 of the shape detection probe 228 is detected by the antenna 217. An output signal from the antenna 217 is input to the shape detecting control device 216, so as to detect the shape of the insertion portion 206, and the detected shape of the insertion portion 206 is displayed on the second monitor 205 provided exclusively for that purpose. On the screen of the second monitor 205, the positions where the coils 231 are detected on the basis of the magnetic fields generated from those magnetic field generating coils 231 of the shape detection probe 228 are displayed in the form of dot. Then, as the dots of the detection positions of the coils 231 are connected, the shape of the insertion portion 206 can be displayed on the screen of the second monitor 205 in the form of pseudo-image.

Further, in the endoscope 202 of this embodiment, the insertion portion shape detection probe 228 in the insertion portion 206 is arranged at a position where the amount of movement in the axial direction of the insertion portion becomes minimum when the curvable portion 209 is curved. More specifically, when the curvable portion 209 is curved at maximum, the shape detection probe 228 is disposed at approximately the central position with respect to the direction in which the radius of curvature becomes minimum, or the direction in which the amount of curvature is large, for example, in the up-and-down direction as shown in FIG. 26. Here, the curving direction of the curvable portion 209 is set by, for example, the positions of four angle wires 223 provided within the curvable portion 209. It should be noted that in many cases, the curving angle in the up-and-down direction is larger than that in the right-to-left direction in the endoscope 202 because of its usability and durability.

That is, as shown in FIG. 26, four angle wires 223 are arranged in the circumferential direction of the tube member 222 of the curvable portion 209 at intervals of 90 degrees. Further, in the case where two angle wires 223a1 and 223a2 for curving the portion in the up-and-down direction are arranged in the vertical direction of the illustration of the figure, and two angle wires 223b1 and 223b2 for curving the portion in the right-to-left direction are arranged in the horizontal direction with respect to the illustration of the figure, the direction which connects the two angle wires 223a1 and 223a2 directed in the up-and-down direction is set to be the up-and-down direction, whereas the direction which connects the two angle wires 223b1 and 223b2 directed in the right-to-left direction is set to be the right-to-left direction. With this arrangement, in FIG. 26, the insertion portion shape detection probe 228 is situated at substantially the central position with respect to the up-and-down direction, that is, any position on a standard line connecting the two angle wires 223b1 and 223b2 directed in the right-to-left direction. It should be noted here that alternatively, the shape detection probe 228 in the insertion portion 206 may be disposed at substantially the central position with respect to the direction in which the curving operation for the curvable portion 209 is frequently carried out.

Further, the insertion portion shape detection probe 228 of the endoscope 202 is extended in substantially a linear manner in the insertion portion 206 over the entire length of the insertion portion 206 of the endoscope 202 while positions of the probe 228 taken in its diameter direction are situated at substantially the same location.

Next, the operation of the above-described structure will now be described. When the endoscope 202 of this embodiment is used, the insertion portion 206 of the endoscope 202 is inserted to a pipe path used for an industrial purpose, or to a tube canal to be examined by the endoscope, such as a cavity of a body canal. In order to insert the insertion portion 206 of the endoscope 202 into a cavity, the operation knob of the operation portion 207 is operated to follow the shape of the cavity in which the portion 206 is inserted. Here, as the knob of the operation portion 207 is operated, any one or two angle wires 223 are pulled, and with these angle wires 223 operated, the curvable portion 209 is curved.

In the case where the distal end structure portion 210 of the endoscope 202 is inserted to, for example, a deep part of the large intestine through curved sections of the body cavity, or it is inserted to a deep portion of a pipe path for an industrial use, the insertion portion 206 is further inserted while the curvable portion 209 is curved to follow the shape of the cavity in which the portion is inserted. As the insertion portion 206 is inserted, the flexible tube portion 208 is deformed in accordance with the shape of the insertion tube path.

Further, in the embodiment, during the insertion operation of the insertion portion 206 of the endoscope 202, the magnetic fields generated from the coils 231 of the shape detection probe 228 are detected by the antenna 217. The output signal from the antenna 217 is input to the shape detection control device 216, so as to detect the shape of the insertion portion 206, and the detected shape of the insertion portion 206 is displayed on the second monitor 205 for the exclusive purpose. Here, on the screen of the second monitor 205, the positions where the coils 231 are detected on the basis of the magnetic fields generated from those magnetic field generating coils 231 of the shape detection probe 228 are displayed in the form of dot. Then, as the dots of the detection positions of the coils 231 are connected, the entire shape of the insertion portion 206 can be displayed on the screen of the second monitor 205 in the form of pseudo-image.

Further, while the curvable portion 209 of the endoscope 202 is not being curved, it is maintained in a standard shape which is drawn in substantially a linear state. In this state, the gap portions 221 having a V-letter shape between the end edge portions of adjacent pair of curvable pieces 218 are maintained at the same intervals in all directions, that is, up, down, right and left directions, of each angle wire 223.

Further, in order to curve the curvable portion 209, as the leading end curvable piece 218A is pulled to the hand side by means of the angle wires 223 which is pulled, each curvable piece 218 is pivoted around the pivotal pin 220 so as to narrow the V-shaped gap portions 221 between the end edge portions of the curvable pieces 218 on a side of the direction in which the angle wires 223 are pulled, whereas to widen the gap portions 221 on the opposite side. Thus, the entire curvable portion 209 is curved in substantially an arc shape.

Further, by the curving operation of the curvable portion 209, it can be curved to form an arbitrarily curved shape between the standard shape which is drawn in substantially a linear state and a maximum curved shape which is curved in an arc state. It should be noted here that when the curvable portion 209 is curved at maximum, the V-shaped gap portions 221 between the end edge portions of adjacent pairs of the curvable pieces 218 are narrowed such that the end edge portions of each adjacent pair of front one and next curvable pieces 218 abut against each other.

While the curvable portion 209 is curved at maximum, if it is curved in the direction in which the radius of curvature becomes minimum or in the direction in which the amount of curvature becomes maximum, the contents within the curvable portion 209 are curved in accordance with the curved shape of the curvable portion 209. Here, the insertion portion shape detection probe 228 will have to move only by a small amount in the axial direction in respect to the curving operation, since it is located at substantially the central portion with respect to the up-and-down direction in which the radius of curvature of the curvable portion 209 becomes minimum or the amount of curvature becomes large when the curvable portion 209 is curved at maximum. For this reason, the compression and tension on the shape detection probe 228 is significantly reduced.

During the curving operation for the curvable portion in the right-to-left direction, there result some compression and tension forces acting on the shape detection probe 228; however the right-to-left direction curving operation involves curving angles smaller as compared to the case of the up-and-down direction curving operation, and further the right-to-left operation is not frequently operated. Consequently, the shape detection probe 228 is not very much affected.

With the above-described structure, the following effect can be obtained. That is, in the embodiment, the insertion portion shape detection probe 228 is located at substantially the central portion with respect to the up-and-down direction in which the radius of curvature of the curvable portion 209 becomes minimum or the amount of curvature becomes large when the curvable portion 209 is curved at maximum. For this reason, the compression and tension acting on the shape detection probe 228 while curving the curvable portion 209 is significantly reduced as compared to the conventional case. Thus, the tensile force and bending force acting on the connection portion between a coil end of the coil 231b of the shape detection probe 228 and a signal line 232, around the end edge of the coil 231b of the armor tube 233 and the like while operating the curvable portion 209 to curve, can be made small. Consequently, the durability of the insertion portion shape detection probe 228 can be improved, and the durability of the endoscope 202 in which the insertion portion shape detection probe 228 is built, can be improved.

Further, the insertion portion shape detection probe 228 of the endoscope 202 is extended in substantially a linear manner in the insertion portion 206 over the entire length of the insertion portion 206 of the endoscope 202 while positions of the probe 228 taken in its diameter direction are situated at substantially the same location. With this structure, the shape detection probe 228 does not cross with the other contents within the insertion portion 206 of the endoscope 202, and therefore the shape detection probe 228 can be moved smoothly in the axial direction within the insertion portion 206 of the endoscope 202. In this manner, an excessive tensile force or bending force is not created in the shape detection probe 228 while deforming the insertion portion 206, and therefore the probe 228 is not easily damaged.

Figure 27:
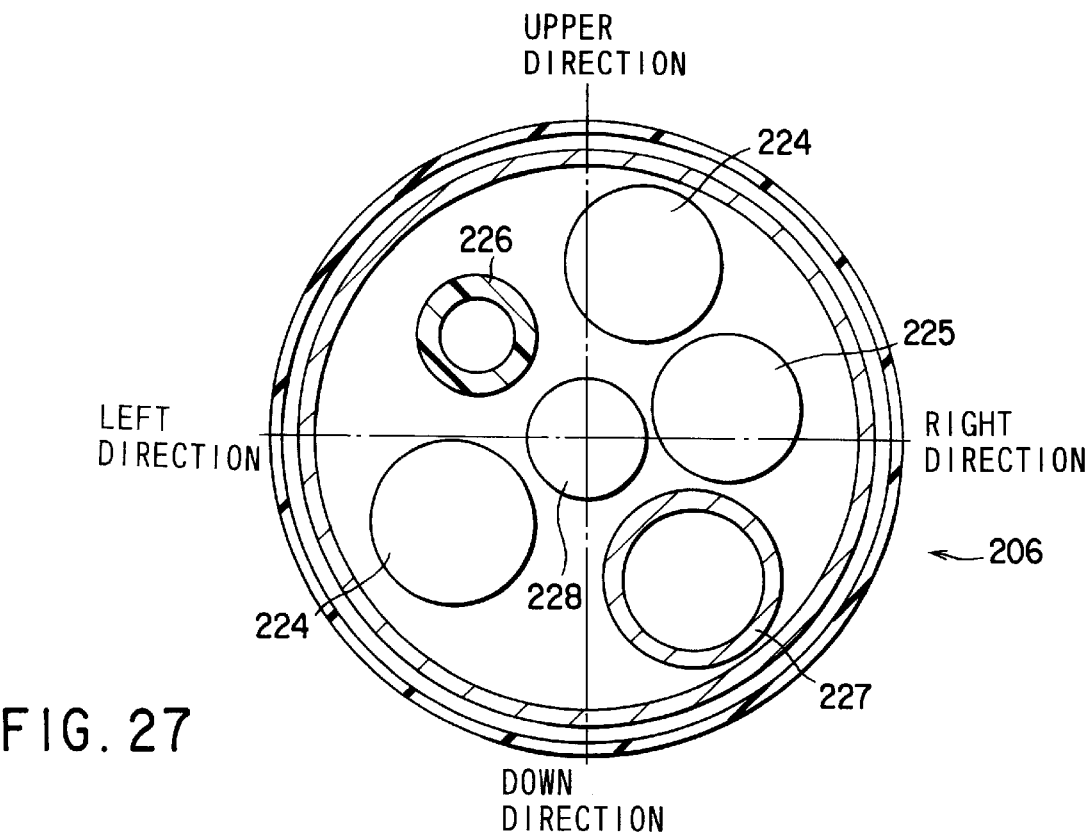
FIG. 27 is a cross sectional view of an insertion portion in the endoscope according to the fifteenth embodiment.

FIG. 27 shows the fifteenth embodiment of the present invention. This embodiment is a remodeled version of the fourteenth embodiment (see FIGS. 23 to 26), in which the shape detection probe 228 is provided close to the central axis of the insertion portion 206 as will now be described. It should be noted that the sections other than the above-mentioned structure are the same as those of the fourteenth embodiment. Here, the same structural elements as those of the fourteenth embodiment will be designated by the same reference numerals, and the explanations therefor will not be repeated.

In the embodiment, the insertion portion shape detection probe 228 is disposed close to the central axis of the insertion portion. With this structure, the compression and tension acting on the shape detection probe 228 while curving the curvable portion 209 in any of the up, down, right and left directions, can be significantly reduced as in the fourteen embodiment. Therefore, as in the case of the fourteen embodiment, the tensile force and bending force acting on the connection portion between a coil end of the coil 231b of the shape detection probe 228 and a signal line 232, around the end edge of the coil 231b of the armor tube 233 and the like while operating the curvable portion 209 to curve, can be made small. Consequently, the durability of the insertion portion shape detection probe 228 can be further improved, and the durability of the endoscope 202 in which the insertion portion shape detection probe 228 is built, can be improved.

Figure 28:
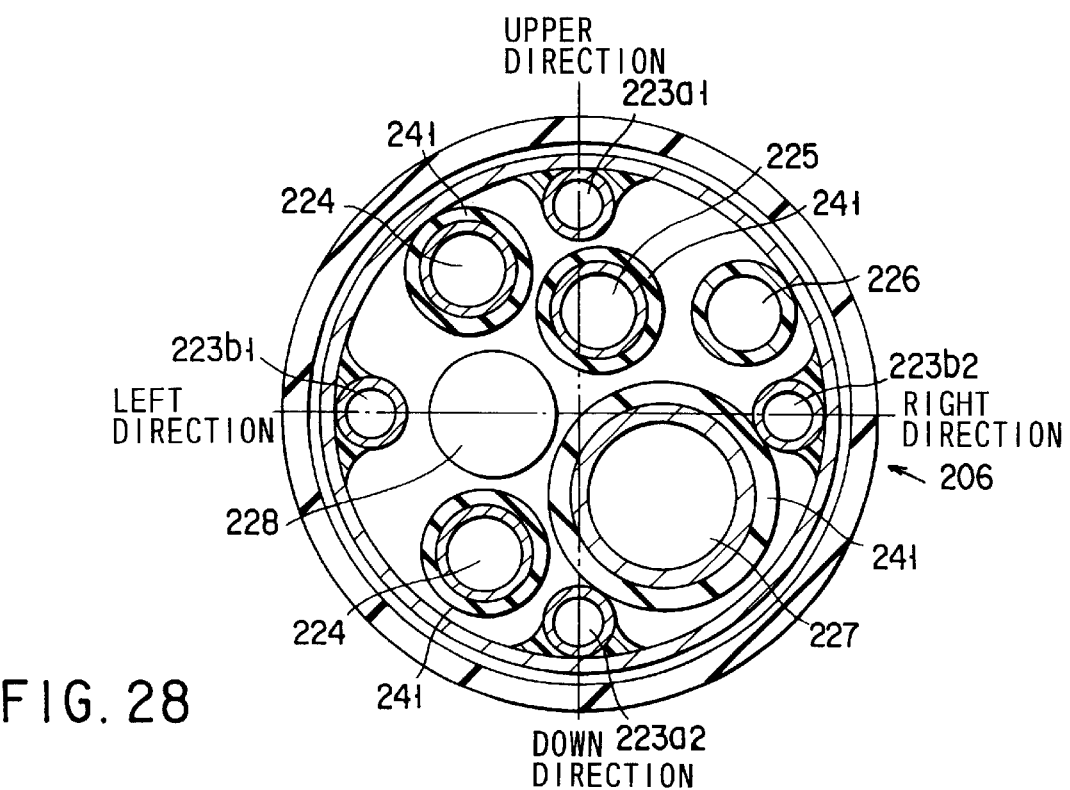
FIG. 28 is a cross sectional view of an insertion portion in the endoscope according to the sixteenth embodiment.

FIG. 28 shows the sixteenth embodiment of the present invention. This embodiment is a remodeled version of the fourteenth embodiment (see FIGS. 23 to 26), in which the outer circumferential surface of each of the contents such as the two light guide fibers 224, the image signal transmission cable 225 and the treatment tool through channel 227, which are disposed adjacent to the insertion shape detection probe 228 in the insertion portion 206 of the endoscope 202, is covered with a protection tube 241 made of, for example, a rubber tube, having a flexibility higher than that of the shape detection probe 228.

Thus, in this embodiment, the protection tube 241 having a flexibility higher than that of the shape detection probe 228 is mounted on the outer circumferential surface of each of the contents such as the two light guide fibers 224, the image signal transmission cable 225 and the treatment tool through channel 227, which are disposed adjacent to the insertion shape detection probe 228 in the insertion portion 206 of the endoscope 202. With this structure, the contents such as the two light guide fibers 224, the image signal transmission cable 225 and the treatment tool through channel 227, will not be brought into direct contact with the insertion portion shape detection probe 228. Therefore, the shape detection probe 228 will not be damaged as the other contents provided in the insertion portion 206 are brought into direct contact with the shape detection probe 228. In this manner, the durability of the insertion portion shape detection probe 228 and the durability of the endoscope 202 can be easily improved.

FIGS. 29A to 29C show the seventeenth embodiment of the present invention. This embodiment is a remodeled version of the fourteenth embodiment (see FIGS. 23 to 26), in which the structure of the entire system of the endoscope device 201 is changed as will now be described.

That is, in the system of the endoscope device 201 of this embodiment, a plurality of types of endoscopes 202 having insertion portions 206 of different lengths and a shape detection probe 228C which is a separate unit from an endoscope 202 are prepared in advance, and various types of medical treatment devices are appropriately and selectively used. FIG. 29A illustrates a shape detection probe 228A built in an endoscope 202 having a long-scale insertion portion 206, FIG. 29B illustrates a shape detection probe 228B built in an endoscope 202 having a short-scale insertion portion 206, and FIG. 29C illustrates a shape detection probe 228C used as being inserted to the treatment tool through channel 227 of an endoscope 202. In this embodiment, in these types of the shape detection probe 228A built in an endoscope 202 shown in FIG. 29A, the shape detection probe 228B built in an endoscope 202 shown in FIG. 29B and the shape detection probe 228C shown in FIG. 29C, the number of coils 231 each being a source of generating a magnetic field, should be made the same regardless of the different in length of the insertion portion 206 of the endoscope 202 applied to each of the device type. Further, the coils are arranged in order side by side at predetermined intervals from the distal end side of each of the shape detection probes 228A, 228B and 228C, and intervals S1, S2 and S3 between adjacent coils 231 located one front and the other next, are set to be the same (S1=S2=S3).

Further, while the system of the endoscope device 201 of this embodiment is in use, the shape of the section of the insertion 206 of the endoscope 202 which corresponds to a region in which the coil 231 is provided in each type of the shape detection probe 228A built in the endoscope 202 shown in FIG. 29A, the shape detection probe 228B built in the endoscope 202 shown in FIG. 29B and the shape detection probe 228C shown in FIG. 29C, that is, the shape of a certain region of the distal end side of the insertion portion 206 of each endoscope 202, is displayed on the second monitor 205.

With the above-described structure, the following effect can be obtained. That is, in this embodiment, with regard to these types of the shape detection probe 228A built in an endoscope 202 shown in FIG. 29A, the shape detection probe 228B built in an endoscope 202 shown in FIG. 29B and the shape detection probe 228C shown in FIG. 29C, the number of coils 231 each being a source of generating a magnetic field, should be made the same regardless of the different in length of the insertion portion 206 of the endoscope 202 applied to each of the device type, and therefore the number of signal lines from each coil 231 extended to the end portion of each of the shape detection probes 228A to 228C will be the same as well among these types of devices. With this structure, a common single type of connector can be used to be mounted to the terminal portion of each of the shape detection probes 228A to 228C, and therefore the entire structure of the system of the endoscope device 201 can be simplified as compared to the case where exclusive types of connectors are used for various types of devices as in the case where the number of coils 231 installed in the respective shape detection probes differs from one probe to another depending on the different in the length of the insertion portion 206 of the endoscope 202.

Further, in this embodiment, with regard to each of different types of the shape detection probes 228A, 228B and 228C, the same number of coils 231 are arranged in order at predetermined intervals from the distal end side, and the intervals S1, S2 and S3 between front-to-rear adjacent coils 231 are set to be at the same interval (that is, S1=S2=S3). With this structure, in all of the device types of the shape detection probe 228A built in an endoscope 202 shown in FIG. 29A, the shape detection probe 228B built in an endoscope 202 shown in FIG. 29B and the shape detection probe 228C shown in FIG. 29C, one shape display system can be shared in common in terms of software. Therefore, according to this embodiment, the production cost for the entire system of the endoscope 201 can be reduced as compared to the conventional endoscope equipped with the shape detection function, in which the number of coils 231 each generating a magnetic field, differs from one device type to another, depending on the length of the insertion portion 206 of the endoscope 202, and therefore endoscopes 202 having different lengths from each other cannot be operated by one shape display system.

Furthermore, according to this embodiment, the number of coils 231 provided in the shape detection probe 228A built in the endoscope 202 with a long-scale insertion portion 206 can be reduced as compared to the case of the conventional shape detection probe 228D (see FIG. 7D). Therefore, such a long-scale shape detection probe 228A can be manufactured at low cost.

In addition, even if the number of coils 231 provided in the shape detection probe 228A built in the endoscope 202 with a long-scale insertion portion 206 is reduced, the shape of a certain region of the distal end side of the insertion portion 206 of the endoscope 202 can be accurately displayed, and therefore the examination cannot be disturbed.

FIGS. 30A to 30D show the eighteenth embodiment of the present invention. This embodiment is a remodeled version of the seventeenth embodiment (see FIGS. 29A to 29C), in which the structure of the entire system of the endoscope device 201 is changed as will now be described.

That is, as in the case of the seventeenth embodiment, in a plurality of types of shape detection probes 228A2, 228B2, 228C2 and 228D2 which are used in different types of devices having insertion portions 206 of different lengths, the number of coils 231 installed each being a source of generating a magnetic field, is made the same, and the coils are arranged substantially uniformly over the entire insertion portion 206. Here, FIG. 30A illustrates a shape detection probe 228A2 built in an endoscope 202 having a long-scale insertion portion 206, FIG. 30B illustrates a shape detection probe 228B2 built in an endoscope 202 having a short-scale insertion portion 206, FIG. 30C illustrates a long-scale shape detection probe 228C2 used as being inserted to the treatment tool through channel 227 of an endoscope 202, and FIG. 30D illustrates a short-scale shape detection probe 228D2 used as being inserted to the treatment tool through channel 227 of an endoscope 202.

Figures 30A, 30B, 30C, 30D:
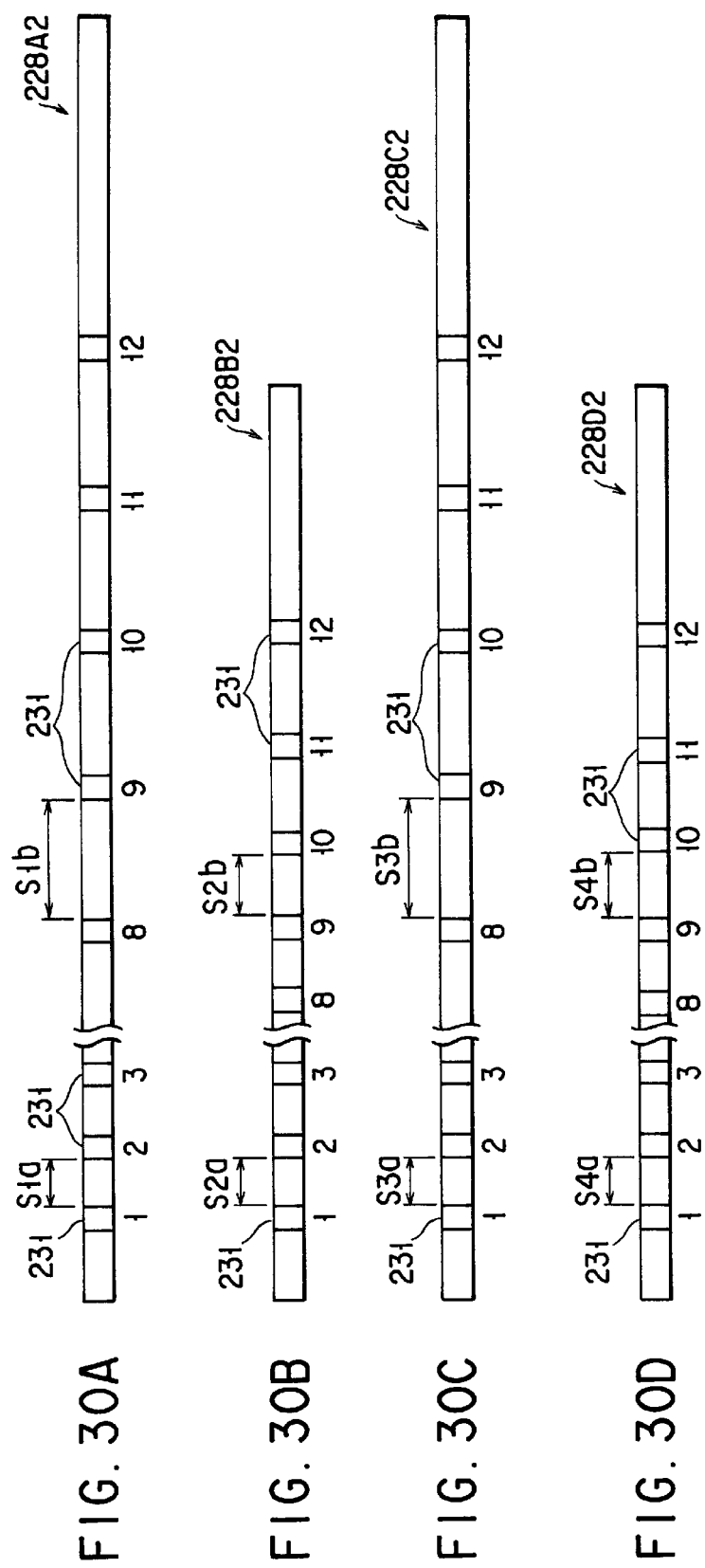
FIG. 30A is a longitudinal sectional view designed to illustrate an arrangement state of coils of a shape detection probe built in an endoscope having a long-scale insertion portion, according to the eighteenth embodiment.
FIG. 30B is a longitudinal sectional view designed to illustrate an arrangement state of coils of a shape detection probe built in an endoscope having a short-scale insertion portion, according to the eighteenth embodiment.
FIG. 30C is a lateral view designed to illustrate an arrangement state of coils of a long-scale shape detection probe inserted in a treatment tool through channel of the endoscope according to the eighteenth embodiment.
FIG. 30D is a lateral view designed to illustrate an arrangement state of coils of a short-scale shape detection probe inserted in a treatment tool through channel of the endoscope according to the eighteenth embodiment.

Further, in the shape detection probe 228A2 shown in FIG. 30A, the coils 231 are arranged in such a manner that an interval S1$b$ between front-to-rear adjacent coils 231 located on the rear end side of the probe becomes larger increasingly from an interval S1$a$ between adjacent pair of coils 231 located on the distal end side. Further, in a similar manner, in each of the shape detection probe 228B2 shown in FIG. 30B, the shape detection probe 228C2 shown in FIG. 30C and the shape detection probe 228D2 shown in FIG. 30D, the coils 231 are arranged in such a manner that an interval S2$b$, S3$b$ or S4$b$, respectively, between front-to-rear adjacent coils 231 located on the rear end side of the probe becomes larger increasingly from an interval S2$a$, S3$a$ or S3$a$, respectively, between adjacent pair of coils 231 located on the distal end side. Thus, in this embodiment, the coils 231 are arranged by appropriately changing the interval between adjacent pair of coils 231, one front and the other next, depending upon the location within the insertion portion 206 of the endoscope 202.

Further, while the system of the endoscope device 201 of this embodiment is in use, the shape of substantially the entirety of the insertion 206 of the endoscope 202 which corresponds to a respective type of the shape detection probe 228A2 shown in FIG. 30A, the shape detection probe 228B2 shown in FIG. 30B, the shape detection probe 228C2 shown in FIG. 30C and the shape detection probe 228D2 shown in FIG. 30D, is displayed on the second monitor 205.

With the above-described structure, the following effect can be obtained. That is, in this embodiment, with regard to these types of the shape detection probe 228A2 shown in FIG. 30A, the shape detection probe 228B2 shown in FIG. 30B, the shape detection probe 228C2 shown in FIG. 30C and the shape detection probe 228D2 shown in FIG. 30D, the number of coils 231 each being a source of generating a magnetic field, is made the same regardless of the different in length of the insertion portion 206 of the endoscope 202 applied to each of the device type, and therefore the number of signal lines from each coil 231 extended to the end portion of each of the shape detection probes 228A2 to 228D2 will be the same as well among these types of devices. With this structure, a common single type of connector can be used to be mounted to the terminal portion of each of the shape detection probes 228A2 to 228D2, and therefore the entire structure of the system of the endoscope device 201 can be simplified as in the case of the seventeenth embodiment.

Further, in this embodiment as well, with regard to all of the types of the devices, one shape display system can be shared in common in terms of software. Therefore, the production cost for the entire system of the endoscope 201 can be reduced.

Figure 31:
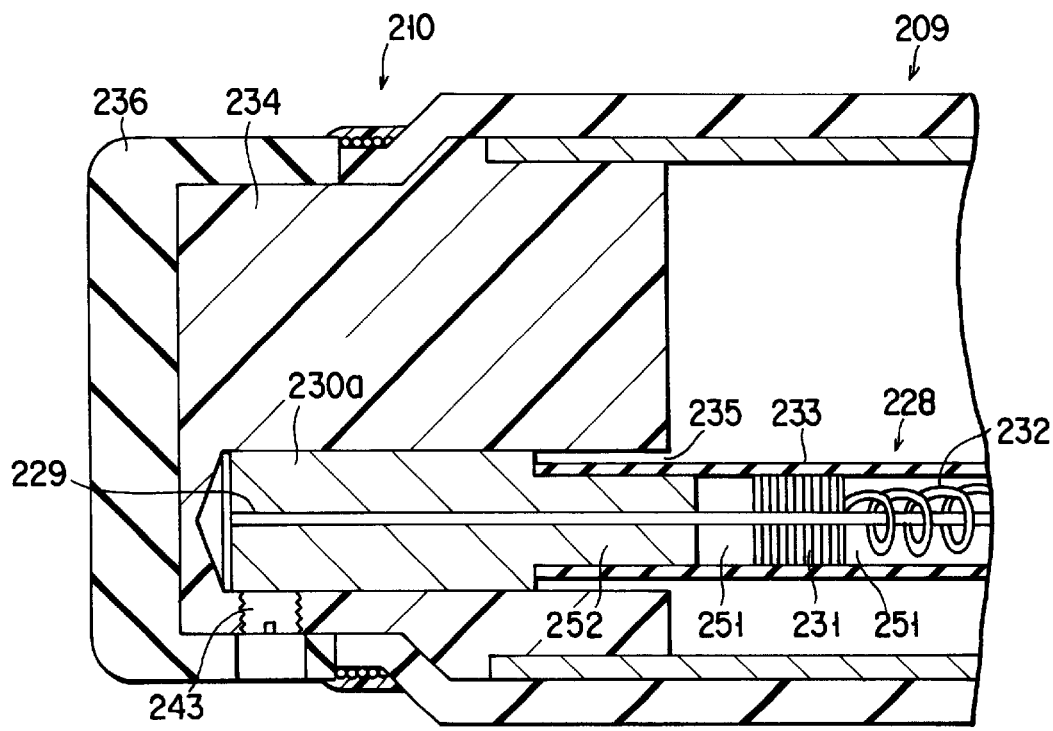
FIG. 31 is a longitudinal sectional view showing a fixation state of a distal end of the shape detection probe in the endoscope according to the nineteenth embodiment.

FIG. 31 shows the nineteenth embodiment of the present invention. This embodiment is a remodeled version of the fourteenth embodiment (see FIGS. 23 to 26), where the structure of the shape detection probe 228 is changed as will be described.

That is, in the fourteenth embodiment, the filler 242 prepared by mixing silicon and a solvent is packed into the armor tube 233 to fill the gaps between the contents therein, such as the core wire 229, the coils 231 and signal wires 232. By contrast, in this embodiment, a relatively hard filler 251 designed to prevent the buckling of the armor tube 233 is packed into the armor tube 233 of the shape detection probe 228 so as to fill the gaps between the contents therein, such as the core wire 229, the coils 231 and signal wires 232. The filler 251 is made of, for example, silicon only or a mixture of silicon and a solvent, with a reduced amount of the solvent mixed therein.

As described above, in this embodiment, the relatively hard filler 251 designed to prevent the buckling of the armor tube 233 is packed into the armor tube 233 of the shape detection probe 228 so as to fill the gaps between the contents therein. Therefore, the buckling of the armor tube 233 can be prevented, and the disconnection of the signal line 232 of the shape detecting probe 228 can be prevented. Therefore, the durability of the insertion portion shape detection probe 228 can be improved, and accordingly, the durability of the endoscope 202 can be improved.

Figure 32:
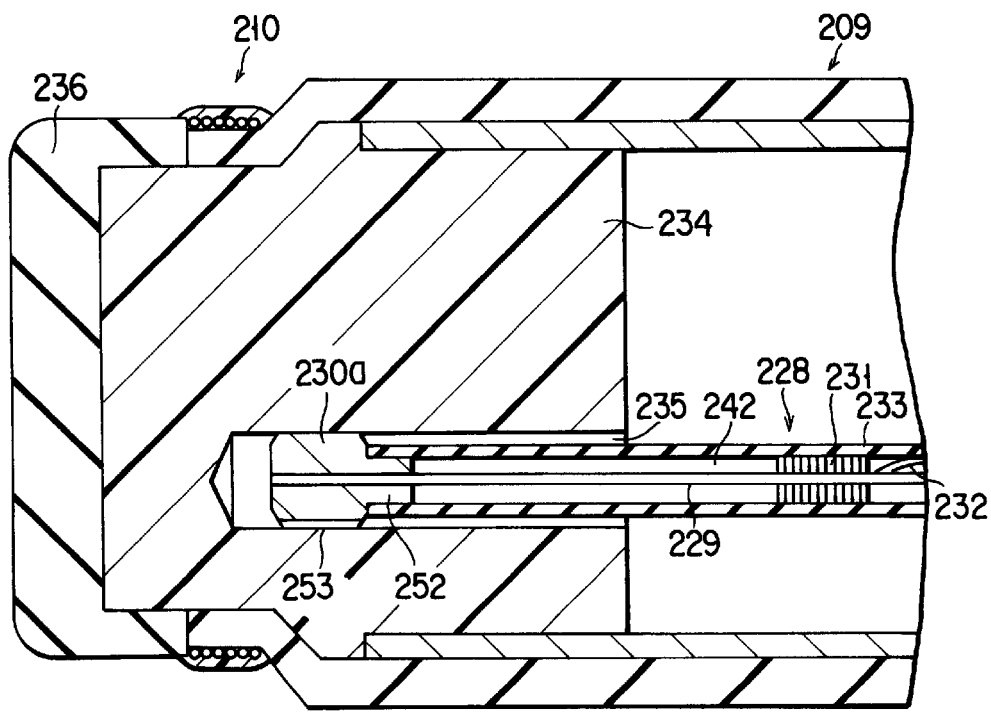
FIG. 32 is a longitudinal sectional view showing a mount state of a distal end of the shape detection probe in the endoscope according to the twentieth embodiment.
Figure 33:
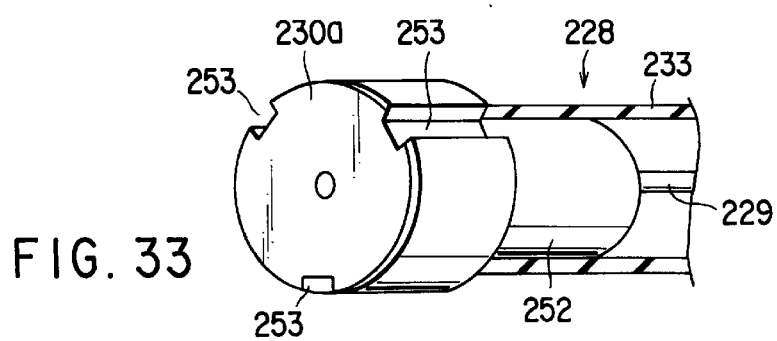
FIG. 33 is a perspective view of the distal end portion of the shape detection probe according to the twentieth embodiment.

FIGS. 32 and 33 show the twentieth embodiment of the present invention. This embodiment is a remodeled version of the fourteenth embodiment (see FIGS. 23 to 26), where the structure of the shape detection probe 228 is changed as will be described.

That is, in the fourteenth embodiment, the distal end member 230$a$ of the shape detection probe 228 is fixed by means of the fixation screw 243 while being inserted to the shape detection probe mount hole 235 of the distal end structure main body 234 of the endoscope 202. By contrast, in this embodiment, the distal end of the shape detection probe 228 is made to be a free end. Here, the outer diameter of the distal end member 230$a$ of the shape detection probe 228 is made slightly smaller than the inner diameter of the shape detection probe mount hole 235 of the distal end structure main body 234.

In this embodiment, while the distal end member 230$a$ of the shape detection probe 228 is being inserted to the shape detection probe mount hole 235 of the distal end structure main body 234, the distal end member 230$a$ of the shape detection probe 228 is engaged therein to be movable in the axial direction of the shape detection probe mount hole 235.

Further, in this embodiment, in a rear end portion of the distal end member 230$a$ of the shape detection probe 288, a tube fixation portion 252 having a small diameter is formed to project. The distal end portion of the armor tube 233 is fixed to the tube fixation portion 252 while it is fit therein.

Furthermore, a plurality of, in this embodiment, three, air vent grooves 253 are made in the outer circumferential surface of the distal end member 230$a$, are made along the axial direction as can be seen in FIG. 33. With this structure, as the distal end member 230$a$ of the shape detection probe 288 moves forwards within the probe mount hole 235, air is released from these air vent grooves 253.

Therefore, in this embodiment, since the distal end of the shape detection probe 228 is engaged with the probe mount hole 235 to be moveable in the axial direction within the mount hole 235. With this structure, when a compression force is applied to the shape detection probe 228 when the curvable portion 209 is curved, the distal end member 230*a* of the shape detection probe 288 moves to the distal end side within the probe mount hole 235, so as to reduce (release) the force. Similarly, the tensile force acting on the shape detection probe 288 can be reduced. Thus, an excessive tensile force and compression force acting on the shape detection probe 228, which may occur each time the curvable portion 209 is curved in the case where the distal end of the shape detection probe 228 is fixed within the probe mount hole 235, can be prevented. Therefore, damages to the shape detection probe 228, which may occur while the curvable portion 209 is curved, can be prevented, and therefore the durability of the shape detection probe 228 can be improved.

Figure 34:
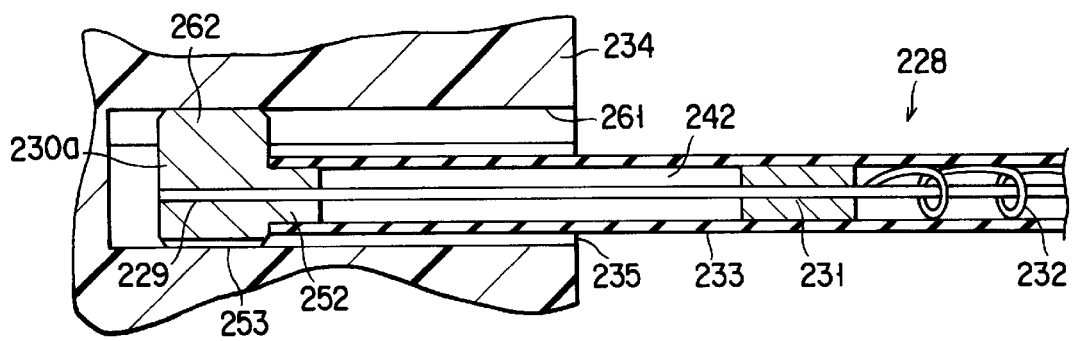
FIG. 34 is a longitudinal sectional view showing a state of a distal end of the shape detection probe mounted in the endoscope according to the twenty first embodiment of the present invention.
Figure 35A:
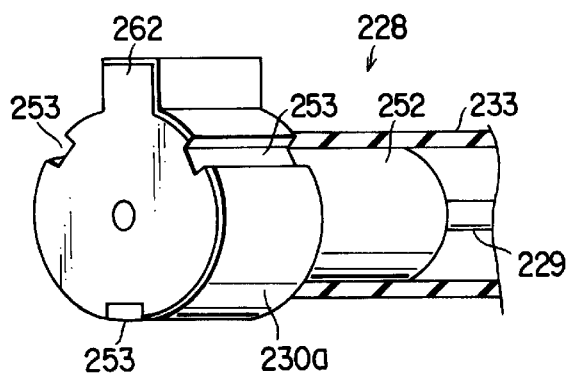
FIG. 35A is a perspective view of the distal end portion of the shape detection probe according to the twenty first embodiment.
Figure 35B:
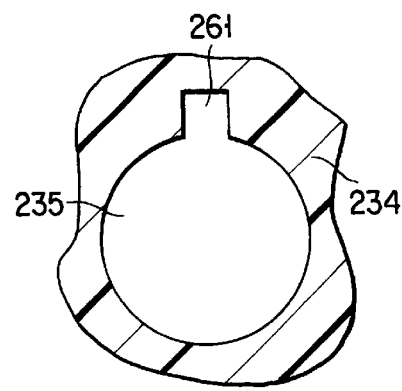
FIG. 35B is a cross sectional view of a main portion, illustrating a probe mount hole of the distal end structure of the endoscope.

FIGS. 34, 35A and 35B show the twenty first embodiment of the present invention. This embodiment is a remodeled version of the twentieth embodiment (see FIGS. 32 and 33), where the structure of the shape detection probe 228 is changed as will be described.

That is, in this embodiment, as shown in FIG. 35B, an engagement groove 261 having substantially a shape of a key groove of a straight line, is made in an inner circumferential surface of the shape detection probe mount hole 235 of the distal end structure main body 234, in the axial direction of the probe mount hole 235. Further, a projection portion 262 for stopping the member from rotating, which engages with an engagement groove 261 of the detection probe mount hole 235, is provided on the outer circumferential surface of the distal end member 230*a* of the shape detection probe 228.

Thus, in this embodiment, the projection portion 262 of the distal end member 230*a* of the shape detection probe 228 is provided to engage with the engagement groove 261 of the detection probe mount hole 235, and therefore the rotation of the shape detection probe 228 in the axial rotation direction with respect to the distal end structure main body 234 of the endoscope 202 can be prevented.

Figure 36:
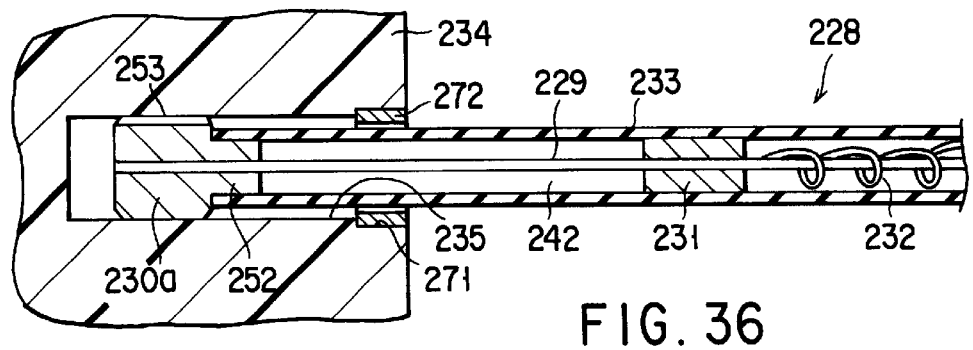
FIG. 36 is a longitudinal sectional view showing a mount state of a distal end of a shape detection probe in an endoscope according to the twenty-second embodiment of the present invention.
Figure 37A:
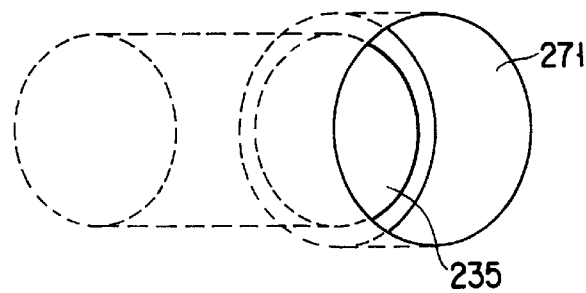
FIG. 37A is a perspective view of a main portion, illustrating a probe mount hole of the distal end structure of the endoscope of the twenty-second embodiment.
Figure 37B:
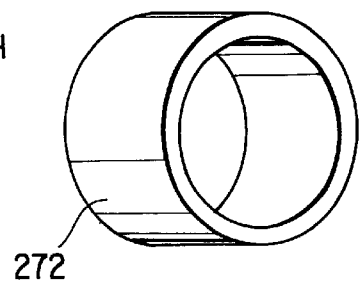
FIG. 37B is a perspective view showing a stopper ring fixed to the probe mount hole of the distal end structure of the endoscope.

FIGS. 36, 37A and 37B show the twenty second embodiment of the present invention. This embodiment is a remodeled version of the twentieth embodiment (see FIGS. 32 and 33), where the structure of the shape detection probe mount hole 235 of the distal end structure main body 234 is changed as will be described.

That is, in this embodiment, as shown in FIG. 37A, a ring-like groove 271 having a diameter larger than that of the probe mount hole 235 is formed at an entrance portion of the shape detection probe mount hole 235 of the distal end structure main body 234. In the ring-like groove 271, a stopper ring 272 shown in FIG. 37B, is provided, which is designed to prevent the distal end portion 230*a* of the shape detection probe 228 inserted in the probe mount hole 235 from falling off therefrom. The inner diameter of the stopper ring 272 is set to be smaller than the outer diameter of the distal end member 230*a* of the shape detection probe 228.

With the above-described structure, when the distal end member 230*a* of the shape detection probe 228 moves to the rear end side within the probe mount hole 235, the rear end portion of the distal end member 230*a* of the shape detection probe 228 abuts against the stopper ring 272 provided at the entrance portion of the probe mount hole 235. Thus, the falling-off of the distal end member 230*a* of the shape detection probe 228 from the probe mount hole 235 can be certainly prevented.

Figure 38:
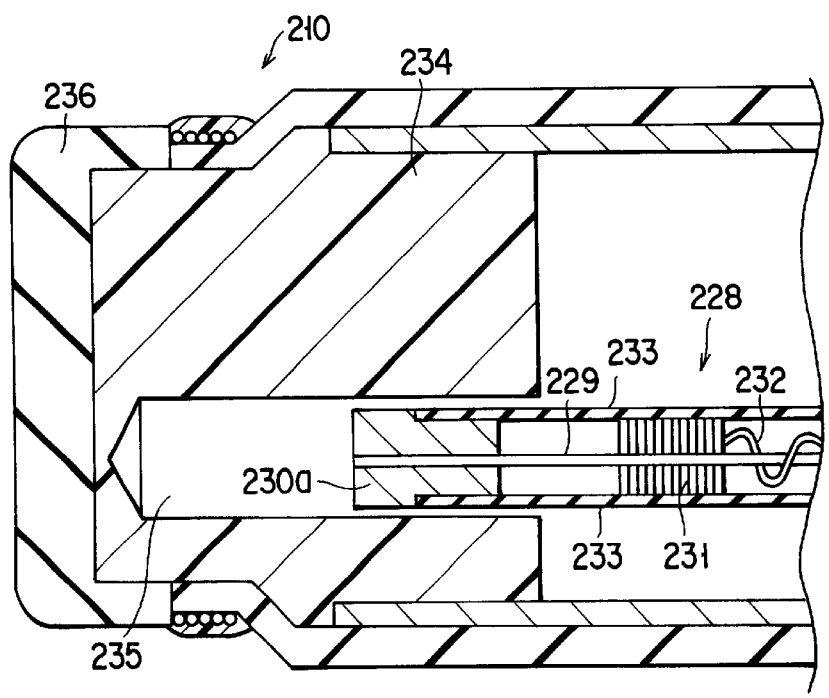
FIG. 38 is a longitudinal sectional view showing a mount state of a distal end of a shape detection probe in an endoscope according to the twenty-third embodiment of the present invention.
Figure 39A:
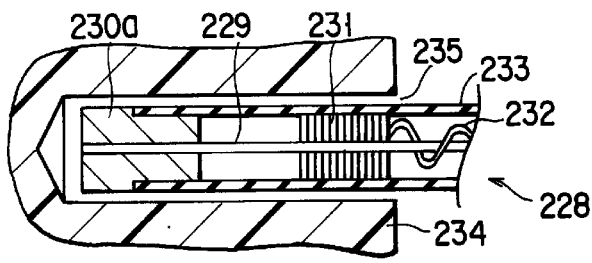
FIG. 39A is a longitudinal sectional view of a main portion, illustrating such a state that the distal end of the shape detection probe is inserted to the deepest section of the probe mount hole of the distal end structure portion of the endoscope according to the twenty-third embodiment.
Figure 39B:
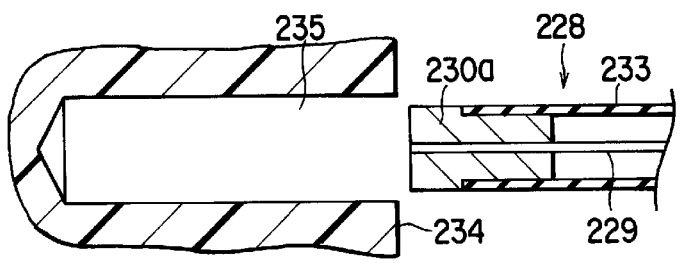
FIG. 39B is a longitudinal sectional view of a main portion, illustrating such a state that the shape detection probe is extracted from the probe mount hole of the distal end structure portion of the endoscope.

FIGS. 38, 39A and 39B show the twenty third embodiment of the present invention. This embodiment is a remodeled version of the fourteenth embodiment (see FIGS. 23 to 26), where the structure of the endoscope 202 is changed as will be described.

That is, in this embodiment, the outer diameter of the distal end member 230*a* of the shape detection probe 228 is made smaller than the inner diameter of the probe mount hole 235 of the distal end structure main body 234, so as to create a gap between the outer circumferential surface of the distal end member 230*a* and the inner circumferential surface of the probe mount hole 235. Thus, the distal end member 230*a* of the shape detection probe 228 is made movable freely within the probe mount hole 235 along its axial direction. Here, the probe mount hole 235 is formed to have such a depth that the distal end portion of the shape detection probe 228 does not abut on an inner bottom portion of the probe mount hole 235 when the curvable portion 209 is curved up to the maximum curvable angle.

Therefore, in this embodiment, since the distal end of the shape detection probe 228 is maintained within the probe mount hole 235 to be moveable in the axial direction within the mount hole 235. With this structure, when a compression force is applied to the shape detection probe 228 when the curvable portion 209 is curved, the distal end member 230*a* of the shape detection probe 288 can move to the distal end side within the probe mount hole 235, so as to reduce (release) the force. Similarly, the tensile force acting on the shape detection probe 288 can be reduced. Thus, an excessive tensile force and compression force acting on the shape detection probe 228 in the axial direction, which may occur each time the curvable portion 209 is curved in the case where the distal end of the shape detection probe 228 is fixed within the probe mount hole 235, can be prevented. Therefore, damages to the shape detection probe 228, which may occur while the curvable portion 209 is curved, can be prevented, and therefore the durability of the shape detection probe 228 can be improved.

Further, the depth of the probe mount hole 235 is set such that the distal end portion of the shape detection probe 228 does not abut on the inner bottom portion of the probe mount hole 235 when the curvable portion 209 is curved up to the maximum curvable angle. Therefore, even if the curvable portion 209 is curved at the maximum curvable angle, the distal end portion of the shape detection probe 228 will not be brought into direct contact with the inner bottom portion of the probe mount hole 235, and thus damages on the shape detection probe 228, which might be caused by such contact, can be prevented.

Figure 40:
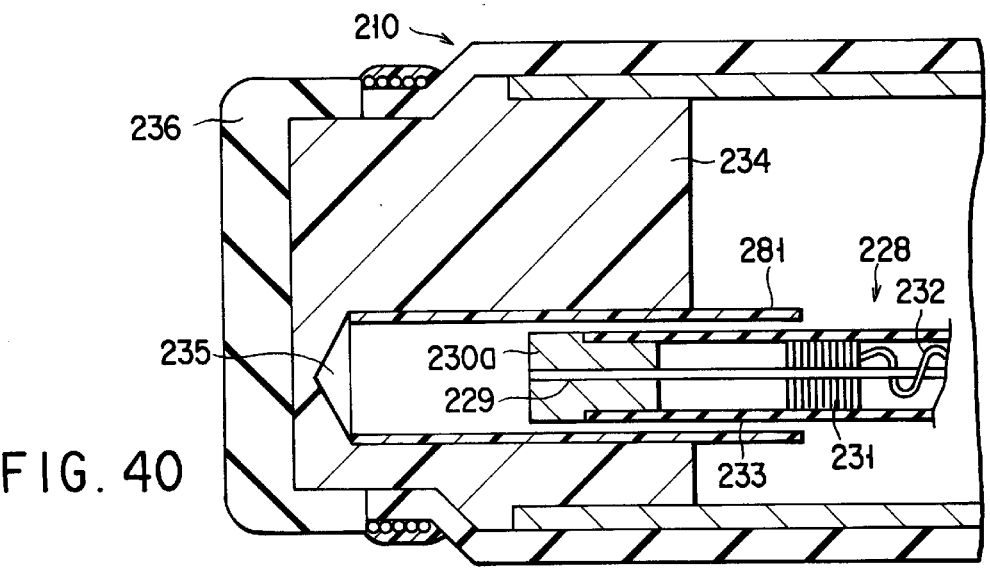
FIG. 40 is a longitudinal sectional view showing a mount state of a distal end of a shape detection probe in an endoscope according to the twenty fourth embodiment of the present invention.

FIG. 40 shows the twenty fourth embodiment of the present invention. This embodiment is a remodeled version of the twenty third embodiment (see FIGS. 38, 39A and 39B), where the structure of the endoscope 202 is changed as will be described.

That is, in this embodiment, a guide pipe 281 for guiding the movement of the distal end portion of the shape detection probe 228 in the axial direction, is provided on the inner circumferential surface of the probe mount hole 235 of the twenty third embodiment. A rear end portion of the guide pipe 281 is extended outwards from the probe mount hole 235. Therefore, the falling-off of the distal end portion of the shape detection probe 228 out of the probe mount hole 235 can be prevented by the rear end extended portion of the guide pipe 281.

With the above-described structure, in addition to a similar effect to that of the twenty third embodiment, the falling-off of the distal end portion of the shape detection probe 228 out of the probe mount hole 235 can be prevented by the rear end extended portion of the guide pipe 281, in this embodiment. Therefore, the damage on the shape detection probe 228 can be prevented in a more certain way. Further, in this embodiment, the guide pipe 281 serves to prevent the distal end portion of the shape detection probe 228 from moving in the direction crossing normally with the central line of the shape detection probe 228. Therefore, the layout of the contents within the insertion portion 206 of the endoscope 202 is not disturbed as an additional advantage.

Figure 41:
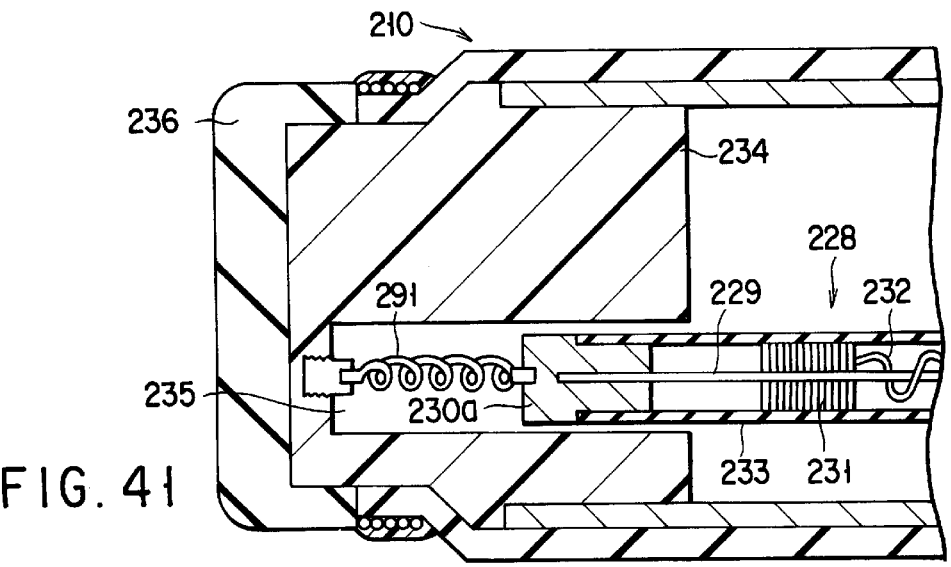
FIG. 41 is a longitudinal sectional view showing a mount state of a distal end of a shape detection probe in an endoscope according to the twenty-fifth embodiment of the present invention.

FIG. 41 shows the twenty fifth embodiment of the present invention. This embodiment is a remodeled version of the twenty third embodiment (see FIGS. 38, 39A and 39B), where the structure of the endoscope 202 is changed as will be described.

That is, in this embodiment, an elastic member such as a coil spring 291 is provided between the inner bottom portion of the probe mount hole 235 of the twenty third embodiment, and the distal end portion of the shape detection probe 228, and the distal end of the shape detection probe 228 is connected via the coil spring 291 to the inner bottom portion of the probe mount hole 235. With this structure, a similar effect to that of the twenty fourth embodiment can be obtained.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope device comprising:
an endoscope including an insertion portion, said insertion portion including a curvable portion and a distal end portion provided at a distal end side of the curvable portion; and
an insertion portion shape detecting probe provided in the insertion portion for detecting a shape of the insertion portion;
wherein the insertion portion shape detecting probe includes: (i) a first magnetic filed generating coil provided at one of a) an extreme distal end position of the curvable portion and b) the distal end portion, (ii) a second magnetic field generating coil provided at an extreme proximal end position of the curvable portion, (iii) a third magnetic field generating coil provided at substantially an intermediate position between the first and second coils, and (iv) a plurality of fourth magnetic field generating coils provided in a section of the insertion portion other than the curvable portion.

2. An endoscope device comprising:
an endoscope including an insertion portion, said insertion portion including a flexible tube portion, a curvable portion and a distal end portion provided at a distal end side of the curvable portion; and
an insertion portion shape detecting probe provided in the insertion portion for detecting a shape of the insertion portion;
wherein the insertion portion shape detecting probe includes: (i) a first magnetic filed generating coil provided at one of a) an extreme distal end position of the curvable portion and b) the distal end portion, (ii) a second magnetic field generating coil provided at an extreme proximal end position of the curvable portion, (iii) a third magnetic field generating coil provided at substantially an intermediate position between the first and second coils, and (iv) a plurality of fourth magnetic field generating coils provided in the flexible tube portion.

3. An endoscope device comprising:
an endoscope including an insertion portion in which an imaging unit and a channel are provided; and
an insertion portion shape detecting probe including a plurality of magnetic field generating coils arranged in an axial direction of the insertion portion for detecting a shape of the insertion portion;
wherein the insertion portion shape detecting probe is situated at a position such that a moving amount of the insertion portion shape detecting probe in the axial direction of the insertion portion when the curvable portion is curved is minimum, and such that insertion portion shape detecting probe does not intersect with the imaging unit and channel provided in the insertion portion.

4. An endoscope device according to claim 3, wherein said insertion portion shape detection probe is situated in substantially a same position in a diameter direction over an entire length of the insertion portion.

5. An endoscope device according to claim 4, wherein the insertion portion shape detecting probe is situated at substantially a central position with respect to up and down curving directions of the curvable portion.

6. An endoscope device comprising:
an endoscope including an insertion portion in which a curvable portion is provided; and
an insertion portion shape detecting probe provided in the insertion portion for detecting a shape of the insertion portion;
wherein the insertion portion shape detecting probe includes: (i) a first magnetic field generating coil provided at one of a) an extreme distal end position of the curvable portion and b) a section of the insertion portion that is on a distal side further than the curvable portion, (ii) a second magnetic field generating coil provided at one of a) an extreme proximal end position of the curvable portion and b) a section of the insertion portion that is on a proximal side further than the curvable portion, and (iii) a third magnetic field generating coil provided at substantially an intermediate position between the first and second coils;
wherein the first coil is provided at the extreme distal end position of the curvable portion and the second coil is provided at the extreme proximal end position of the curvable portion.

7. An endoscope device according to claim 6, wherein:
the endoscope includes a distal end structural portion provided at a distal end portion of the insertion portion;
the distal end structural portion comprises a main body made of a non-magnetic material, and a probe mount portion for mounting a distal end portion of the insertion portion shape detection probe to the main body of the distal end structural portion; and
the first coil is disposed within the main body of the distal end structural portion.

8. An endoscope device according to claim 6, wherein:
the curvable portion comprises a plurality of curvable pieces arranged in one direction of the insertion portion;

the first coil is situated at a position corresponding to one of the curvable pieces that is placed at the extreme distal end of the curvable portion; and the second coil is situated at a position corresponding to one of the curvable pieces that is placed at the extreme proximal end of the curvable portion.

9. An endoscope device according to claim 8, wherein the first, second and third coils are arranged at substantially equal intervals over an overall length of the insertion portion.

10. An endoscope device comprising:

an endoscope including an insertion portion in which a curvable portion is provided; and an insertion portion shape detecting probe provided in the insertion portion for detecting a shape of the insertion portion;

wherein the insertion portion shape detecting probe includes: (i) a first magnetic field generating coil provided at one of a) an extreme distal end position of the curvable portion and b) a section of the insertion portion that is on a distal side further than the curvable portion, (ii) a second magnetic field generating coil provided at one of a) an extreme proximal end position of the curvable portion and b) a section of the insertion portion that is on a proximal side further than the curvable portion (iii) a third magnetic field generating coil provided at substantially an intermediate position between the first and second coils, and (iv) a plurality of fourth magnetic field generating coils provided in a section of the insertion portion other than the curvable portion;

wherein the first coil is provided at the extreme distal end position of the curvable portion and the second coil is provided at the extreme proximal end position of the curvable portion.

11. An endoscope device according to claim 10, wherein:

the endoscope includes a distal end structural portion provided at a distal end portion of the insertion portion;

the distal end structural portion comprises a main body made of a non-magnetic material, and a probe mount portion for mounting a distal end portion of the insertion portion shape detection probe to the main body of the distal end structural portion; and the first coil is disposed within the main body of the distal end structural portion.

12. An endoscope device according to claim 10, wherein:

the curvable portion comprises a plurality of curvable pieces arranged in one direction of the insertion portion;

the first coil is situated at a position corresponding to one of the curvable pieces that is placed at the extreme distal end of the curvable portion; and the second coil is situated at a position corresponding to one of the curvable pieces that is placed at the extreme proximal end of the curvable portion.

13. An endoscope device according to claim 12, wherein the first, second, third and fourth coils are arranged at substantially equal intervals over an overall length of the insertion portion.

14. An endoscope device comprising:

an endoscope including an insertion portion in which a curvable portion is provided; and an insertion portion shape detecting probe provided in the insertion portion for detecting a shape of the insertion portion;

wherein the insertion portion shape detecting probe includes: (i) a first magnetic field generating coil provided at one of a) an extreme distal end position of the curvable portion and b) a portion that is on a distal side further than the curvable portion, (ii) a second magnetic field generating coil provided in a vicinity of a rear end portion of the curvable portion for detecting an extreme rear end portion of the curvable portion, and (iii) at least one third magnetic field generating coil provided between the first magnetic field generating coil and the second magnetic field generating coil.

15. An endoscope device according to claim 14, wherein:

the endoscope includes a distal end structural portion provided at a distal end portion of the insertion portion;

the distal end structural portion comprises a main body made of a non-magnetic material, and a probe mount portion for mounting a distal end portion of the insertion portion shape detection probe to the main body of the distal end structural portion; and the first coil is disposed within the main body of the distal end structural portion.

16. An endoscope device according to claim 14, wherein the second magnetic field generating coil is provided at one of a) the extreme distal end position of the curvable portion and b) a position of the insertion portion which is adjacent to the extreme distal end position of the curvable portion.

17. An endoscope device according to claim 16, wherein the second magnetic field generating coil is provided at a rear end position of the curvable portion.

18. An endoscope device according to claim 17, wherein:

the curvable portion comprises a plurality of curvable pieces arranged in one direction of the insertion portion;

the first magnetic field generating coil is situated at a position corresponding to one of the curvable pieces that is placed at the extreme distal end of the curvable portion; and the second magnetic field generating coil is situated at a position corresponding to one of the curvable pieces that is placed at an extreme proximal end of the curvable portion.

19. An endoscope device according to claim 14, wherein said at least one third magnetic field generating coil comprises a plurality of third magnetic field generating coils arranged between the first and second magnetic field generating coils.

* * * * *